(12) United States Patent
Pangarkar et al.

(10) Patent No.: US 10,823,731 B2
(45) Date of Patent: *Nov. 3, 2020

(54) IMAGE ANALYSIS AND MEASUREMENT OF BIOLOGICAL SAMPLES

(71) Applicant: Labrador Diagnostics LLC, Healdsburg, CA (US)

(72) Inventors: Chinmay Pangarkar, Palo Alto, CA (US); Karan Mohan, Palo Alto, CA (US); James R. Wasson, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 339 days.

This patent is subject to a terminal disclaimer.

(21) Appl. No.: 14/600,630

(22) Filed: Jan. 20, 2015

(65) Prior Publication Data

US 2015/0204788 A1 Jul. 23, 2015

Related U.S. Application Data

(63) Continuation of application No. PCT/US2013/052141, filed on Jul. 25, 2013.
(Continued)

(51) Int. Cl.
*G01N 33/49* (2006.01)
*G02B 7/09* (2006.01)
(Continued)

(52) U.S. Cl.
CPC .. *G01N 33/56972* (2013.01); *B01L 3/502715* (2013.01); *G01N 1/30* (2013.01);
(Continued)

(58) Field of Classification Search
CPC ............. G01N 21/6486; G01N 21/645; G01N 21/0303; G01N 21/05; G01N 21/17;
(Continued)

(56) References Cited

U.S. PATENT DOCUMENTS 3,849,654 A 11/1974 Malvin
3,854,044 A 12/1974 Stay et al.
(Continued)

FOREIGN PATENT DOCUMENTS

CN 201156031 11/2008
EP 0781987 A2 7/1997
(Continued)

OTHER PUBLICATIONS

U.S. Appl. No. 15/340,637, filed Feb. 2017, Mohan.*
(Continued)

*Primary Examiner* — Gailene Gabel

(57) ABSTRACT

Methods, devices, systems, and apparatuses are provided for the image analysis of measurement of biological samples. Specifically, methods are provided for detecting and measuring, in a sample, cell morphology; measurement of cell numbers; detection of particles; measurement of particle numbers; and other properties and quantities of or in a sample. Some embodiments may use a sample holder comprising a sample chamber configured to hold said sample, at least a portion of said sample holder comprising an optically transmissive material, said optically transmissive material comprising an optically transmissive surface and a reflective surface.

13 Claims, 22 Drawing Sheets

Related U.S. Application Data

(60) Provisional application No. 61/675,811, filed on Jul. 25, 2012, provisional application No. 61/676,178, filed on Jul. 26, 2012, provisional application No. 61/766,116, filed on Feb. 18, 2013, provisional application No. 61/802,194, filed on Mar. 15, 2013.

(51) Int. Cl.

| | | |
|---|---|---|
| *G02B 21/16* | (2006.01) | |
| *G01N 21/17* | (2006.01) | |
| *G01N 33/569* | (2006.01) | |
| *B01L 3/00* | (2006.01) | |
| *G01N 15/10* | (2006.01) | |
| *G02B 21/00* | (2006.01) | |
| *G02B 21/12* | (2006.01) | |
| *G01N 21/05* | (2006.01) | |
| *G02B 21/08* | (2006.01) | |
| *G01N 33/50* | (2006.01) | |
| *G01N 1/30* | (2006.01) | |
| *G01N 21/64* | (2006.01) | |
| *G01N 21/03* | (2006.01) | |
| *G02B 21/24* | (2006.01) | |
| *G01N 33/487* | (2006.01) | |
| *G01N 21/27* | (2006.01) | |
| *G02B 21/36* | (2006.01) | |

(52) U.S. Cl.
CPC ..... *G01N 15/1012* (2013.01); *G01N 21/0303* (2013.01); *G01N 21/05* (2013.01); *G01N 21/17* (2013.01); *G01N 21/27* (2013.01); *G01N 21/645* (2013.01); *G01N 21/6428* (2013.01); *G01N 21/6458* (2013.01); *G01N 21/6486* (2013.01); *G01N 33/487* (2013.01); *G01N 33/49* (2013.01); *G01N 33/5005* (2013.01); *G01N 33/56966* (2013.01); *G02B 7/09* (2013.01); *G02B 21/0076* (2013.01); *G02B 21/088* (2013.01); *G02B 21/125* (2013.01); *G02B 21/16* (2013.01); *G02B 21/244* (2013.01); *G02B 21/365* (2013.01); *G01N 2015/1018* (2013.01); *G01N 2021/1738* (2013.01); *G01N 2021/6439* (2013.01); *G01N 2201/061* (2013.01); *G01N 2201/12* (2013.01); *G01N 2333/70589* (2013.01); *G01N 2333/70596* (2013.01)

(58) Field of Classification Search
CPC ......... G01N 21/6458; G01N 33/56972; G01N 33/487; G01N 2201/061; G01N 2201/12; G01N 21/27; G01N 33/49; G01N 33/56966; B01L 3/502715; G02B 7/09; G02B 21/088; G02B 21/0076; G02B 21/125; G02B 21/244; G02B 21/365
See application file for complete search history.

(56) References Cited

U.S. PATENT DOCUMENTS

| | | |
|---|---|---|
| 4,868,126 A | 9/1989 | Schwartz |
| 5,109,429 A | 4/1992 | Bacus et al. |
| 5,292,484 A | 3/1994 | Kelln et al. |
| 5,407,638 A | 4/1995 | Wang |
| 5,414,508 A | 5/1995 | Takahashi et al. |
| 5,534,416 A | 7/1996 | Millard et al. |
| 5,717,778 A | 2/1998 | Chu et al. |
| 5,869,689 A | 2/1999 | Zhang et al. |
| 5,932,428 A | 8/1999 | Dubrow et al. |
| 6,088,097 A | 7/2000 | Uhl |
| 6,396,580 B1 | 5/2002 | Tewes |
| 6,599,475 B1 | 7/2003 | Berndt et al. |
| 6,661,510 B1 | 12/2003 | Hanning et al. |
| 6,690,024 B1 | 2/2004 | Funaoka et al. |
| 7,117,098 B1 | 10/2006 | Dunlay et al. |
| 8,313,713 B2 | 11/2012 | Jacobs et al. |
| 9,122,907 B2 | 9/2015 | Lee et al. |
| 9,494,521 B2 * | 11/2016 | Holmes .................. G01N 21/17 |
| 2001/0028497 A1 | 10/2001 | Uhl |
| 2002/0019062 A1 | 2/2002 | Lea et al. |
| 2003/0104494 A1 * | 6/2003 | Ravkin .................. B82Y 30/00 |
| | | 506/39 |
| 2003/0161572 A1 | 8/2003 | Johnck et al. |
| 2003/0202905 A1 | 10/2003 | Devlin et al. |
| 2003/0205681 A1 | 11/2003 | Modlin |
| 2003/0236458 A1 | 12/2003 | Hochman |
| 2004/0126005 A1 | 7/2004 | Duvdevani et al. |
| 2005/0019842 A1 | 1/2005 | Prober et al. |
| 2005/0030541 A1 | 2/2005 | Erlbacher et al. |
| 2005/0153435 A1 | 7/2005 | Archibald |
| 2005/0237605 A1 | 10/2005 | Vodyanoy et al. |
| 2006/0006067 A1 | 1/2006 | Unger |
| 2006/0043301 A1 | 3/2006 | Mantele et al. |
| 2006/0119852 A1 | 6/2006 | Shimizu |
| 2006/0166305 A1 | 7/2006 | Jiang et al. |
| 2006/0184040 A1 | 8/2006 | Keller et al. |
| 2006/0215400 A1 | 9/2006 | Lewis et al. |
| 2007/0035818 A1 * | 2/2007 | Bahatt .................. G01N 21/253 |
| | | 359/366 |
| 2007/0146717 A1 | 6/2007 | Prins et al. |
| 2007/0146870 A1 | 6/2007 | Metzger |
| 2008/0186494 A1 | 8/2008 | Kiesel et al. |
| 2008/0193930 A1 | 8/2008 | Ornatsky et al. |
| 2009/0051901 A1 | 2/2009 | Shen et al. |
| 2009/0170149 A1 | 7/2009 | Viator et al. |
| 2009/0190822 A1 * | 7/2009 | Ortyn .................. G01J 3/2889 |
| | | 382/134 |
| 2010/0014158 A1 | 1/2010 | Nihoshi |
| 2010/0128256 A1 | 5/2010 | Thomson |
| 2011/0064628 A1 | 3/2011 | Thomas et al. |
| 2011/0242535 A1 | 10/2011 | Frose |
| 2012/0326055 A1 | 12/2012 | Wilson et al. |
| 2013/0088221 A1 | 4/2013 | Van et al. |
| 2014/0030737 A1 | 1/2014 | Holmes et al. |
| 2014/0038206 A1 | 2/2014 | Holmes et al. |
| 2014/0193892 A1 | 7/2014 | Mohan et al. |
| 2014/0273188 A1 | 9/2014 | Mohan et al. |
| 2015/0031051 A1 | 1/2015 | Mohan et al. |
| 2015/0054979 A1 | 2/2015 | Ou et al. |
| 2015/0071541 A1 | 3/2015 | Qutub et al. |
| 2017/0023478 A1 | 1/2017 | Holmes et al. |
| 2017/0115289 A1 * | 4/2017 | Holmes .................. G01N 21/17 |
| 2017/0146447 A1 | 5/2017 | Mohan |
| 2017/0318216 A1 | 11/2017 | Gladnick et al. |
| 2017/0363851 A1 | 12/2017 | Xu et al. |
| 2018/0259764 A1 | 9/2018 | Watanabe |

FOREIGN PATENT DOCUMENTS

| | | |
|---|---|---|
| JP | 2006162427 A | 6/2006 |
| JP | 2007127449 A | 5/2007 |
| JP | 2010091679 A | 4/2010 |
| JP | 2010091809 A | 4/2010 |
| JP | 2011118264 A | 6/2011 |
| TW | 201224425 A | 6/2012 |
| WO | 2002093141 A1 | 11/2002 |
| WO | 2009142312 A1 | 11/2009 |
| WO | 2012119243 A2 | 9/2012 |
| WO | 2012178069 A | 12/2012 |
| WO | 2014018805 A2 | 1/2014 |
| WO | 2014127372 A2 | 8/2014 |

OTHER PUBLICATIONS

Office Action dated Jul. 8, 2015 for U.S. Appl. No. 13/951,063.
Office Action dated Jun. 12, 2015 for U.S. Appl. No. 14/161,639.
Office Action dated Jun. 5, 2015 for U.S. Appl. No. 14/508,137.

(56) References Cited

OTHER PUBLICATIONS

Handoo et al. Tissue flow cytometry in haematological diagnosis. Chapter 41:1-10 International Journal of Laboratory Hematology (Jun. 2012).
Notice of Allowance dated Aug. 10, 2016 for U.S. Appl. No. 14/161,639.
Office Action dated Sep. 22, 2016 for U.S. Appl. No. 14/167,964.
Office Action dated Sep. 9, 2016 for U.S. Appl. No. 14/508,137.
International Search Report and Written Opinion dated Sep. 11, 2014 for Application No. PCT/US2014/016962.
The International Search Report and the Written Opinion dated Mar. 24, 2014 for Application No. PCT/US2013/052141.
Office Action dated May 6, 2015 for U.S. Appl. No. 13/951,449.
Advisory Action dated Apr. 28, 2016 for U.S. Appl. No. 13/951,063.
Advisory Action dated Jul. 26, 2016 for U.S. Appl. No. 14/508,137.
Notice of Allowance dated Jun. 23, 2016 for U.S. Appl. No. 13/951,063.
Office Action dated May 12, 2016 for U.S. Appl. No. 14/508,137.
Office Action dated Sep. 21, 2015 for U.S. Appl. No. 14/508,137.
Office Action dated Jan. 4, 2016 for U.S. Appl. No. 14/161,639.
Office Action dated Nov. 5, 2015 for U.S. Appl. No. 13/951,449.
510(k) Substantial Equivalence Determination Decision Summary dated Jul. 16, 2015 for "Theranos Herpes Simplex Virus-1 (HSV-1) IgG Assay".
510(k) Substantial Equivalence Determination issued for "Theranos Herpes Simplex Virus-1 IgG Assay" by the FDA on Jul. 7, 2015.
Advisory Action dated Feb. 8, 2016 for U.S. Appl. No. 13/951,449.
Dhawan et al. Multispectral Optical Imaging of Skin-Lesions for Detection of Malignant Melanomas. Proceeding of the 31st Annual International Conference of the IEEE Engineering in Medicine and Biology Society: Engineering the Future of Biomedicine, EMBC 2009, IEEE, Sep. 3, 2009, pp. 5352-5355.
Diamandis. Theranos phenomenon: promises and fallacies. Clin Chem Lab Med. Jun. 2015;53(7):989-93.
Fuller K. Centers for Medicare and Medicaid Services (CMS). Condition Level Deficiencies Notice—Immediate Jeopardy. Notice to Theranos, Inc. director Dr. Sunil Dhawan. Jan. 25, 2016. https://cdn2.vox-cdn.com/uploads/chorus_asset/file/5969923/Theranos_Inc_Cover_Letter_01-25-2016.0.pdf.
Lee et al. Integrated optical molecular imaging system for four-dimensional real-time detection in living single cells, Biosensors and Bioelectronics, Elsevier BV, NL, vol. 31 No. 1, Oct. 27, 2011, pp. 393-398.
Loria K. More skeptical than ever: Experts respond to the government's warning letter to Theranos. Jan. 28, 2016. Tech Insider. http://www.techinsider/io/how-bad-the-cms-letter-to-theranos-really-is-2016-1.
Notice of Allowance dated Mar. 25, 2016 for U.S. Appl. No. 13/951,449.
Notice of Allowance dated Apr. 14, 2016 for U.S. Appl. No. 14/161,639.
Office Action dated Jan. 15, 2016 for U.S. Appl. No. 14/508,137.
Office Action dated Feb. 24, 2016 for U.S. Appl. No. 13/951,063.
Plebani. Evaluating and using innovative technologies: a lesson from Theranos? Clin Chem Lab Med. Jun. 2015;53 (7):961-2.
Ramsey L. Theranos has a week to respond to the searing report about its business. Business Insider. Feb. 5, 2016. http://www.businessinsider.com/theranos-response-to-cms-2016-2.
Rappleye E. Theranos gets extension to fix issues following CMS investigation. Becker's Hospital Review. Feb. 8, 2016. http://www.beckershospitalreview.com/hospital-management-adminstration/theranos-gets-extension-to-fix-issues-following-cms-investigation.html.
Thompson, Fluorescence Correlation Spectroscopy, Topics in Fluorescence Spectroscopy, Jan. 1, 2002, Kluwer Academic Publishers, Boston.
Office Action dated Oct. 6, 2017 for U.S. Appl. No. 14/630,544.
Office Action dated Mar. 2, 2017 for U.S. Appl. No. 14/508,137.
Office Action dated Mar. 30, 2017 for U.S. Appl. No. 15/340,637.
Office Action dated Jun. 20, 2017 for U.S. Appl. No. 14/167,964.
Office Action dated Feb. 9, 2018 for U.S. Appl. No. 15/340,637.
Office Action dated Jun. 28, 2018 for U.S. Appl. No. 15/184,923.
Office Action dated Jun. 5, 2018 for U.S. Appl. No. 14/508,137.
Office Action dated Jul. 30, 2018 for U.S. Appl. No. 15/278,333.
Office Action dated Aug. 15, 2018 for U.S. Appl. No. 15/340,637.
Office Action dated Mar. 18, 2019 for U.S. Appl. No. 15/278,333.
Office Action dated May 30, 2019 for U.S. Appl. No. 15/340,637.
Office Action dated Jul. 8, 2019 for U.S. Appl. No. 15/664,580.

* cited by examiner

Scatter

CD14- Pac Blue for Monocytes

CD123-PECy5 for Basophils

CD16-PE for Neutrophils

CD45-AF647 for all leukocytes

Draq5 as a nuclear stain

IMAGE ANALYSIS AND MEASUREMENT OF BIOLOGICAL SAMPLES

BACKGROUND

Analysis of biological samples from a subject may be important for health-related diagnosing, monitoring and/or treating of the subject. A variety of methods are known for the analysis of biological samples. However, in order to provide better diagnosing, monitoring, and/or treating of subjects, improvements in the analysis of biological samples are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Methods, devices, systems, and apparatuses described herein are useful for optical and image analysis and/or measurement of biological samples.

Embodiments disclosed herein include sample holders suitable for holding samples, including biological samples, for optical examination, for optical measurement, and for other examinations and measurements. In embodiments, a sample holder having an optically transmissive portion and a portion configured to provide internal reflection of light within the sample holder is provided. In embodiments, internal reflections may include partial internal reflection and may include total internal reflection of light. Incident light from an external light source, and directed from one side of the sample holder, is effective to illuminate a sample within the sample holder from a plurality of directions. In embodiments, an external light source disposed on one side of the sample holder may provide epi-illumination of a sample within the sample holder; may provide trans-illumination of a sample within the sample holder; and/or may provide both epi-illumination and trans-illumination of a sample within the sample holder.

Embodiments disclosed herein include systems including sample holders suitable for holding samples. Such systems are suitable for use in examining and measuring samples, including biological samples, by, e.g., optical examination, optical measurement, and for other examinations and measurements. In embodiments, a system disclosed herein comprises a sample holder having an optically transmissive portion and a portion configured to provide internal reflection of light within the sample holder is provided. In embodiments, internal reflections within a sample holder of a system disclosed herein may include partial internal reflection and may include total internal reflection of light. Systems disclosed herein may include light sources. Incident light from a light source external to a sample holder, and directed from one side of the sample holder, is effective to illuminate a sample within the sample holder from a plurality of directions. In embodiments, a light source disposed external to, and on one side of, the sample holder may provide epi-illumination of a sample within the sample holder; may provide trans-illumination of a sample within the sample holder; and/or may provide both epi-illumination and trans-illumination of a sample within the sample holder. Systems disclosed herein may include a detector, or detectors; such detectors may include optical detectors, and may include other detectors. Such detectors are suitable for, and are configured to, make measurements of a sample and of objects and characteristics of a sample and objects in a sample within a sample holder; such measurements may include qualitative measurements and quantitative measurements. Embodiments of systems as disclosed herein may include filters, apertures, gratings, lenses, and other optical elements. Embodiments of systems as disclosed herein may include mechanical apparatus for locating, moving, and adjusting a sample holder, a light source, a lens, a filter, or other element or component of a system as disclosed herein. Embodiments of systems as disclosed herein may include components and elements for transferring, aliquotting, holding, heating, mixing, staining, conditioning, or otherwise preparing, manipulating or altering a sample. Embodiments of systems as disclosed herein may include components and elements for transporting, securing, filling, or otherwise manipulating a sample holder. Embodiments of systems as disclosed herein may include components and elements for physical manipulation and treatment of a sample, and for physical manipulation of a sample holder, where such components and elements may include, without limitation, a pipette, a pump, a centrifuge, other mechanical apparatus for moving and manipulating a sample, a sample holder, pipette tips, vessels, and reagents for use with a sample, or portion thereof. Embodiments of systems as disclosed herein may include components and elements for chemical analysis, including nucleic acid analysis, protein analysis, general chemistry analysis, electrochemical analysis, and other analyses of a sample or portion thereof.

Sample holders and systems disclosed herein may be used, and methods disclosed herein may be performed, at any location, including a clinical laboratory, a research laboratory, a clinic, a hospital, a doctor's office, a point of service location, and any other suitable location. Samples held by sample holders disclosed herein, and samples examined using systems and methods disclosed herein, include any biological sample, and may be small biological samples. In embodiments, a sample may be a small blood or urine sample, and may have a volume of less than about 250 µL, or less than about 150 µL, or less than about 100 µL, or less than about 50 µL, or less than about 25 µL, or less than about 15 µL, or may be the same as or less than the volume of blood obtained from a finger-stick.

In one embodiment, a method for the measurement of a component of interest in cells of a cellular population in a sample is provided, including: a) obtaining a quantitative measurement of a marker present in cells of the cellular population in the sample; b) based on the measurement of part a), determining, with the aid of a computer, an approximate amount of cells in the cellular population present in the sample; c) based on the results of part b), selecting an amount of reagent to add to the sample, wherein the reagent binds specifically to the component of interest in cells of the cellular population and is configured to be readily detectable; d) based on the results of part c), adding the selected amount of the reagent to the sample; e) assaying cells in the sample for reagent bound to the component of interest; and f) based on the amount of reagent bound to the component of interest, determining the amount of the component of interest in cells of the cellular population of the sample. In an embodiment of the method, the reagent of part c) is an antibody.

Applicants further disclose herein a method for the measurement of a component of interest in cells of a cellular population in a sample, comprising: a) obtaining a quantitative measurement of a marker present in cells, or of a property of cells, of the cellular population in the sample; b) determining, with the aid of a computer, an approximate amount of cells in the cellular population present in the sample based on the measurement of part a); c) adding an amount of a cell marker to the sample, where the amount of said cell marker added is based on the results of part b), and wherein the cell marker binds specifically to the component of interest in cells of the cellular population and is configured to be readily detectable; d) assaying cells in the sample for marker bound to the component of interest; and e) determining the amount of the component of interest in cells of the cellular population of the sample based on the amount of marker bound to the component of interest.

In another embodiment, a method for focusing a microscope is provided, including: a) mixing a sample containing an object for microscopic analysis with a reference particle having a known size, to generate a mixture containing the sample and reference particle; b) positioning the mixture of step a) into a light path of a microscope; c) exposing the mixture of step a) to a light beam configured to visualize the reference particle; and d) focusing the microscope based on the position of the reference particle within the mixture, or based on the sharpness of the image of the reference particle.

In yet another embodiment, provided herein is a method for identifying a cell in a sample containing a plurality of cells, including: a) assaying a cell of the plurality of cells for at least one of: (i) the presence of a cell surface antigen; (ii) the amount of a cell surface antigen; or (iii) cell size; b) assaying the cell of a) for at least one of: (i) nuclear size; or (ii) nuclear shape; and c) assaying the cell of a) and b) for quantitative cell light scatter, wherein the combination of information from steps a), b) and c) is used to identify the cell in the sample containing a plurality of cells.

In yet another embodiment, provided herein is a system comprising a detector assembly for use with a sample holder that holds a sample to be examined. In one non-limiting example, the sample holder is a cuvette that has features and/or materials in it that enable the cuvette to be engaged and moved from one location to the detector assembly. In some embodiments, the detector assembly has a first surface that is configured to engage a surface of the sample holder in a manner such that the interface between the two does not create optical interference in the optical pathway from the detector assembly to the sample in the sample holder. In one embodiment, there may be more than one location on the detector assembly for one or more of the sample holders. Some embodiments may have the same sample holder for each of the locations. Optionally, some embodiments may have different sample holders for at least some of the locations associated with the detector assembly.

In one embodiment described herein, a sample holder is provided herein such as but not limited to a cuvette with optical properties, dimensions, materials, and/or physical features that allow for it to hold the sample for analysis by the detector assembly while keeping it physically separate from and not in direct contact with the detector assembly. This can be particularly useful for sample fluids that contain shaped members therein.

In one embodiment described herein, the detector assembly may be a multi-channel microscopy unit that is configured to detect, obtain, or measure the shape, and physical, optical, and biochemical properties of a cell or cells in a sample, all in the same device. It can provide both quantitative information, and descriptive information. One embodiment of the detector assembly may use multiple markers of the same color or wavelength, where the detector assembly is configured to deconvolute signals originating from such markers in a sample (e.g., bound to cells in a sample), allowing for a reduction in number of spectral channels and light sources required in the assembly.

It should be understood that some embodiments herein may include a sample holder such as but not limited to a cuvette with physical features in the shape of the cuvette material that increase darkfield illumination where some features are configured to provide for light reflectance (including, but not limited to, reflectance of light within the cuvette), and some features may optionally be configured for mechanical support; in embodiments, some features may provide mechanical support and also provide for light reflectance. In embodiments, a sample holder is configured to provide trans-illumination of a sample by reflection of light within the sample holder. In embodiments, a sample holder is configured to provide trans-illumination of a sample by reflection of light within the sample holder; such reflectance may include partial internal reflection (PIR), and such reflectance may include total internal reflectance (TIR). In embodiments, a sample holder is configured to provide trans-illumination of a sample by reflection of light within the sample holder, wherein the source of the reflected light is disposed on the same side of the sample holder as the optics used to detect or measure the light (i.e., the light source is an epi-illumination light source).

The system herein can simultaneously use both epi (direct) and trans (reflected) illumination in darkfield imaging. This differs from traditional darkfield imaging which uses either epi-illumination, or trans-illumination, but not both types of illumination, and not both types of illumination from a single source or single direction or location. Thus, the combination of epi- and trans-illumination disclosed herein, wherein the trans-illumination originates from the same light source as the epi-illumination, differs from known systems. Optionally, the use of a shaped sample holder such as the cuvette can be used to provide the trans-illumination. In embodiments, a shaped sample holder is configured to provide trans-illumination by reflection of light. In embodiments, a shaped sample holder is configured to provide trans-illumination by reflection of light within the sample holder. In embodiments, one or more of the size, shape, surface, materials, or other feature of a shaped sample holder is effective to provide internal reflection of light within the shaped sample holder. In embodiments, one or more of the size, shape, surface, materials, or other feature of a shaped sample holder is effective to provide partial internal reflection (PIR) of light within the shaped sample holder. In embodiments, one or more of the size, shape, surface, materials, or other feature of a shaped sample holder is effective to provide total internal reflection (TIR) of light within the shaped sample holder. Optionally, the intensity of trans-illumination is non-negligible. In embodiments, a shaped sample holder may include a reflective surface effective to increase trans-illumination light intensity. The dark field light source may be a light-emitting diode (LED), laser, or other illumination source that can provide the desired illumination and/or excitation wavelength(s).

In one embodiment, the combination of the microscope objective and light source such as but not limited to a ringlight (for darkfield microscopy) is at a physical distance between them that enables a compact size for the detector assembly. In one embodiment, only light at a desired wavelength or within a desired range of wavelengths are directed to the sample. In one embodiment, the light is non-polarized light. In another embodiment, the light is polarized light.

In yet another embodiment, information from the cytometry assay, either from the sample preparation phase and/or from the analysis phase, is used to guide and/or trigger a secondary procedure. In embodiments, such a secondary procedure may be to provide an alert for direct human review. In embodiments, such a secondary procedure may be to use an estimated cell count or other information obtained during a sample preparation step of a procedure in order to guide the performance of an assay, where such assay may be an assay in a later step of the procedure, or may be an assay in another procedure.

Techniques for counting cells can also provide ways to deal with sample holders with uneven shapes and/or chamber surfaces. One method comprises using: a) a volume-metered channel technique to introduce a known volume of a sample into an analysis area, such as a channel in the sample holder. The method may include counting all cells in the sample holder. Since one knows the volume of sample, one also knows the concentration of cells in volume (this may be performed in hydrophobic containers or cuvettes or sample holders with chambers with such surfaces). Another method comprises: b) a ratio-based metric technique to mix sample with a known amount of beads, which is used to calculate the concentration of cells in the sample based on the number of beads observed.

In yet another embodiment described herein, a method is provided comprising measuring formed blood components such as but not limited to measuring red blood cell (RBC) volume in a blood sample by causing the RBCs to assume substantially spherical shapes, and measuring the RBC volume using darkfield microscopy.

In yet another embodiment described herein, a method is provided comprising measuring platelet volume. The method may include labeling platelets with a fluorescent dye and measuring the size of the platelets observed; adding beads of known size to the sample; and comparing the observed size of images of the beads to the observed images of the platelets, using the beads as calibration to determine the size of the platelets and to determine the platelet volume in the sample.

In yet further embodiments described herein, methods are provided for detecting and measuring, in a sample, cell morphology; measurement of cell numbers; detection of particles; measurement of particle numbers; detection of crystals; measurement of crystal numbers; detection of cell aggregates; measurement of numbers of cell aggregates; and other properties and quantities of or in a sample.

Accordingly, Applicants disclose herein:

A system for analyzing a sample, the system comprising: a sample holder comprising a sample chamber configured to hold said sample, at least a portion of said sample holder comprising an optically transmissive material, said optically transmissive material comprising an optically transmissive surface and a reflective surface; and an illumination source configured to provide light that illuminates and passes through said optically transmissive surface; wherein said sample holder is configured effective that said light from said illumination source simultaneously provides both epi-illumination and trans-illumination to a sample in the sample holder, where epi-illumination comprises light traveling from said illumination source to said sample without reflection at a surface of the optically transmissive material of the sample holder, and where trans-illumination comprises light traveling within the optically transmissive material and to the sample following at least one reflection from at least one surface of said optically transmissive material. In embodiments, a sample holder of a system having the features disclosed herein may comprise a cuvette having an elongated channel configured for holding a sample. In embodiments, the sample holder may have one or more optically non-transmissive surfaces.

In embodiments of systems disclosed herein, said trans-illumination may be provided at least in part by internal reflection of light at a surface, and may be provided at least in part by total internal reflection of light within the cuvette. In embodiments of systems disclosed herein, said trans-illumination may be provided at least in part by partial internal reflection of light at a surface, and may be provided at least in part by partial internal reflection of light within the cuvette.

In embodiments, a sample holder may have two or more sample chambers for holding sample. A sample holder, e.g., a cuvette, having feature disclosed herein may have a rectangular horizontal, cross-sectional shape; may have a circular horizontal, cross-sectional shape; may have a saw tooth vertical cross-sectional shape; may have a step-shaped vertical cross-sectional shape; or may have another shape.

In embodiments, a sample holder may be movable relative to an illumination source, and may be movable to a plurality of locations, wherein an optically transmissive surface of the sample holder may be illuminated by the illumination source at each location.

In embodiments, an illumination source may include a ringlight. In embodiments, a ringlight may be selected from a light emitting diode (LED)-based ringlight and a laser-based ringlight.

In embodiments, a system as disclosed herein may include a support structure having an optically transmissive surface shaped to engage an optically transmissive surface of the sample holder.

In embodiments, a system as disclosed herein may have a compression device configured to retain the sample holder in a desired location for illumination by the illumination source.

In embodiments, a system as disclosed herein may include a detector configured to image at least a portion of a channel in the sample holder.

In embodiments, a sample holder as disclosed herein may include an elongated channel configured to contain at least a portion of the sample, and wherein a detector is configured to image an entire elongated channel in the sample holder.

In embodiments, a sample holder as disclosed herein may be configured to hold the sample in a static, non-flowing manner during imaging; in embodiments, a sample holder may be configured to hold one portion of the sample in a static, non-flowing manner and another portion in a flowing manner.

In embodiments, an illumination source as disclosed herein may be movable relative to the sample holder.

In embodiments, a sample holder as disclosed herein may be configured to hold the sample in a flowing manner during imaging.

In embodiments, a sample holder as disclosed herein may include a fluid circuit fully confined in the sample holder, and wherein the sample is located in said fluid circuit, effective that the sample remains separate from said detector.

In embodiments, a sample holder as disclosed herein is movable relative to the detector. In embodiments, a detector as disclosed herein is movable relative to the sample holder.

In embodiments, a sample holder and an illumination source as disclosed herein comprise at least part of an optical analysis unit, and the system further includes a clinical analysis unit configured to perform clinical analysis on a sample.

In embodiments, a system as disclosed herein is configured to provide an aliquot of a single sample to an optical analysis unit and to a clinical analysis unit, effective that the clinical analysis unit and the optical analysis unit may perform optical analysis and clinical analysis on portions of a sample at the same time. In embodiments, such a clinical analysis may be selected from general chemical analysis, nucleic acid analysis, and enzyme-linked binding analysis.

In embodiments, a system as disclosed herein may include a plurality of clinical analysis units, wherein each of such clinical analysis units is configured to provide a clinical analysis selected from general chemical analysis, nucleic acid analysis, and enzyme-linked binding analysis.

Applicants further provide a cuvette comprising a sample chamber configured to hold a sample, at least a portion of said cuvette comprising an optically transmissive material, said optically transmissive material comprising an optically transmissive surface and a reflective surface, wherein said optically transmissive surface and said reflective surface are configured effective that light passing through the optically transmissive surface simultaneously provides both epi-illumination and trans-illumination to said sample in the sample chamber, where epi-illumination comprises light traveling from said illumination source to the sample without reflection at a surface of the optically transmissive material, and where trans-illumination comprises light traveling within the optically transmissive material and to the sample following at least one reflection from at least one surface of said optically transmissive material.

In embodiments, a cuvette as disclosed herein has a sample chamber comprising an elongated channel. In embodiments, a cuvette as disclosed herein comprises two or more sample chambers for holding sample.

In embodiments, a cuvette as disclosed herein may have one or more optically non-transmissive surfaces.

In embodiments, trans-illumination may be provided in a cuvette as disclosed herein, at least in part by internal reflection of light within the cuvette. In embodiments, trans-illumination may be provided in a cuvette as disclosed herein, at least in part by partial internal reflection of light at a surface of the cuvette. In embodiments, trans-illumination may be provided in a cuvette as disclosed herein, at least in part by total internal reflection of light at a surface of the cuvette.

In embodiments, a cuvette as disclosed herein may have a rectangular horizontal, cross-sectional shape; in embodiments, a cuvette as disclosed herein may have a circular horizontal, cross-sectional shape. In embodiments, a cuvette as disclosed herein may have a saw tooth vertical cross-sectional shape; in embodiments, a cuvette as disclosed herein may have a step-shaped vertical cross-sectional shape.

Applicants disclose methods herein. For example, Applicants disclose herein a method of identifying a cell in a sample containing a plurality of cells, comprising: (a) placing said sample in a sample holder comprising a sample chamber configured to hold the sample, at least a portion of said sample holder comprising an optically transmissive material, said optically transmissive material comprising an optically transmissive surface and a reflective surface, wherein said optically transmissive surface and said reflective surface are configured effective that light passing through the optically transmissive surface simultaneously provides both epi-illumination and trans-illumination to the sample in the sample chamber, where epi-illumination comprises light traveling from said illumination source to the sample without reflection at a surface of the optically transmissive material, and where trans-illumination comprises light traveling within the optically transmissive material and to the sample following at least one reflection from at least one surface of said optically transmissive material; (b) illuminating said sample holder effective to simultaneously provide both epi-illumination and trans-illumination of the sample; and (c) identifying a cell in the sample. In embodiments, methods disclosed herein include methods wherein said identifying comprises identifying said cell with a detector configured to image at least a portion of said sample chamber. In embodiments disclosed herein, a sample chamber for use in such methods may comprise an elongated channel.

Applicants further disclose herein a method for focusing a microscope, comprising: a) mixing a sample containing an object for microscopic analysis with a reference particle having a known size, effective to generate a mixture containing the sample and reference particle; b) positioning the mixture of step a) into a light path of a microscope; c) exposing the mixture of step a) to a light beam configured to visualize the reference particle; and d) focusing the microscope based on the position of the reference particle within the mixture or based on the sharpness of an image of the reference particle.

Applicants disclose herein a method of identifying a cell in a sample containing a plurality of cells, comprising: (a) assaying a cell of the plurality of cells for at least one of: (i) the presence of a cell surface antigen; (ii) the amount of a cell surface antigen; or (iii) cell size; (b) assaying the cell of (a) for at least one of: (i) nuclear size; or (ii) nuclear shape; and (c) assaying the cell of (a) and (b) for quantitative cell light scatter, wherein the combination of information from steps (a), (b), and (c) is used to identify the cell in the sample containing a plurality of cells.

In at least one embodiment described herein, a system for imaging a sample, the system comprising: a sample vessel containing said sample, a stage having a sample vessel receiver with an optically transparent surface; a light source for illuminating formed components in the sample through the stage, wherein the sample vessel has an interface surface configured to engage the optically transparent surface of the sample vessel receiver whereby the interface surface conforms to the optically transparent surface without significant distortion of light passing through the interface surface.

It should be understood that embodiments herein may be configured to include one or more of the following features. For example, the interface surface of the sample vessel may be formed from a polymer material. Optionally, this may be a transparent material. Optionally, the interface surface of the sample vessel is formed of a material softer than a material used to form the optically transparent surface of the sample vessel receiver. Optionally, a compression unit is provided for applying pressure to conform the interface surface to a shape configured to conform with the optically transparent surface of the sample vessel receiver. Optionally, a handling unit may be configured to be coupled to the sample vessel to facilitate transport of sample vessel on and off the stage, and increase mechanical rigidity of the sample vessel. Optionally, the handling unit may be an optically opaque unit configured to be coupled to the sample vessel. Optionally, the handling unit may be formed with physical features, protrusions, or the like to facilitate engagement with a robotic manipulator, pipette unit, or other mechanical mover. Optionally, the handling unit may be formed with magnetic, electromagnetic, or other features to facilitate engagement and/or disengagement. Optionally, all imaging of the sample may be done without passing light in a substantially straight line through one surface and out an opposing surface to a detector. Optionally, the light source is not located on one side of the sample vessel to deliver light to a detector on an opposite side of the sample vessel.

It should be understood that embodiments in this disclosure may be adapted to have one or more of the features described in this disclosure.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 9A is a dark-field image; FIG. 9B is an image showing fluorescence from labeled anti-CD14 antibodies attached to monocytes; FIG. 9C is an image showing fluorescence from labeled anti-CD123 antibodies attached to basophils; FIG. 9D is an image showing fluorescence from labeled anti-CD16 antibodies attached to neutrophils; FIG. 9E is an image showing fluorescence from labeled anti-CD45 antibodies attached to leukocytes; FIG. 9F is an image showing leukocyte and platelet cells stained with nuclear stain DRAQ5® (red blood cells, lacking nuclei, are not stained by DRAQ5®).

FIG. 11A shows identification of monocytes by plotting CD14 label intensity (FL-17) versus scatter intensity (FL-9). FIG. 11B shows identification of basophils by plotting CD123 intensity (FL-19) versus CD16 intensity (FL-15). FIG. 11C shows identification of lymphocytes by plotting CD16 intensity (FL-15) versus CD45 intensity (FL-11). FIG. 11D shows identification of neutrophils and eosinophils by plotting CD16 intensity (FL-15) versus scatter intensity (FL-9).

FIG. 12A plots white blood cell counts obtained by the present methods versus white blood cell counts obtained by the commercial blood analyzer. FIG. 12B plots red blood cell counts obtained by the present methods versus red blood cell counts obtained by the commercial blood analyzer. FIG. 12C plots platelet counts obtained by the present methods versus platelet counts obtained by the commercial blood analyzer. FIG. 12D plots neutrophil counts obtained by the present methods versus neutrophil counts obtained by the commercial blood analyzer. FIG. 12E plots monocyte counts obtained by the present methods versus monocyte counts obtained by the commercial blood analyzer. FIG. 12F plots lymphocyte counts obtained by the present methods versus lymphocyte counts obtained by the commercial blood analyzer.

DETAILED DESCRIPTION

Figure 1A:
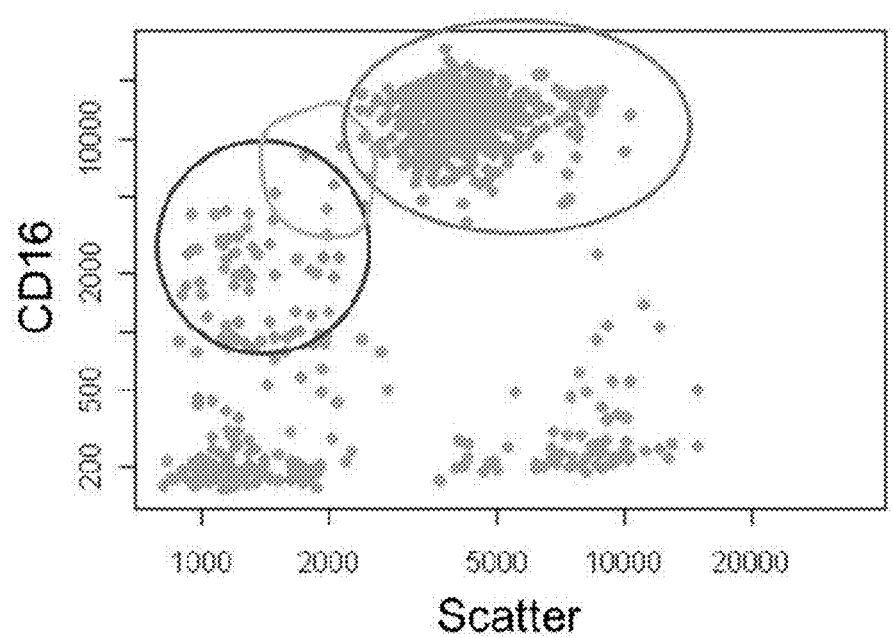
FIG. 1A shows a plot of side scatter intensity (x-axis) vs. fluorescence intensity of a mixture cells including natural killer cells and neutrophils labeled with a fluorescent binder that recognizes CD16.

Description and disclosure which may aid in understanding the full extent and advantages of the devices, systems, and methods disclosed herein may be found, for example, in U.S. Pat. Nos. 7,888,125; 8,088,593; 8,158,430; 8,380,541; U.S. patent application Ser. No. 13/769,798, filed Feb. 18, 2013; U.S. Patent Application Ser. No. 61/802,194, filed Mar. 15, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, greater than about 30%, greater than about 40%, or greater than about 50% as a function of the reference value or comparator value.

As used herein, "internal reflection" refers to reflection of light, within a material (the first material), at a boundary between the first material and another material (the second material). For example, a first material may be a solid such as a glass or plastic, and the second material may be, e.g., air. The light that is internally reflected is traveling within the first material before it is reflected. Internal reflection may be partial (partial internal reflection: PIR) or total (total internal reflection: TIR). Thus, internal reflection where all of the light incident at a surface is reflected back within the first material is TIR, while internal reflection where not all light incident at a surface is reflected within a material is PIR. (With PIR, some light may pass through the boundary, and some light is reflected at the surface back into the material.) The angle of the incidence is an important factor in determining the extent of internal reflection; it is the angle of an incident light ray measured versus a line perpendicular to the boundary surface. Whether or not TIR occurs depends upon the angle of incidence of the light with respect to the surface at the boundary between the first and the second material; the index of refraction of the first material; the index of refraction of the second material; and other factors (e.g., the wavelength of light may affect TIR since the index of refraction typically varies with wavelength). The angle at which light is totally internally reflected is termed the critical angle; incident light having an angle of incidence greater than the critical angle will be totally internally reflected (will remain within the material: TIR). However, with PIR, a portion of incident light having an angle of incidence less than the critical angle will also be internally reflected (the remaining light being refracted and passing out of the first material into the second material).

As used herein, a "sample" may be but is not limited to a blood sample, or a urine sample, or other biological sample. A sample may be, for example, a blood sample (e.g., a sample obtained from a finger-stick, or from venipuncture, or an arterial blood sample, and may be whole blood, serum, plasma, or other blood sample), a urine sample, a biopsy sample, a tissue slice, stool sample, or other biological sample; a water sample, a soil sample, a food sample, an air sample; or other sample (e.g., nasal swab or nasopharyngeal wash, saliva, urine, tears, gastric fluid, spinal fluid, mucus, sweat, earwax, oil, glandular secretion, cerebral spinal fluid, tissue, semen, cervical fluid, vaginal fluid, synovial fluid, throat swab, breath, hair, finger nails, skin, biopsy, placental fluid, amniotic fluid, cord blood, lymphatic fluids, cavity fluids, sputum, mucus, pus, a microbiota sample, meconium, breast milk and/or other excretions).

Thus, as used herein, a "sample" includes a portion of a blood, urine, or other biological sample, may be of any suitable size or volume, and is preferably of small size or volume. In some embodiments of the systems, assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

In embodiments, the volume of sample collected via finger-stick may be, e.g., about 250 µL or less, or about 200 µL or less, or about 150 µL or less, or about 100 µL or less, or about 50 µL or less, or about 25 µL or less, or about 15 µL or less, or about 10 µL or less, or about 10 µL or less, or about 5 µL or less, or about 3 µL or less, or about 1 µL or less.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

The term "cells," as used in the context of biological samples, encompasses samples that are generally of similar sizes to individual cells, including but not limited to vesicles (such as liposomes), cells, virions, and substances bound to small particles such as beads, nanoparticles, or microspheres.

As used herein, the term "binds" refers to a reaction, or interaction, between two materials which lead to the close combination of the two; e.g., a reaction between a ligand and a receptor, in which the ligand becomes tightly linked to the receptor, provides an example of binding. The combination of an antibody with its target antigen, and of a carrier protein with its cargo, such as intrinsic factor with vitamin B12, are further examples of reactions in which one material binds to another.

The term "binder" as used herein refers generally to any compound or macromolecule, such as an antibody, which tightly or specifically binds to a target. Binders include, but are not limited to, antibodies (whether monoclonal or polyclonal, antibody fragments, immunoadhesins, and other such antibody variants and mimics), natural binding proteins (e.g., intrinsic factor protein which is specific for vitamin B12), ligands which bind their target receptors, substrates which bind to particular enzymes, binding pairs such as avidin and biotin, small molecules which tightly and specifically bind to target molecules, and the like. Bacteria, viruses, synthetic scaffolds, and other objects and materials that bind or adhere to specific targets may be used as binders. A binder may be, or may include, or may be linked to, a marker such as a dye, or fluorophore, or other detectable moiety.

As used herein, a "marker" is a detectable material whose presence makes a target visible or otherwise detectable, or whose presence in a position or location is indicative of the presence of a target in that position or location. A marker may be used to label a cell, structure, particle, or other target, and may be useful to detect, determine the presence of, locate, identify, quantify, or otherwise measure a target in, or property of, a sample. Markers may include, without limitation, stains, dyes, ligands, antibodies, particles, and other materials that may bind or localize to specific targets or locations; bacteria, viruses or cells that may grow in or localize to specific targets or locations may also be used as markers. Detectable attributes or properties of cells or other targets may be used as markers.

As used herein, the terms "stain" and "dye" may be interchangeable, and refer to elements, compounds, and macromolecules which render objects or components of a sample more detectable than in the absence of treatment with the stain or dye. For example, treatment of a blood sample with a DNA dye such as propidium iodide renders the nuclei of nucleated cells more visible, and makes detection and quantification of such cells easier than otherwise, even in the presence of non-nucleated cells (e.g., red blood cells).

As used herein, a "detector" may be any device, instrument, or system which provides information derived from a signal, image, or other information related to a target, such as a sample. Detectable signals and information may include, for example, optical, electrical, mechanical, chemical, physical, or other signals. A detector may be, for example, an optical detector, or an electrical detector, or a chemical detector, or an electrochemical detector, or an acoustic detector, or a temperature detector, or a mechanical detector, or other detector.

As used herein, an "optical detector" detects electromagnetic radiation (e.g., light). An optical detector may detect an image or be used with an image, or may detect light intensity irrespective of an image, or both. An optical detector may detect, or measure, light intensity. Some optical detectors may be sensitive to, or restricted to, detecting or measuring a particular wavelength or range of wavelengths. For example, optical detectors may include, for example, photodiode detectors, photomultipliers, charge-coupled devices, laser diodes, spectrophotometers, cameras, microscopes, or other devices which measure light intensity (of a single wavelength, of multiple wavelengths, or of a range, or ranges, of wavelengths of light), form an image, or both.

The term "ploidy" as used herein refers to the amount of DNA in a cell, and to assays and measurements of the DNA content of cells in a sample. Ploidy measurements provide a measure of whether or not a cell, or a population of cells, has a normal or an abnormal amount of DNA, or, since DNA is duplicated during cell division and proliferation, if abnormal numbers of cells in a population are proliferating. Ploidy measurements may be made by imaging techniques following staining of nucleated cells in a sample with a DNA-specific dye.

Quantitative Microscopy

In some embodiments, methods, systems, and devices are provided herein for quantitative microscopy. Quantitative microscopy may involve one or more of quantitative fluorescence microscopy, quantitative dark field microscopy, quantitative bright field microscopy, and quantitative phase contrast microscopy methods to measure one or more cellular attributes. Any of these methods may provide morphometric information regarding cells. Such information may be measured quantitatively. In some embodiments, for quantitative microscopy, a sample is analyzed by two or more of quantitative fluorescence microscopy, quantitative dark field microscopy, quantitative bright field microscopy, and quantitative phase contrast microscopy. Quantitative microscopy may include use of image analysis techniques and/or statistical learning and classification methods to process images obtained by microscopy.

Multiple different cellular attributes may be measured during quantitative microscopy. Cellular attributes that may be measured include, without limitation:

Physical attributes: e.g. cell size, volume, conductivity, low and high angle scatter, and density. Other physical attributes that may be measured and/or quantified include, without limitation, circularity of a cell or particle; aspect ratio of a cell or particle; perimeter of a cell or particle; convexity of a cell or particle; granularity of a cell or particle; intensity of an image of a cell or particle; height (e.g., size through several focal planes) of a cell or particle; flatness of a cell or particle; and other physical attributes.

Morphological attributes: e.g. cell shape, area, size, and lobularity; nucleus shape area, size, and lobularity; mitochondria shape, area, size, and lobularity; and ratio of nuclear volume to cell volume.

Intracellular attributes: e.g. nucleus centroid/cell centroid distance (i.e. distance between the center of the nucleus and the center of the cell), nucleus lobe centroid distance (i.e. distance between the center of different lobes of the nucleus), distribution of proteins within the cells (e.g. actin, tubulin, etc.), distribution of organelles within the cells (e.g. lysosomes, mitochondria, etc.), colocalization of proteins with other proteins and organelles, and other attributes.

Biochemical attributes: e.g. expression level of cellular proteins, cell surface proteins, cytoplasmic proteins, nuclear proteins, cellular nucleic acids, cell surface nucleic acids, cytoplasmic nucleic acids, nuclear nucleic acids, cellular carbohydrates, cell surface carbohydrates, cytoplasmic carbohydrates, and nuclear carbohydrates.

In some embodiments, methods, systems, and devices are provided herein for the quantitative measurement of two, three, four, five or more attributes of cells in a sample, wherein the attributes are selected from physical attributes, morphological attributes, intracellular attributes, and biochemical attributes. In some embodiments, methods, systems, and devices are provided herein for the quantitative measurement of two, three, four, five or more attributes of cells in a sample, wherein the attributes are selected from: cell size, cell volume, cell conductivity, cell low angle light scatter, cell high angle light scatter, cell density, cell shape, cell area, cell lobularity, nucleus shape, nucleus area, nucleus size, nucleus lobularity, mitochondria shape, mitochondria area, mitochondria size, mitochondria lobularity, ratio of nuclear volume to cell volume, nucleus centroid/cell centroid distance, nucleus lobe centroid distance, distribution of proteins with the cells (e.g. actin, tubulin, etc.), distribution of organelles within the cells (e.g. lysosomes, mitochondria, etc.), expression level of a cellular protein, expression level of a cell surface protein, expression level of a cytoplasmic protein, expression level of a nuclear protein, expression level of a cellular nucleic acid, expression level of a cell surface nucleic acid, expression level of a cytoplasmic nucleic acid, expression level of a nuclear nucleic acid, expression level of a cellular carbohydrate, expression level of a cell surface carbohydrate, expression level of a cytoplasmic carbohydrate, and expression level of a nuclear carbohydrate.

In some embodiments, methods are provided for the quantitative measurement of two, three, four, five, or more attributes of cells in a biological sample by microscopy, wherein the method may include one or more of the following steps or elements. The attributes of the cells quantitatively measured may be selected from the attributes listed in the immediately above paragraph. The biological sample may be pre-treated prior to microscopy. Pre-treatment may include any procedure to aid in the analysis of the sample by microscopy, including: treatment of the sample to enrich for cells of interest for microscopy, treatment of the sample to reduce components in the sample which may interfere with microscopy, addition of material to the sample to facilitate analysis of the sample by microscopy (e.g. diluents, blocking molecules to reduce non-specific binding of dyes to cells, etc.). Optionally, prior to microscopy, a sample may be contacted with one or more binders that specifically bind to a cellular component. Binders may be directly linked to a dye or other particle for the visualization of the binder. A sample may also be contacted with a secondary binder, which binds to the binder which binds to the cellular component. A secondary binder may be directly linked to a dye or other particle for the visualization of the binder. Prior to microscopy, a sample may be assayed in a spectrophotometer. For microscopy, a biological sample containing or suspected of containing an object for microscopic analysis may be introduced into a sample holder, such as a slide or a cuvette. The sample holder containing a sample may be introduced into a device configured to perform quantitative microscopy on the sample. The microscope may be coupled with an image sensor to capture images generated through the microscope objective. In the device, multiple images of the sample may be acquired by microscopy. Any one or more of quantitative fluorescence microscopy, quantitative dark field microscopy, quantitative bright field microscopy, and quantitative phase contrast microscopy may be used to obtain images of the sample. Optionally, images of the entire sample in the sample holder may be acquired by microscopy. Multiple fields of view of the microscope may be required to capture images of the entire sample in the sample holder. The sample holder may move relative to the microscope or the microscope may move relative to the sample holder in order to generate different field of views in order to examine different portions of the sample in the sample holder. Multiple images of the same field of view of the sample in the sample holder may be acquired. Optionally, multiple filters may be used with the same type of microscopy and the same field of view of the sample, in order to acquire different images of the same sample which contain different information relating to the sample. Filters that may be used include, without limitation bandpass and long pass filters. Filters may permit the passage of certain wavelengths of light, and block the passage of others. Optionally, multiple types of microscopy (e.g. fluorescence, dark field, bright field, etc.) may be used to acquire images of the same field of view of the sample, in order to acquire different images of the same sample which contain different information relating to the sample. Optionally, video may be used to collect microscopy images. Optionally, microscopy images may be collected in 3-D. For microscopy performed as described herein, the device or system may be configured to link information relating to a cell in one image of the sample to the same cell in a different image of the sample. Based on different images of the same sample and/or same cells, multiple attributes of cells in the sample may be determined. In some aspects, the combination of multiple attributes/multiple pieces of information about cells in a sample may be used to reach a clinical decision and/or to draw a conclusion about the cells that would not be possible based on information from only a single attribute of the cells.

In some embodiments, devices and systems are provided for the quantitative measurement of two, three, four, five, or more attributes of cells in a biological sample by microscopy. In some embodiments, the device or system contains both a microscope or cytometer and a spectrophotometer. The device or system may further contain a fluid handling apparatus, which is configured to move sample between a spectrophotometer and a microscope or cytometer. In some embodiments, devices and systems for performing the methods disclosed herein are configured as described in U.S. patent application Ser. No. 13/244,947 and U.S. patent application Ser. No. 13/769,779, which are each hereby incorporated by reference in their entireties. Although the foregoing has been described in the context of a cell, it should also be understood that some or all of the foregoing may also be applied to crystals, particles, filaments, or other cell-sized objects that may be found in a sample.

Dynamic Dilution

In some embodiments, methods, systems, and devices are provided herein for dynamic dilution of cell-containing samples.

By way of non-limiting example, a method for dynamic dilution of a sample may include one or more of the following steps or elements such that a desired number or concentration of cells or objects in the sample is determined and this information is used as a factor in adjusting downstream sample processing. In this non-limiting example, one or more stains or dyes may be added to a biological sample containing cells. The mixture of stain and sample may be incubated. The cells in the mixture of stain and sample may be washed to remove excess (unbound) stain. The stained, washed cells may be prepared in a desired volume for further analysis. The stained, washed cells may be analyzed to determine the approximate number or concentration of cells in the sample or a portion thereof. Based on the number or concentration of stained cells in the sample or portion thereof, a volume of sample may be obtained for further analysis, such that a desired number or concentration of cells for further analysis is obtained. In some embodiments, samples may be diluted as described in U.S. patent application Ser. No. 13/355,458, which is hereby incorporated by reference in its entirety.

In one embodiment as described herein, it is desirable to provide another detection technique such as but not limited to fluorescence-based method for enumerating cells, to estimate cell concentration in place of using a cell counter. This estimate is described because, for accurate and reproducible staining of patient samples, it is often desirable that stains (DNA dyes/antibodies/binders/etc.) are optimally titered for a specific number/concentration of cells. For example, a known concentration of stain will be applied to a specific number of cells (e.g. 0.2 micrograms of stain per one thousand white blood cells (WBCs)). After an incubation period, the sample will be washed to remove excess (unbound) dye, prepared at the appropriate cell density, and imaged.

In this non-limiting example, to make an estimate of cell concentration for a targeted cell type, a sample is non-destructively measured with a different modality from that used for cytometry, such as but not limited to a spectrophotometer, in order to inform sample processing for the cytometric assay. The method may comprise selecting another marker unique to the cell population of interest. In one non-limiting example, for B-cells, one may choose CD20. The process comprises labeling the sample with anti-CD20 binders conjugated to a different colored fluorophore than CD5. One then measures the fluorescent signal of this sample non-destructively and rapidly using a device such as but not limited to a fluorescence spectrophotometer. Using calibration, it is possible to predict the concentration of B-cells with limited accuracy to provide the estimate. In one non-limiting example, the calibration may correlate signal strength with the number of cells for that type of signal. The creation of these calibration curves can be used to estimate the number of cells or object. Other techniques for estimating number of cells based on an overall signal strength such as but not limited to optical, electrical, acoustical, or the like are not excluded. Based on the approximate concentration of B-cells, the system can estimate the appropriate amount and concentration of anti-CD5 binder so that proportional relationship between CD5 expression and CD5 fluorescence is maintained. In this manner, the stain and staining procedure can be optimized/normalized for a particular cell number.

To maximize the use of patient samples (which may be low volume samples, such as, e.g., blood obtained from a finger-stick, having a volume equal to or less than about 120 µL), it is desirable to develop methods whereby the number of WBCs contained within a given volume of blood can be enumerated (e.g., the concentration WBCs/µL determined). This allows the number of WBCs to be determined, or at least estimated, prior to adding stains. Once determined, a desired number of cells can be aliquotted for incubation with a known concentration of stain(s), yielding optimal resolution of cell subpopulations.

In an application where measurement of ploidy of cells is desired, cells in a sample may be stained with a DNA dye, and then the intensity of staining may be quantified (where "the intensity of staining" means the intensity of an optical signal due to the dye). The intensity of the dye signal due to such staining depends upon the ratio of DNA/dye (that is, of the amount of DNA stained by the dye to the amount of dye added). If a preset amount of dye is added to every sample, regardless of the characteristics of the sample, then samples with very high cell concentration will each be less bright as compared to samples with low cell concentration. This situation would confound the quantification of the amount of DNA in each cell. As disclosed herein, obtaining an estimate of the number of nucleated cells in a sample prior to adding the dye allows one to adjust the amount of dye so that quantification of the DNA, and of the amount of DNA per cell in the sample, may be performed. Thus, for example, a sample, or an aliquot of a sample, may be treated with a stain or dye directed at a cell-surface marker indicative of the cell or cells to be quantified, and that surface marker used to non-destructively estimate the concentration of cells in the sample. This estimated concentration may then be used to calculate the amount of dye that needs to be added to the sample so as to always maintain a consistent DNA:Dye ratio (mole to mole) for subsequent measurements.

In a first example of a fluorescence-based method for enumerating cells, a method may comprise determining the ploidy of cells (e.g., enumerating cells via fluorophore-conjugated antibody staining). In this non-limiting example, it is desired to enumerate the WBCs in a blood sample so that a specific number of WBCs can be stained with a predetermined concentration of DNA dye (e.g., 4'-6-diamidino-2-phenylindole (DAPI), or 1,5-bis {[2-(di-methyl-amino) ethyl]amino}-4,8-dihydroxyanthracene-9,10-dione (DRAQ5®), or propidium iodide, or other DNA-staining dye). The method of this example comprises counting WBCs using a fluorophore-conjugated antibody and a spectrophotometer. It should be understood that this approach may be helpful when staining cells with a DNA dye and determining ploidy, where the ratio of cell number to DNA dye concentration (cell #: [DNA dye]) is desirable for generating comparable and consistent data. Given that the number of cells per microliter of blood vary within a healthy population, it is typically desirable to determine the number of WBCs per microliter before attempting to stain for ploidy.

In an embodiment, the procedure comprises using cells that are first stained with a fluorophore-conjugated antibody (where the antibody is preferably directed to a ubiquitously expressed antigen, such as CD45, or to a subpopulation specific antigen, such as CD3 for T cells), or fluorescent dye which labels all cells (e.g., a membrane or cytoplasmic stain such as eosin, or a lectin or other stain or dye) where the wavelength of the fluorescence from the fluorophore is spectrally distinct (and preferably distant) from the emission wavelength of the DNA dye. After an incubation period, the sample is washed to remove excess (unbound) antibody, prepared in the appropriate volume, and analyzed via a spectrophotometer. The resulting data allows the numbers of WBCs in a blood sample to be determined, so that a specific volume of blood can be aliquotted (yielding a particular/desired number of WBCs) and stained with a DNA dye. The resulting data is useful to calculate and to adapt the amount of DNA dye to be used in staining a sample, according to the number of WBCs determined using the fluorophore-conjugated antibody as described.

A further embodiment comprises determining the number of cells (via DNA staining) prior to surface staining of the cells. Additional details may also be found in the cell enumeration section herein below. It is sometimes desirable to enumerate the WBCs in a blood sample so that a specific number of WBCs can be stained with optimal concentrations of antibodies. In one embodiment, the method comprises counting WBCs using a DNA dye and a spectrophotometer, e.g., as discussed above.

Alternatively, if the number of cells per microliter was determined prior to staining, then a known number of cells could be aliquotted and stained for each sample, regardless of (i) variation within a healthy population and (ii) disease state. To determine the number of cells per microliter of blood, it may be possible to use DNA dyes such as DAPI, DRAQ5®, or propidium iodide. Optionally, unbound dye may be washed away. A spectrophotometer can be used to determine the number of nucleated (e.g., DRAQ5® positive) cells per microliter of blood.

The number and concentration of white blood cells (WBCs) in equal-sized aliquots of blood may vary from subject to subject. However, for adequate analysis of WBCs in a blood sample, sufficient amounts of reagents (such as antibodies targeting particular WBC-specific antigens) may be added, and the amount that is sufficient depends upon the number and concentration of WBCs in a blood sample. A procedure termed "dynamic dilution" may be used to ensure that the sufficient antibody reagent is added to a sample. In one non-limiting example, the procedure treats blood cells in order to obtain a provisional cell count used to gauge the proper amount of reagent (e.g., an antibody cocktail for staining white blood cells (WBCs)) to be used with the sample in order to provide complete staining of the cells. In the procedure, the cells are stained with a DNA dye (e.g., DAPI, DRAQ5®, or propidium iodide) that is spectrally distinct/distant from the emission of the fluorophore-conjugated antibodies that will be used in subsequent steps or assays. Optionally, the sample may be washed to remove excess (unbound) DNA dye after an incubation period. After an incubation period, the sample may be prepared in the appropriate volume, and imaged or measured using a spectrophotometer. The resulting data allows the number of WBCs in the known volume of sample to be enumerated/determined, so that a specific volume of blood can be aliquotted (yielding a particular/desired number of WBCs) and stained with the proper amount of antibodies (i.e., based on the estimated number of WBCs determined using the DNA dye, the amount of antibodies may be determined that are required in order to provide the desired saturation of antibody staining). Thus, the estimate provided by the DNA staining allows calculation and addition of the proper amount of antibody dye required for the number of WBCs in the sample aliquot.

Dynamic Dilution Protocol:

In one embodiment, a dynamic dilution protocol involves taking an aliquot of a blood sample containing white blood cells in order to estimate the amount of reagent containing antibodies targeting the WBCs that is needed for analysis of the sample.

In this non-limiting example, a known volume of a blood sample is taken. A known amount of nuclear dye (e.g., a DNA-staining dye such as propidium iodide, DAPI, or Draq5®) is added to this known volume sample. The mixture is then incubated for a period of 2 to 10 minutes at a temperature between 25° C. to 40° C.

Next a red blood cell (RBC) lysis buffer is added. In this non-limiting example, the mixture is then incubated for a period of 2 to 10 minutes at a temperature between 25° C. to 40° C. (lower temperatures may also be used). A suitable lysis buffer may be, for example, a hypotonic saline solution; a hypotonic sucrose solution; an isotonic ammonium chloride solution; an isotonic solution including a gentle surfactant such as saponin; or other buffer in which RBCs will lyse. In embodiments, such lysis buffers will include a fixative such as paraformaldehyde to aid in stabilizing WBCs. A surfactant such as saponin causes a large number of holes to be formed in the membranes of cells. Red blood cells, due to their unique membrane properties, are particularly susceptible to this hole formation and lyse completely, their contents leaking out into the liquid around. Presence of the fixative prevents unintentional lysis of the white blood cells. Platelets also remain unlysed. The purpose of this step is to remove red blood cells from the mixture as they outnumber white blood cells by about 1000:1. Platelets do not interfere with imaging and hence are not a consideration in this process. In embodiments, a lysis buffer may also contain non-fluorescent beads at a known concentration; these beads may serve as size and/or concentration markers. The lysis of the RBCs, along with the subsequent steps of this protocol, substantially removes any RBC interference to imaging or to optical measurements of the WBCs.

Next the treated sample is separated, where the separation may be performed by any suitable method, such as but not limited to spinning the treated sample in a centrifuge at 1200×g for 3 minutes.

Following separation (e.g., centrifugation), the supernatant is removed; the remaining pellet is then resuspended. In embodiments, the pellet is resuspended in some or all of the supernatant. A known volume of solution containing the resuspended pellet results from this step.

If desired, a further separation step, and a further resuspension step, may be performed. These steps provide a concentrated sample with cells that are approximately 10-fold concentrated (ignoring any possible cell losses at each step).

The amount of DNA-staining dye in the resuspended, concentrated sample is then measured. For example, the fluorescence from a fluorescent DNA-staining dye such as DRAQ5® may be measured in a spectrophotometer. In embodiments, the sample may be illuminated by light at a wavelength of 632 nm (the excitation wavelength of DRAQ5®), the light emitted by the cell suspension may be filtered by a 650 nm long pass filter, and then the emitted light may be measured in a spectrophotometer. This emission measurement is then correlated with a previously generated calibration curve to estimate a rough concentration of white blood cells in the cell suspension. Typically, cell concentrations have ranged from about 1000 cells per microliter to about 100,000 cells per microliter. The estimate of WBC number obtained in this way may be used to calculate an appropriate dilution factor to ensure that the concentration of cells in the sample, when used in subsequent quantitative measurements, is constrained to within a range (e.g., a two-fold or other range) around a pre-defined target concentration. The sample is then diluted per the calculated dilution factor to provide a sample with a WBC concentration within the desired concentration range.

The purpose of this "dynamic dilution" step is to ensure that WBCs are not present at too high or too low a concentration in the sample. If the cell concentration is too high, the accuracy of image processing algorithms is compromised, and if the cell concentration is too low, an insufficient number of cells are sampled. Dilution of a concentrated sample as disclosed herein provides WBC concentrations within a desired range and ensures that signals from the sample during analysis will fall within an optimum range for detection and analysis.

In addition, estimation of the number of WBCs in this way allows the calculation (within a small range) of the amounts of reagents required for further assays and method steps applied to the sample, since the numbers of WBCs in a sample may vary, yet the amount of reagent required for the various assays may depend upon the number of WBCs in the sample to be assayed. For example, the reagents to be added after estimation of WBC number by the dynamic dilution protocol include antibodies that target specific antigens found on different types of WBCs, or, if these antigens are found on multiple types of WBCS, which are present in differing amounts on different types of WBCs. In the absence of such an estimate of the number of WBCs in a sample, predetermined amounts of dyes and other reagents must be used in subsequent assays of the sample, leading to incorrect amounts of reagents and inaccurate or incomplete assay results. Thus, this Dynamic Dilution Protocol serves as an important and useful initial step in the full assessment of a blood sample from a patient, and allows for more precise and accurate measurements to be made than would be possible otherwise.

Dynamic Staining

In some embodiments, methods, systems, and devices are provided herein for dynamic staining of cell-containing samples.

Measurement of a Component of Interest in Cells of a Cellular Population

In one embodiment, a method for dynamically staining a cell sample relates to a method for the measurement of a component of interest in cells of a cellular population in a sample.

As used herein, a "component of interest" refers to any type of molecule that may be present in a cell. "Components of interest" include proteins, carbohydrates, and nucleic acids. Typically, a "component of interest" is a specific species of molecule, such as a particular antigen. Non-limiting examples of "components of interest" of a cell include: CD5 protein, CD3 protein, etc.

As used herein, a "cellular population" refers to any grouping of cells, based on one or more common characteristics. A "cellular population" may have any degree of breadth, and may include a large number of cells or only a small number of cells. Non-limiting examples of "cellular populations" include: red blood cells (RBCs), white blood cells, B-cells, CD34+ B-cells, etc.

In some circumstances, it may be desirable to quantitatively measure a component of interest in cells of a certain cellular population in a sample from a subject. For example, it may be desirable to measure the extent of CD5 (the "component of interest") expression in B-cells (the "cellular population") in a sample of cells from a subject having chronic lymphocytic leukemia. Detection and/or measurement of the level of a component of interest may involve use of a binder molecule that has affinity for the specific component of interest, such an antibody or single chain variable fragment ("scFv"). In order to accurately measure the level of a specific component of interest in cells in a method involving the use of a binder molecule, it may be advantageous to expose the cells to the binder molecule at a specific ratio or range of ratios of binder molecule to target component of interest. For example, it may be desirable to provide an amount of binder to a collection of cells such that there is a linear relationship between the amount of component of interest in the cells and the amount of binder which binds to the component of interest in the cells. For example, it may be undesirable to have too little binder (such that there is not enough binder to bind to all of the components of interest in the cells) or to have too much binder (such that the binder binds non-specifically to the cells).

Using traditional methods, it may be difficult to provide an appropriate level of binder to a sample in order to accurately measure the amount of component of interest in a cellular population in the sample, due to the fact that the size of the cellular population and/or component of interest in the sample may vary significantly between different samples. In contrast, provided herein are methods, devices, and systems for dynamically staining cell samples to accommodate samples containing a wide range of cellular populations and components of interest.

In one embodiment, a method for the measurement of a component of interest in cells of a cellular population in a sample is provided. The method is not limited to but may include one or more of the following steps.

First, a quantitative or semi-quantitative measurement of a marker present in cells of the cellular population may be obtained. The marker may be any marker which is present in the cellular population of interest, and it may be a marker exclusively present in the cellular population of interest (i.e. not present in any other cell types in the sample). Measurement of the marker may be by any method, provided the method does not destroy the sample, and may use any system or device. A binder which recognizes the marker may be mixed with the sample. The binder may have a molecule attached to facilitate detection of the binder (e.g. a fluorescent marker). In an example, the marker may be detected and/or measured by fluorescence spectrophotometry. In embodiments in which the binder has a fluorescent label and the marker is measured by fluorescence spectrophotometry, fluorescence spectrophotometry may be used to measure a bulk fluorescence from the sample or a portion thereof, rather than to measure fluorescence from individual cells.

Second, based on the quantitative or semi-quantitative measurement of the marker present in cells of the cellular population, an approximate amount or concentration of cells of the cellular population present in the sample may be determined. The approximate number or concentration of cells in the cellular population present in the sample may be determined, for example, through the use of a calibration curve. Calibration curves may be prepared and/or may be available for different markers/binder combinations. Calibration curves may be developed, for example, by measuring the signal from known numbers of cells having a certain marker and bound with a certain binder. In some embodiments, the approximate amount or concentration of cells of the cellular population present in the sample may be determined with the aid of a computer. In some aspects, the approximate number or concentration of cells in the cellular population present in the sample may be determined, with such a determination being no more than about 10, 20, 30, 40, 50, 60, 70, 80, 90, 100, 150, 200, 250, 300, 400, or 500% off the true concentration.

Third, based on the determined amount or concentration of cells in the cellular population present in the sample, an amount of a reagent to add to the sample may be selected, wherein the reagent binds specifically to the component of interest in cells of the cellular population. The reagent may be or include any molecule that binds specifically to the component of interest. For example, the reagent may be a binder, such as an antibody. The reagent may be configured such that it may be readily detected (e.g. by fluorescence or luminescence) and/or such that under at least some circumstances, it produces a detectable signal. In some embodiments, the reagent may be attached to a molecule to facilitate detection of the reagent. The amount of reagent added to the sample may be any amount. In some embodiments, an amount of reagent may be added to the sample such that there is an approximately linear relationship between the level of the component of interest in individual cells of the cellular population and the signal produced by the reagents bound to the components of interest in individual cells of the cellular population.

Fourth, after the amount of a reagent to add to the sample is selected, the selected amount of reagent may be added to the sample.

Fifth, cells in the sample may be assayed for reagent bound to the component of interest.

Sixth, based on the amount of reagent bound to the component of interest, the amount of the component of interest in cells of the cellular population of the sample may be determined.

In some embodiments, the fifth and sixth steps may be performed together such that the measurement of the amount of reagent bound to the component of interest is sufficient to identify the amount of the component of interest in cells of the cellular population of the sample.

In other embodiments, provided herein are systems and devices for the dynamic staining of samples. The systems and devices may contain, without limitation, a spectrophotometer and a fluorescence microscope. In an embodiment, a system or method for dynamic staining of samples may be configured as described in U.S. patent application Ser. No. 13/244,947 or 13/355,458, which are hereby incorporated by reference in their entirety. In an embodiment, the systems and devices may be automated to determine an amount of a reagent to add to a sample to determine the amount of a component of interest in cells of a cellular population in a sample, based on a measurement of an amount of a marker present in cells of the cellular population. In another embodiment, the systems and devices may be automated to determine an amount of a reagent to add to a sample to determine the amount of a first component in cells of a cellular population in a sample, based on a measurement of an amount of a second component in the cells of the cellular population in a sample.

Context-Based Autofocus

In some embodiments, methods, systems, and devices are provided herein for context-based microscopy autofocus.

The size (e.g., length, height, or other measure) of many clinically relevant objects in biological samples spans a wide range. For example, bacteria are commonly about 1 μm in length, erythrocytes are commonly about 6-8 μm in length, leukocytes are commonly about μm 10-12 in length, epithelial cells may be about 100 μm in length, and cast and crystals may be about 200-300 μm in length. In addition, there are many amorphous elements such as urinary mucus which exist as strands or filaments which may range from about 10-400 μm in length.

A challenge in microscopy is to acquire precise images of fields of view that contain an unknown and arbitrary composition of objects of various sizes, such as those described above. Since the depth of focus of many microscopy objectives is limited (typically about 1-10 μm), for a given field of view containing elements of various sizes, multiple focal planes for the given field of view may need to be acquired in order to obtain accurate sharp images of the various elements within the field of view. A problem with many traditional autofocus methods is that they are designed to focus on the dominant feature in a field of view, so that the sharpness of that feature can be maximized. Such methods may be ineffective for capturing elements of various sizes in a sample.

In one embodiment, a method is provided for context-based microscopy autofocus, which includes mixing a reference particle of a known size with a sample for microscopy. In embodiments, more than one reference particle is added to the sample; preferably all, or substantially all, of such reference particles are of the same known size. In embodiments, the number of reference particles added to a particular volume of sample is known. The reference particles may be detected during microscopy, and used to achieve focusing. By use of the reference particles to achieve focusing, focal planes may be selected independent from the overall image composition. In one aspect, the method may be useful to achieve focusing on a sample having an unknown composition of elements. In another aspect, the method may support the generation of precise planes of focus, independent of the precision of the microscope or microscopy-related hardware. For example, when a plane of focus is selected based on feedback from the sharpness of the reference particles within a field of view, precise focusing on various elements within a sample may be achieved, regardless of the level of accuracy or precision of the focusing hardware [e.g. the microscope objective actuation, the shape of a sample holder (e.g. a cuvette or slide), or the non-uniformity of a sample holder].

In an embodiment, a reference particle may contain or be labeled with a molecule to facilitate detection of the particle during microscopy. In one example, a reference particle may be labeled with or contain a fluorescent molecule. The fluorescent molecule may absorb light at a first wavelength of light, and, in response to the absorbance of the first wavelength of light, it may emit light at a second wavelength. In an embodiment, a sample mixed with a reference particle may be exposed to a wavelength of light capable of exciting a fluorescent molecule in a reference particle of interest and emitted light from the fluorescent molecule may be measured. Specific fluorescence from a reference particle may be used to detect reference particles, and information from detected reference particles in a sample may be used for autofocusing.

Reference particles may be of any shape, such as spherical or cuboid. Reference particles include, without limitation, beads and microspheres. Reference particles may be of any size, such as with a diameter or length of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 20, 30, 40, 50, 60, 70, 80, 90, 100, 125, 150, 175, 200, 250, 300, 350, 400, 450, or 500 µm. Reference particles may be made of, or may contain, any suitable material, such as polystyrene, polyethylene, latex, acrylic, or glass. For example, a reference particle may be a polystyrene bead, e.g., a polystyrene bead having a diameter of between about 0.1 µm and about 50 µm; or between about 1 µm and about 20 µm; or between about 5 µm and about 15 µm; or having a diameter of about 10 µm.

In one embodiment, a method for focusing a microscope is provided, which may include one or more of the following steps. First, a sample containing an object for microscopic analysis (e.g. bacteria, erythrocytes, etc.) may be mixed with a reference particle. The reference particle may contain or be labeled with a molecule to facilitate the detection of the particle, such as a fluorophore. Second, the mixture containing the reference particle and the sample may be positioned into a light path of a microscope, for example in cuvette or slide. Optionally, the reference particle may sink to the bottom of the sample in the cuvette or slide, such that the reference particle rests on the lowest surface of the cuvette or slide which is in contact with the sample. The microscope may be of any type, including a fluorescent microscope. Third, the mixture may be exposed to a light beam configured to visualize the reference particle. The light beam may be of any type, and may be of any orientation relative to the reference particle. For example, the light beam may be at a wavelength capable of exciting a fluorophore within or attached to the reference particle. Exposure of the reference particle to the light beam may result in, for example, the generation and emission of light at a particular wavelength from the reference particle and/or scattering of light from the reference particle. Fourth, light emitted or scattered from the reference particle may be detected by the microscope, and this information may be used in order to determine the position of the reference particle within the mixture and/or to focus the microscope. Optionally, the microscope may be focused into a plane of focus suited for objects of similar size to the reference particle. An image from the microscope may be obtained by an image sensor. The image may be saved and/or or used for image analysis.

In some embodiments, a plurality of reference particles may be added to a sample. The reference particles may be all of the same size, or they may be of different sizes. In some embodiments, reference particles of different sizes contain different fluorophores. Different fluorophores may have different absorption wavelengths, different emission wavelengths, or both.

In an embodiment, a method for focusing a microscope is provided, including mixing more than one reference particle of known size with a sample for microscopy, wherein at least two of the reference particles are of different sizes and contain different fluorophores. The method may include one or more of the following steps. First, a sample containing an object for microscopic analysis may be mixed with two or more reference particles, wherein at least two of the reference particles are of different sizes and contain different fluorophores (i.e. the "first reference particle" and the "second reference particle"). Second, the mixture containing the reference particles and the sample may be positioned into the light path of a microscope. The microscope may be of any type, including a fluorescent microscope. Third, the mixture may be exposed to a light beam configured to visualize the first reference particle. The light beam may be of any type, and may be of any orientation relative to the first reference particle. For example, the light beam may be at a wavelength capable of exciting a fluorophore within or attached to the first reference particle. Exposure of the first reference particle to the light beam may result in the generation and emission or scattering of light at a particular wavelength from the first reference particle. Fourth, light emitted or scattered from the first reference particle may be detected, and this information may be used in order to determine the position of the first reference particle within the mixture and/or to focus the microscope into a first plane of focus suited for objects of similar size to the first reference particle. Optionally, an image of the first focal plane may be obtained by an image sensor. The image may be saved and/or or used for image analysis. Fifth, the mixture may be exposed to a light beam configured to visualize the second reference particle. The light beam may be of any type, and may be of any orientation relative to the second reference particle. Exposure of the second reference particle to the light beam may result in the generation and emission or scattering of light at a particular wavelength from the second reference particle. Sixth, light emitted or scattered from the second reference particle may be detected, and this information may be used in order to determine the position of the second reference particle within the mixture and/or to focus the microscope into a second plane of focus suited for objects of similar size to the second reference particle. Optionally, an image of the second focal plane may be obtained by an image sensor. The image may be saved and/or or used for image analysis.

In other embodiments, provided herein are systems and devices for context-based microscopy autofocus. The systems and devices may contain, without limitation, a fluorescence microscope. In an embodiment, the systems and devices may be automated to add a reference particle having a known size to a sample for microscopic analysis to form a mixture, to position the mixture into the light path of a microscope, to expose the mixture to a light beam configured to visualize the reference particle, to determine the position of the reference particle within the mixture and/or to focus the microscope based on the position of the reference particle within the mixture. In an embodiment, a system or method for context-based microscopy autofocus may be configured as described in U.S. patent application Ser. No. 13/244,947 or 13/355,458, which are hereby incorporated by reference in their entireties.

Locating a Sample Holder

In some embodiments, methods, systems, and devices are provided herein for determining the location of a sample holder, or of a portion of, or indicial mark on, a sample holder. Such a determination is preferably a precise determination, and is useful for identifying cells, particles, or other objects in a field of view within a sample holder even after a sample holder has been moved, or a field of view has been altered (e.g., by changing focus, or by inspection of different areas in a sample holder).

In embodiments, an image based feedback mechanism may be used to accurately and precisely determine a certain location in a cuvette, e.g., in a channel or other region containing a sample (see, e.g., an analysis area 608 shown in FIGS. 7 and 8). Such determination, particularly when the sample holder is moved, and then returned to a previous position, is important for comparison of images and optical measurements taken before such movement, and after such movement. Variability from multiple sources may affect the position of the sample relative to the axis of the imaging system; for example, variability in cuvette parts, variability in cuvette assembly, variability in cuvette positioning on the imaging system, and other possible sources of variability may affect the position of a sample with respect to the imaging system even if the sample remains in the same position within the sample holder. Methods for identifying and characterizing the position of a sample holder with respect to an imaging system are disclosed herein. For example, in order to accurately and reproducibly image an area of interest in a cuvette, a cuvette registration program may be run. In embodiments, such a program begins by analyzing images taken at a predefined location in a sample holder, the predefined location being close to a registration feature or fiducial marker within the field of view, or otherwise detectable by the program. A cuvette registration program comprises an image processing program, which image processing program searches for the existence of the fiducial marker in the image and returns either a yes/no answer (regarding whether or not the fiducial marker is found within the inspected region) or a probability of the marker being in the image. In instances where the fiducial marker is not found in the area that has been inspected, a search algorithm is then used, which moves the area of inspection to a different location on or in the sample holder, and repeats the imaging. This process is repeated until the program finds the fiducial marker (i.e. gets a "yes" to the question of whether or not the fiducial marker is found within the inspected region, or maximizes the probability of the marker being within that region). Once the position of the fiducial marker is identified, all other positions in or on the sample holder may be determined, since the dimensions and layout of the sample holder are known. Thus, following identification of the location of the fiducial marker, any point of interest for imaging can be found and imaged, as the location of the point of interest is thus known also (i.e., its distance and orientation from the fiducial marker is known, and, since the position of the fiducial marker is known, the point of interest is also known). In embodiments, a fiducial marker can be or include a specially engineered feature on the cuvette itself (e.g., may be a hole, a protrusion, a printed or molded pattern, or other feature) which can be manufactured to be in the same location for every part to any desired tolerance. In embodiments, a fiducial marker may be or include a feature of the cuvette (e.g., the edge of a channel) that is always at a fixed distance from the point of interest (e.g., where the fiducial marker is the edge of channel, the fiducial marker is always a fixed distance from the central axis of the channel).

Cell Counting/Enumerating Cells

In some embodiments, methods, systems, and devices are provided herein for enumerating cells in a sample.

Certain traditional methods for staining cell-containing samples involve staining a specific volume of a sample (e.g. blood) with a particular concentration or amount of stain. This may be referred to as "volumetric staining." Volumetric staining has a number of shortcomings, including: (i) it fails to address normal variations in cell subpopulations between different subjects (e.g. different healthy subjects may have widely different numbers of subpopulations of cells, such as CD3+ T cells (where "CD3+" indicates that the T cells express the CD3 marker)) and (ii) it fails to address that pathological samples may have dramatically different cellular composition when compared to healthy samples (e.g. the percent and number of CD3+ T cells in blood are greatly elevated in patients with T cell leukemia over the percent and number in healthy subjects).

For accurate and reproducible staining of cell-containing samples, it may be desirable to add a specific amount of a cellular stain (e.g. DNA dyes, antibodies, binders, etc.) to a specific number or concentration of cells. For example, it may be desirable to add 0.2 micrograms of a particular stain for white blood cells per 1000 white blood cells in a sample. After an incubation period of the dye with the cells, a sample may be washed to remove excess (unbound) dye, prepared to an appropriate cell density for microscopy, and imaged. In this manner, a stain and staining procedure can be optimized or normalized for a particular cell number.

In one embodiment, a method is provided for enumerating the number of cells of interest in a sample. The method may include one or more of the following steps or elements. A first stain that will bind to the cells of interest in a sample may be added to the sample. The mixture of first stain and sample may be incubated. The cells in the mixture of first stain and sample may be washed to remove excess (unbound) stain. The washed cells stained with a first stain may be prepared in a desired volume for further analysis. The washed cells stained with a first stain may be analyzed by a spectrophotometer. Data from the spectrophotometer may be used to enumerate the approximate number of cells in the sample. For example, the first stain may be a fluorescent dye which binds to nucleic acids, and the spectrophotometer may include a light source which emits light at an excitation wavelength of the fluorescent dye, and a light sensor which can detect light in the emission wavelength of the fluorescent dye. In this example, based on the fluorescent signal from the dye, the approximate amount of nucleic acid in the sample may be calculated, and from this approximate amount of nucleic acid in the sample, the approximate number of cells in the sample may be determined Based on the number of cells in the sample, a second stain that will bind to cells of interest in a sample may be added to the sample. In embodiments, the amount of second stain added to the sample may be determined in view of the approximate number of cells determined using the first stain. In embodiments, the amount of second stain added to the sample may be calculated using the number of cells determined by use of the first stain, in order that a desired ratio of second stain per cell be obtained. The mixture of second stain and sample may be incubated. The cells in the mixture of second stain and sample may be washed to remove excess stain. The washed cells stained with a second stain may be prepared in a desired volume for further analysis. The washed cells stained with a second stain may be analyzed by microscopy.

Enumerating Cells in a Sample Prior to Determining the Ploidy of Cells

In one embodiment, a method for enumerating cells in a sample prior to determining the ploidy of the cells is provided, wherein the method includes one or more of the following steps or elements. A first stain which binds to the cells of interest in the sample and that is spectrally distinct from the emission of a DNA dye may be added to the sample. The cells of interest may be, for example, white blood cells. The first stain may be, for example, a fluorphore-conjugated antibody. A fluorphore-conjugated antibody may bind to, for example, a widely expressed antigen (e.g. CD45), or it may bind to an antigen expressed by a specific sub-population of cells (e.g. CD3 for T cells). The mixture of first stain and sample may be incubated. The cells in the mixture of first stain and sample may be washed to remove excess (unbound) stain. The washed cells stained with a first stain may be prepared in a desired volume for further analysis. The washed cells stained with a first stain may be analyzed by a spectrophotometer. Data from the spectrophotometer may be used to enumerate the approximate number of cells in the sample. Based on the number of cells in the sample, a second stain that will bind to cells of interest in a sample may be added to the sample. The second stain may be a DNA dye, such as propidium iodide or 4',6-diamidino-2-phenylindole ("DAPI"). In embodiments, the amount of second stain added to the sample may be determined in view of the approximate number of cells determined using the first stain. In embodiments, the amount of second stain added to the sample may be calculated using the number of cells determined by use of the first stain, in order that a desired ratio of second stain per cell be obtained. The mixture of second stain and sample may be incubated. The cells in the mixture of second stain and sample may be washed to remove excess stain. The washed cells stained with a second stain may be prepared in a desired volume for further analysis. The washed cells stained with a second stain may be analyzed for ploidy by microscopy.

In methods for determining the ploidy of cells, it may be important to combine a given number of cells for ploidy analysis with a certain amount or concentration of DNA stain, in order to generate accurate and consistent data regarding the ploidy of the cells. In one example, the number of white blood cells per volume of blood may vary within a healthy population, and thus, it may be desirable to determine the number of white blood cells in a volume of blood before attempting to stain the white blood cells for ploidy analysis.

The methods provided above for determining the ploidy of cells may also be performed for any method in which enumerating cells in a sample prior to determining an attribute related to the nucleic acid content of a cell is desired. For example, the above method may be used with methods involving enumerating cells in a sample prior to determining the morphology of nuclei of cells, the size of the nuclei of cells, the ratio of nuclei area to total cell area, etc.

Enumerating Cells in a Sample Prior to Cell Surface Staining

In one embodiment, a method for enumerating cells in a sample prior to cell surface staining is provided, wherein the method includes one or more of the following steps or elements. A first stain which binds to the cells of interest in the sample and that is spectrally distinct from the emission of a dye to be used to stain the surface of the cells of interest may be added to the sample. The cells of interest may be, for example, white blood cells. The first stain may be, for example, a DNA dye (e.g. propidium iodide, DRAQ5® or DAPI). The mixture of first stain and sample may be incubated. The cells in the mixture of first stain and sample may be washed to remove excess (unbound) stain. The washed cells stained with a first stain may be prepared in a desired volume for further analysis. The washed cells stained with a first stain may be analyzed by a spectrophotometer. Data from the spectrophotometer may be used to enumerate the approximate number of cells in the sample. Based on the number of cells in the sample, a second stain that will bind to cells of interest in a sample may be added to the sample. In embodiments, the amount of second stain added to the sample may be determined in view of the approximate number of cells determined using the first stain. In embodiments, the amount of second stain added to the sample may be calculated using the number of cells determined by use of the first stain, in order that a desired ratio of second stain per cell be obtained. The second stain may be, for example, a fluorphore-conjugated antibody. A fluorphore-conjugated antibody may bind to, for example, a widely expressed antigen (e.g. CD45), or it may bind to an antigen expressed by a specific sub-population of cells (e.g. CD3 for T cells). The mixture of second stain and sample may be incubated. The cells in the mixture of second stain and sample may be washed to remove excess stain. The washed cells stained with a second stain may be prepared in a desired volume for further analysis. The washed cells stained with a second stain may be analyzed for a cell surface antigen by microscopy.

In methods for cell surface antigen staining of cells, it may be important to combine a given number of cells for analysis with a certain amount or concentration of cell surface antigen stain, in order to generate accurate and consistent data regarding the content of the cell surfaces. In one example, the number of white blood cells per volume of blood may vary within a healthy population (blood from healthy subjects typically has between about 3000 and 10,000 WBCs per μL), and thus, it may be desirable to determine the number of white blood cells in a volume of blood before attempting to stain the white blood cells for cell surface antigens. In another example, the number of white blood cells per volume of blood may vary between healthy and sick subjects (e.g., lymphoma patients may have up to 100,000 WBCs per μL of blood), and thus, it may be desirable to determine the number of white blood cells in a volume of blood before attempting to stain the white blood cells for cell surface antigens.

Thus, as a theoretical example, a healthy patient may have 5000 cells per microliter of blood, and 500 of these are CD3+ T cells, while a lymphoma patient may have 50,000 cells per microliter of blood and 45,000 of these are CD3+ T cells. If 100 microliters of blood is traditionally stained, then a sample from a healthy subject would contain about 500,000 total cells, of which about 50,000 cells would be CD3+ T cells. A 100 microliter sample from a lymphoma subject would contain about 5,000,000 total cells, of which about 4,500,000 cells would be CD3+ T cells. In this theoretical example, the pathological sample contains ten times the number of total cells and ninety times the number of CD3+ T cells, when compared to a sample from a healthy subject. If the pathological sample would be stained with a traditional "volumetric staining" approach that is optimized for samples from healthy subjects, the sample from the lymphoma subject may be insufficiently stained. For this reason, for example, the present methods in which a prior estimate of the number of cells in a sample is used to adjust the amount of dye applied to a sample provide advantages over traditional volumetric staining methods.

Accordingly, methods provided herein may be used to enumerate cells in a sample before cell staining, in order to generate accurate and/or consistent data regarding samples.

Method Speeds

Methods, systems, and devices provided herein may support the rapid acquisition of sample analysis results. Methods provided herein may provide analysis results in less than, for example, about 6 hours, 4 hours, 3 hours, 2 hours, 1 hour, 45 minutes, 30 minutes, 15 minutes, 10 minutes, or 5 minutes from the initiation of the method.

Rapid analysis results may be used to provide real-time information relevant to the treatment, diagnosis, or monitoring of a patient. For example, rapid analysis results may be used to guide a treatment decision of a surgeon operating on a patient. During surgery, a surgeon may obtain a biological sample from a patient for analysis. By receiving rapid analysis of a sample by a method provided herein, a surgeon may be able to make a treatment decision during the course of surgery.

In another example, rapid analysis results provided by the methods, systems, and devices provided herein may support a patient receiving information regarding a biological sample provided by the patient at a point of service during the same visit to the point of service location in which the patient provided the biological sample.

For example, Applicants describe herein a rapid assay which may be used to prepare a sample of whole blood for analysis of white blood cells for the presence of multiple markers and cell types. Such an assay is useful for preparing samples of whole blood for imaging analysis; the samples are ready for imaging in less than about 20 minutes, or in less than about 15 minutes.

Rapid White Blood Cell Assay from Whole Blood

This assay prepares samples of whole blood for cytometric analysis of white blood cells in less than about 15 minutes or less than about 20 minutes. Automated cytometric analysis of such prepared cells may also be done rapidly, so that cytometric WBC analysis can be performed from whole blood in about half an hour or less. In addition, this assay uses only a small volume of the blood sample, so is sparing of resources, and less inconvenient or uncomfortable to a subject than assays which require larger volumes of blood.

Reagents used in this assay include: phosphate buffered saline, Lyse Fix buffer, beads, resuspension buffer, and reagent cocktails which contain dyes and dye-conjugated antibodies. The antibodies are directed to specific WBC markers.

Phosphate buffered saline (PBS): 137 mM NaCl, 3 mM KCl, 8 mM, Na2HPO4, 1.5 mM KH2PO4, pH adjusted to pH to 7.2 to pH 7.4 (with HCl).

Resuspension buffer (RSB): 5% bovine serum albumin in PBS.

Lyse Fix buffer: 0.0266% saponin in PBS with 10% paraformaldehyde (PFA), where "%" indicates grams/100 mL (final ratio is approximately 13:1 saponin PBS:PFA).

Reagent Cocktail 1: DRAQ5®, anti-CD14 antibody conjugated to Pacific Blue™ dye, Fc block (e.g., immunoglobulin such as mouse IgG), in 0.2% BSA in PBS.

Reagent Cocktail 2: anti-CD16 antibody conjugated to phycoerythrin (PE) dye, anti-CD45 antibody conjugated to Alexa Fluor® 647 dye, anti-CD123 antibody conjugated to PECy5 dye, Fc block (e.g., immunoglobulin), in 15% BSA in PBS.

Assay steps include:

Obtain whole blood from a subject.

Place 50 µL of whole blood in a tube. If desired, the blood sample may be acquired directly to a tube. Where 50 µL is the total amount of blood taken from the subject, then the entire sample is added or acquired to a tube; where more than 50 µL is acquired from a subject, then the 50 µL is an aliquot of the sample.

Centrifuge the sample at 1200×g for 3 minutes.

Remove 20 µL of plasma from the tube.

Place the tube on heat block (to raise the temperature to 37° C.), add 20 µL of RSB, and mix thoroughly.

Add Cocktail 1 (approximately 5 µL. (In embodiments, Cocktail 1 may be added directly to whole blood, and the previous steps of centrifugation, removal of an aliquot of plasma and replacement with RSB may be omitted.)

Incubate the sample at 37° C. for 2 minutes.

Add Lyse Fix buffer (at a 6:1 ratio of (Lyse Fix buffer) to (stained blood); approximately 300-350 µL). A known concentration of beads may be included in the Lyse Fix buffer to provide targets (reference particles) for focusing and to provide a calibration for the concentration of the sample (e.g., as described above under the heading "Context-based Autofocus"). Polystyrene or other beads, having diameters of about 1 micron to about 30 microns, may be used. For example, 10 micron polystyrene beads at a concentration of about 100 beads to about 2000 beads per microliter may be used.

Incubate in the Lyse Fix buffer at 37° C. for a total of 3 minutes; at about 1.5 minutes after addition of the buffer, mix by pipetting the solution up and down five times.

Centrifuge the sample mixture at 1200×g for 3 minutes.

Remove the supernatant (approximately 350 µL). Save the supernatant to adjust the volume, if needed, in later steps.

Add Cocktail 2 (approximately 15 µL) to provide the final mixture.

Load the final mixture on a pre-warmed imaging cuvette (37° C.).

Incubate the cuvette at 37° C. for 5 minutes before imaging.

Image the sample.

Thus, the sample is ready for imaging in less than about 15 minutes. In embodiments, some of the steps may be shortened (e.g., in alternative embodiments, a centrifugation step or an incubation step may be shortened). Since the methods disclosed above prepare the sample using cocktails which include multiple dyes, analysis of these samples for the presence of several cell-type markers may be performed within a single field of view, providing efficient imaging of the samples with minimal duplication of effort. Light scatter images of these same fields of view provides yet another aspect of analysis which may be applied efficiently without requiring separate samples or separate fields of view for the several modes of image analysis of the samples. Inclusion of reference particles of a known size further aids imaging by allowing use of automatic focusing and, since the concentration of the reference particles is known, provides an independent measure of sample dilution and cell concentration in each image.

The imaging of the prepared sample may also be done rapidly; for example, such imaging may be performed in about 10 minutes (typically between about 2 minutes and about 12 minutes) by automatic devices having features as described herein and, for example, in U.S. patent application Ser. No. 13/244,947, in U.S. patent application Ser. No. 13/769,779, and related applications. Thus, in embodiments, the entire analysis, including preparation of the blood sample and imaging of the prepared sample, may be performed in about 30 minutes or less.

The images and image analysis obtained from samples prepared according to the methods discussed above (and similar methods discussed below) are suitable for identifying different populations of WBCs from whole blood. Such identification and quantification is done rapidly on the same sample by illumination of the sample (e.g., sequentially) with different wavelengths of light and recording and analyzing the resulting images and light intensities. Such methods are suitable for providing the images and plots as shown, for example, in FIGS. 9, 10, and 11, which were prepared using methods as disclosed herein (e.g., methods discussed both supra and infra). The comparisons shown in FIG. 12 demonstrate that these methods are accurate and reliable, and correlate well with other methods (e.g., analysis by an Abbott CELL-DYN Ruby System (Abbott Diagnostics, Lake Forest, Ill., USA)) the reference analyzer used for the comparisons shown in FIG. 12.

Analysis of Pathology Samples

Any of the methods provided herein may be used to analyze cell-containing pathology samples. If a pathology sample is a tissue sample, the sample may be treated to separate the cells of the tissue into individual cells for analysis by methods provided herein.

Analysis of pathology samples by any of the methods provided herein may support rapid pathology analysis, and the rapid integration of pathology analysis results into a treatment decision for a patient.

Additional Procedures in Response to Analysis Results

In some embodiments, the devices and systems provided herein may be configured to trigger an additional procedure in response to a result obtained by an analysis method provided herein.

In one example, a device or system may be programmed to provide an alert to a user if a result is outside of an expected range. The alert may prompt a user or medical personnel to, for example, manually analyze a sample, check the device or system for proper operation, etc.

In another example, a device or system may be programmed to automatically run one or more additional tests on a sample if a result is within or outside of a certain range. In some examples, devices and systems provided herein are capable of performing multiple different assays, and the device or system may run an addition assay to verify or further investigate a result generated by a method provided herein.

Analysis Using Non-Specific Dyes

One non-limiting example to accelerate imaging is to use a "high light" situation, where cells are labeled with very high concentration of dyes. In the present embodiment, non-specific dyes are used that label the DNA, the membranes, or other portion of the cells. This example does not use antibody dyes that target specific and rare proteins or other markers.

With the non-specific dye, it is possible to obtain cell information without requiring a separation step (such as, e.g., separation by centrifugation or by performing physical separation). Without this separation step, one can more rapidly move directly to imaging the sample, such as but not limited imaging a large area of cells that may include both a) non-target cells such as red blood cells (RBCs) and b) target cells or objects of interest such as white blood cells (WBCs). Thus, in one non-limiting example of imaging a blood sample, one can image five million RBCs and five thousand or other number of WBCs therein. The targeted cells can be differentiated based on what is inside the cell such as but not limited to the shape of the nucleus of a cell. In one embodiment, a nuclear stain is used to stain the nuclei of cells in a sample, and based on the kind and amount of staining a particular cell has (e.g., the presence of nuclear staining, or the shape of a stained nucleus, or other characteristic), one can determine its cell type based on this staining, even though the dye is non-specific. In other examples, other internal shapes in the cell (such as, e.g., whether or not the cytoplasm has granules or other objects therein) can be indicative or characteristic and be used to identify and quantify cells in a sample. For a urine sample, any cells present, and crystal shapes in the sample can be used to identify a sample and to determine whether or not abnormalities are found. In this manner, the use of non-specific dyes can be used to rapidly image cells in a manner that can be used to determine cells as desired.

Analysis Using a Plurality of Excitation and/or Detection Channels

In the context of using even smaller sample volumes for cytometry, in embodiments of advanced cytometry assays, an additional excitation and/or detection wavelength may be used. For example, for classification of WBCs in a lymphocyte subset assay, the various cells such as T cells, B cells, K cells, and other cells are to be counted. In this case, one uses two markers merely to identify that the cell is a lymphocyte. To further sub-classify the cells in a blood sample, for example, one may again use two markers. Thus, if one has a system that can only detect two colors at a time, there is an insufficient number of wavelengths for the analysis.

In one embodiment, one can aliquot the sample to make two separate sample portions and then one can image one combination in one part and another combination in another part of the system, using different parts of the sample. Unfortunately, this can cause a doubling of volume and time. The more independent channels that are built into a system, the lesser the number of these sample parts or volume used.

EXAMPLES

Cell Processing

In embodiments, it is often useful to process biological samples for imaging, testing, and analysis. For example, it is often useful to process biological samples containing cells for imaging, testing, and analysis.

Processing of a biological sample may include pre-processing (e.g., preparation of a sample for a subsequent processing or measurement), processing (e.g., alteration of a sample so that it differs from its original, or previous, state), and post-processing (e.g., disposal of all or a portion of a sample following its measurement or use). A biological sample may be divided into portions, such as aliquots of a blood or urine sample, or such as slicing, mincing, or dividing a tissue sample into two or more pieces. Processing of a biological sample, such as blood sample, may include mixing, stirring, sonication, homogenization, or other processing of a sample or of a portion of the sample. Processing of a biological sample, such as blood sample, may include centrifugation of a sample or a portion thereof. Processing of a biological sample, such as blood sample, may include providing time for components of the sample to separate or settle, and may include filtration (e.g., passing the sample or a portion thereof through a filter). Processing of a biological sample, such as blood sample, may include allowing or causing a blood sample to coagulate. Processing of a biological sample, such as blood sample, may include concentration of the sample, or of a portion of the sample (e.g., by sedimentation or centrifugation of a blood sample, or of a solution containing a homogenate of tissue from a tissue sample) to provide a pellet and a supernatant. Processing of a biological sample, such as blood sample, may include dilution of a portion of the sample. Dilution may be of a sample, or of a portion of a sample, including dilution of a pellet or of a supernatant from sample. A biological sample may be diluted with water, or with a saline solution, such as a buffered saline solution. A biological sample may be diluted with a solution which may or may not include a fixative (e.g., formaldehyde, paraformaldehyde, or other agent which cross-links proteins). A biological sample may be diluted with a solution effective that an osmotic gradient is produced between the surrounding solution and the interior, or an interior compartment, of such cells, effective that the cell volume is altered. For example, where the resulting solution concentration following dilution is less than the effective concentration of the interior of a cell, or of an interior cell compartment, the volume of such a cell will increase (i.e., the cell will swell). A biological sample may be diluted with a solution which may or may not include an osmoticant (such as, for example, glucose, sucrose, or other sugar; salts such as sodium, potassium, ammonium, or other salt; or other osmotically active compound or ingredient). In embodiments, an osmoticant may be effective to maintain the integrity of cells in the sample, by, for example, stabilizing or reducing possible osmotic gradients between the surrounding solution and the interior, or an interior compartment, of such cells. In embodiments, an osmoticant may be effective to provide or to increase osmotic gradients between the surrounding solution and the interior, or an interior compartment, of such cells, effective that the cells at least partially collapse (where the cellular interior or an interior compartment is less concentrated than the surrounding solution), or effective that the cells swell (where the cellular interior or an interior compartment is more concentrated than the surrounding solution).

A biological sample may be contacted with a solution containing a surfactant, which may disrupt the membranes of cells in the sample, or have other effects on cell morphology. For example, contacting RBCs with a low concentration of a surfactant causes the RBCs to lose their disc-like shape and to assume a more spherical shape.

A biological sample may be dyed, or markers may be added to the sample, or the sample may be otherwise prepared for detection, visualization, or quantification of the sample, a portion of a sample, a component part of a sample, or a portion of a cell or structure within a sample. For example, a biological sample may be contacted with a solution containing a dye. A dye may stain or otherwise make visible a cell, or a portion of a cell, or a material or molecule associated with a cell in a sample. A dye may bind to or be altered by an element, compound, or other component of a sample; for example a dye may change color, or otherwise alter one of more of its properties, including its optical properties, in response to a change or differential in the pH of a solution in which it is present; a dye may change color, or otherwise alter one of more of its properties, including its optical properties, in response to a change or differential in the concentration of an element or compound (e.g., sodium, calcium, $CO_2$, glucose, or other ion, element, or compound) present in a solution in which the dye is present. For example, a biological sample may be contacted with a solution containing an antibody or an antibody fragment. For example, a biological sample may be contacted with a solution that includes particles. Particles added to a biological sample may serve as standards (e.g., may serve as size standards, where the size or size distribution of the particles is known, or as concentration standards, where the number, amount, or concentration of the particles is known), or may serve as markers (e.g., where the particles bind or adhere to particular cells or types of cells, to particular cell markers or cellular compartments, or where the particles bind to all cells in a sample).

Cytometry includes observations and measurements of cells, such as red blood cells, platelets, white blood cells, including qualitative and quantitative observations and measurements of cell numbers, cell types, cell surface markers, internal cellular markers, and other characteristics of cells of interest. Where a biological sample includes or is a blood sample, the sample may be divided into portions, and may be diluted (e.g., to provide greater volume for ease of handling, to alter the density or concentration of cellular components in the sample to provide a desired diluted density, concentration, or cell number or range of these, etc.). The sample may be treated with agents which affect coagulation, or may be treated or handled so as to concentrate or precipitate sample components (e.g., ethylene diamine tetraacetic acid (EDTA) or heparin may be added to the sample, or the sample may be centrifuged or cells allowed to settle). A sample, or portion of a sample, may be treated by adding dyes or other reagents which may react with and mark particular cells or particular cellular components. For example, dyes which mark cell nuclei (e.g., hematoxylin dyes, cyanine dyes, drag dyes such as Drags®, and others); dyes which mark cell cytoplasm (e.g., eosin dyes, including fluorescein dyes, and others) may be used separately or together to aid in visualization, identification, and quantification of cells. More specific markers, including antibodies and antibody fragments specific for cellular targets, such as cell surface proteins, intracellular proteins and compartments, and other targets, are also useful in cytometry.

Biological samples may be measured and analyzed by cytometry using optical means, including, for example, photodiode detectors, photomultipliers, charge-coupled devices, laser diodes, spectrophotometers, cameras, microscopes, or other devices which measure light intensity (of a single wavelength, of multiple wavelengths, or of a range, or ranges, of wavelengths of light), form an image, or both. A field of view including a sample, or portion of a sample, may be imaged, or may be scanned, or both, using such detectors. A biological sample may be measured and analyzed by cytometry prior to processing, dilution, separation, centrifugation, coagulation, or other alteration. A biological sample may be measured and analyzed by cytometry during or following processing, dilution, separation, centrifugation, coagulation, or other alteration of the sample. For example, a biological sample may be measured and analyzed by cytometry directly following receipt of the sample. In other examples, a biological sample may be measured and analyzed by cytometry during or after processing, dilution, separation, centrifugation, coagulation, or other alteration of the sample.

For example, a blood sample or portion thereof may be prepared for cytometry by sedimentation or centrifugation. A sedimented or pellet portion of such a sample may be resuspended in a buffer of choice prior to cytometric analysis (e.g., by aspiration, stirring, sonication, or other processing). A biological sample may be diluted or resuspended with water, or with a saline solution, such as a buffered saline solution prior to cytometric analysis. A solution used for such dilution or resuspension may or may not include a fixative (e.g., formaldehyde, paraformaldehyde, or other agent which cross-links proteins). A solution used for such dilution or resuspension may provide an osmotic gradient between the surrounding solution and the interior, or an interior compartment, of cells in the sample, effective that the cell volume of some or all cells in the sample is altered. For example, where the resulting solution concentration following dilution is less than the effective concentration of the interior of a cell, or of an interior cell compartment, the volume of such a cell will increase (i.e., the cell will swell). A biological sample may be diluted with a solution which may or may not include an osmoticant (such as, for example, glucose, sucrose, or other sugar; salts such as sodium, potassium, ammonium, or other salt; or other osmotically active compound or ingredient). In embodiments, an osmoticant may be effective to maintain the integrity of cells in the sample, by, for example, stabilizing or reducing possible osmotic gradients between the surrounding solution and the interior, or an interior compartment, of such cells. In embodiments, an osmoticant may be effective to provide or to increase osmotic gradients between the surrounding solution and the interior, or an interior compartment, of such cells, effective that the cells at least partially collapse (where the cellular interior or an interior compartment is less concentrated than the surrounding solution), or effective that the cells swell (where the cellular interior or an interior compartment is more concentrated than the surrounding solution).

For example, a biological sample may be measured or analyzed following dilution of a portion of the sample with a solution including dyes. For example, a biological sample may be measured or analyzed following dilution of a portion of the sample with a solution including antibodies or antibody fragments. For example, a biological sample may be measured or analyzed following dilution of a portion of the sample with a solution including particles. Particles added to a biological sample may serve as standards (e.g., may serve as size standards, where the size or size distribution of the particles is known, or as concentration standards, where the number, amount, or concentration of the particles is known), or may serve as markers (e.g., where the particles bind or adhere to particular cells or types of cells, to particular cell markers or cellular compartments, or where the particles bind to all cells in a sample).

For example, a biological sample may be measured or analyzed following processing which may separate one or more types of cells from another cell type or types. Such separation may be accomplished by gravity (e.g., sedimentation); centrifugation; filtration; contact with a substrate (e.g., a surface, such as a wall or a bead, containing antibodies, lectins, or other components which may bind or adhere to one cell type in preference to another cell type); or other means. Separation may be aided or accomplished by alteration of a cell type or types. For example, a solution may be added to a biological sample, such as a blood sample, which causes some or all cells in the sample to swell. Where one type of cell swells faster than another type or types of cell, cell types may be differentiated by observing or measuring the sample following addition of the solution. Such observations and measurements may be made at a time, or at multiple times, selected so as to accentuate the differences in response (e.g., size, volume, internal concentration, or other property affected by such swelling) and so to increase the sensitivity and accuracy of the observations and measurements. In some instances, a type or types of cells may burst in response to such swelling, allowing for improved observations and measurements of the remaining cell type or types in the sample.

Observation, measurement and analysis of a biological sample by cytometry may include photometric measurements, for example, using a photodiode, a photomultiplier, a laser diode, a spectrophotometer, a charge-coupled device, a camera, a microscope, or other means or device. Cytometry may include preparing and analyzing images of cells in a biological sample (e.g., two-dimensional images), where the cells are labeled (e.g., with fluorescent, chemiluminescent, enzymatic, or other labels) and plated (e.g., allowed to settle on a substrate) and imaged by a camera. The camera may include a lens, and may be attached to or used in conjunction with a microscope. Cells may be identified in the two-dimensional images by their attached labels (e.g., from light emitted by the labels).

An image of cells prepared and analyzed by a cytometer as disclosed herein may include no cells, one cell, or multiple cells. A cell or cell in an image of a cytometer, as disclosed herein, may be labeled, as disclosed above. A cell or cell in an image of a cytometer, as disclosed herein, may be labeled, as disclosed above, effective to identify the image, and the subject from whom the sample was taken.

In some embodiments, the assay system is configured to perform cytometry assays. Cytometry assays are typically used to optically, electrically, or acoustically measure characteristics of individual cells. For the purposes of this disclosure, "cells" may encompass non-cellular samples that are generally of similar sizes to individual cells, including but not limited to vesicles (such as liposomes), small groups of cells, virions, bacteria, protozoa, crystals, bodies formed by aggregation of lipids and/or proteins, and substances bound to small particles such as beads or microspheres. Such characteristics include but are not limited to size; shape; granularity; light scattering pattern (or optical indicatrix); whether the cell membrane is intact; concentration, morphology and spatio-temporal distribution of internal cell contents, including but not limited to protein content, protein modifications, nucleic acid content, nucleic acid modifications, organelle content, nucleus structure, nucleus content, internal cell structure, contents of internal vesicles (including pH), ion concentrations, and presence of other small molecules such as steroids or drugs; and cell surface (both cellular membrane and cell wall) markers including proteins, lipids, carbohydrates, and modifications thereof. By using appropriate dyes, stains, or other labeling molecules either in pure form, conjugated with other molecules or immobilized in, or bound to nano- or micro-particles, cytometry may be used to determine the presence, quantity, and/or modifications of specific proteins, nucleic acids, lipids, carbohydrates, or other molecules. Properties that may be measured by cytometry also include measures of cellular function or activity, including but not limited to phagocytosis, antigen presentation, cytokine secretion, changes in expression of internal and surface molecules, binding to other molecules or cells or substrates, active transport of small molecules, mitosis or meiosis; protein translation, gene transcription, DNA replication, DNA repair, protein secretion, apoptosis, chemotaxis, mobility, adhesion, antioxidizing activity, RNAi, protein or nucleic acid degradation, drug responses, infectiousness, and the activity of specific pathways or enzymes. Cytometry may also be used to determine information about a population of cells, including but not limited to cell counts, percent of total population, and variation in the sample population for any of the characteristics described above. The assays described herein may be used to measure one or more of the above characteristics for each cell, which may be advantageous to determine correlations or other relationships between different characteristics. The assays described herein may also be used to independently measure multiple populations of cells, for example by labeling a mixed cell population with antibodies specific for different cell lines. A microscopy module may permit the performance of histology, pathology, and/or morphological analysis with the device, and also facilitates the evaluation of objects based on both physical and chemical characteristics. Tissues can be homogenized, washed, deposited on a cuvette or slide, dried, stained (such as with antibodies), incubated and then imaged. When combined with the data transmission technologies described elsewhere herein, these innovations facilitate the transmission of images from a CMOS/CDD or similar detector to, e.g., a licensed pathologist for review, which is not possible with traditional devices that only perform flow cytometry. The cytometer can measure surface antigens as well as cell morphology; surface antigens enable more sensitive and specific testing compared to traditional hematology laboratory devices. The interpretation of cellular assays may be automated by gating of one or more measurements; the gating thresholds may be set by an expert and/or learned based on statistical methods from training data; gating rules can be specific for individual subjects and/or populations of subjects.

In some embodiments, the incorporation of a cytometer module into a point of service device provides the measurement of cellular attributes typically measured by common laboratory devices and laboratories for interpretation and review by classically-trained medical personnel, improving the speed and/or quality of clinical decision-making. A point of service device may, therefore, be configured for cytometric analysis.

Example 1

A sample of cells containing blood leukocytes including natural killer cells and neutrophils was obtained. The sample was treated with a fluorescently labeled identity binder (anti-CD16 binder), which binds to both natural killer cells and neutrophils. The sample was also treated with a nuclear dye (DRAQ5). The sample was imaged by fluorescence microscopy and dark field microscopy. The level of fluorescence and light side scatter of different cells in the sample was recorded and analyzed. Segmented images containing the anti-CD16 binder signal provided quantitative information on the fluorescence intensity of each cell (corresponding to the CD16 expression level), and also the size of each cell. The darkfield image provided quantitative information on the scatter properties of each cell. Images containing the DNA dye signal were segmented to determine the fluorescent intensity, size, and shape of the nucleus.

Figure 1B:
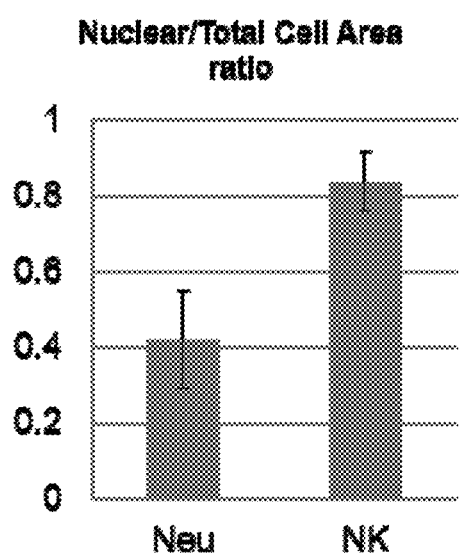
FIG. 1B shows a bar graph showing the ratio of nuclear area to total cell area of natural killer cells ("NK") and neutrophils ("Neu")
Figure 1C:
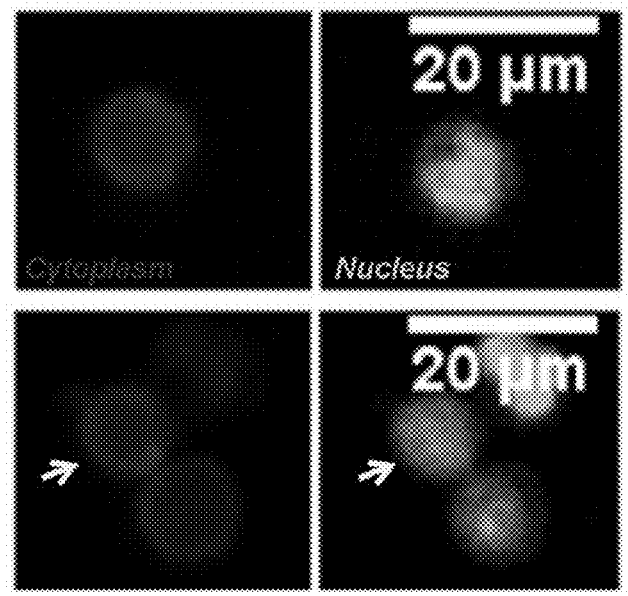
FIG. 1C shows natural killer cells stained with anti-CD16 antibody (left column) and a nuclear stain (right column)
Figure 1D:
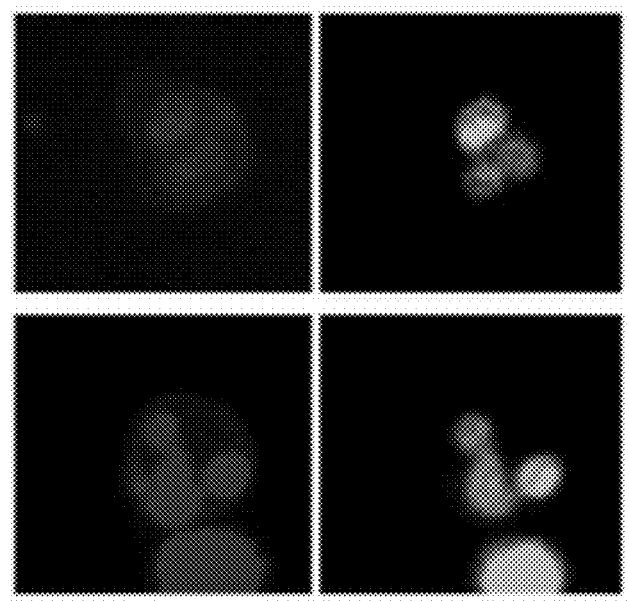
FIG. 1D shows neutrophils stained with anti-CD16 antibody (left column) and a nuclear stain (right column).

As shown in FIG. 1A, two major groupings cells were identified based on the measurement of CD16 fluorescence and light scatter of the different cells. The group of cells with bright/high CD16 fluorescence signal and high scatter (FIG. 1A, right circle) are neutrophils. The group of cells with intermediate CD16 fluorescence signal and low scatter (FIG. 1A, left circle) are natural killer cells. While the measurement of fluorescence and light scatter of the different cells provides enough information to classify most cells in the sample as either natural killer cells or neutrophils, for some cells, measurement of these attributes does not provide enough information to classify the cells with a high degree of accuracy. For example, the measurement of fluorescence and light scatter of cells does not provide enough information to accurately classify the small group of cells in the smallest circle in FIG. 1A (i.e. the middle circle). In order to identify whether the cells in the smallest circle were natural killer cells or neutrophils, images of the nuclear (DRAQ5) and total cell (anti-CD16) staining of these were examined Quantitative measurements of the area of the nucleus and the total cell volume of the cells were obtained, and the ratio of nuclear area to total cell area was determined. As shown in FIG. 1B, there is a clear difference in the ratio of nuclear area to total cell area between natural killer cells ("NK") and neutrophils ("Neu"). Thus, the use of quantitative microscopy to examine multiple attributes of cells in the sample was used to allow for unambiguous classification of cells. FIG. 1C shows images of natural killer cells from the smallest circle in FIG. 1A. All images have the same length scale. The images on the left are cells stained for total cell area (anti-CD16), and the images on the right are the same cells with just nuclear staining (DRAQ5). The images on the top and bottom row are different examples of the natural killer cells. FIG. 1D shows images of neutrophils from the smallest circle in FIG. 1A. All images have the same length scale. The images on the left are cells stained for total cell area, and the images on the right are the same cells with just nuclear staining. The images on the top and bottom row are different examples of the natural killer cells.

In addition, the nucleus of a neutrophil has a distinctive multi-lobed shape, whereas the nucleus of a natural killer cell (and other lymphocytes) is round, even, and smooth. Image segmentation algorithms may be used to identify and classify cells based on the shape of the nucleus itself.

Example 2

Figure 2A:
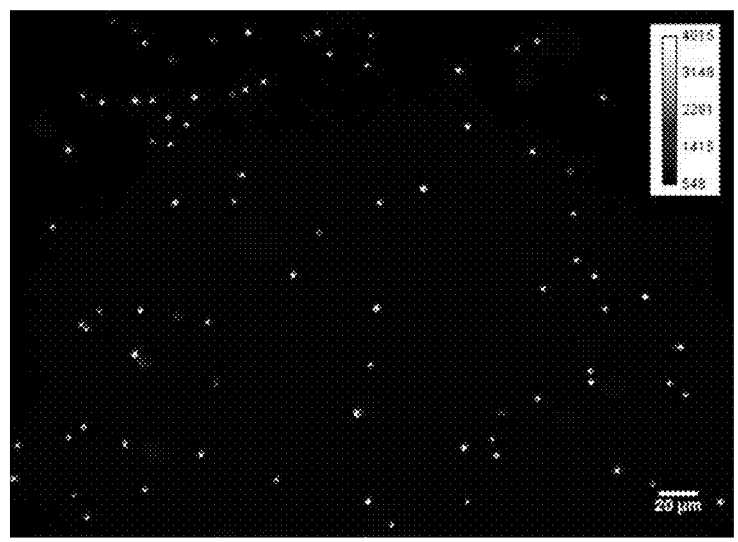
FIG. 2A shows platelets labeled with fluorescently conjugated CD41 and CD61 antibodies (bright dots)
Figure 2B:
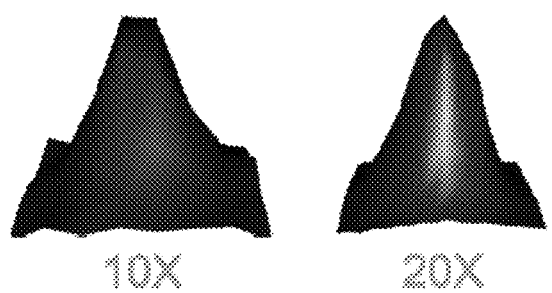
FIG. 2B shows intensity distribution of images of fluorescently labeled platelets at 10× (left) and 20× (right) magnification.
Figure 2C:
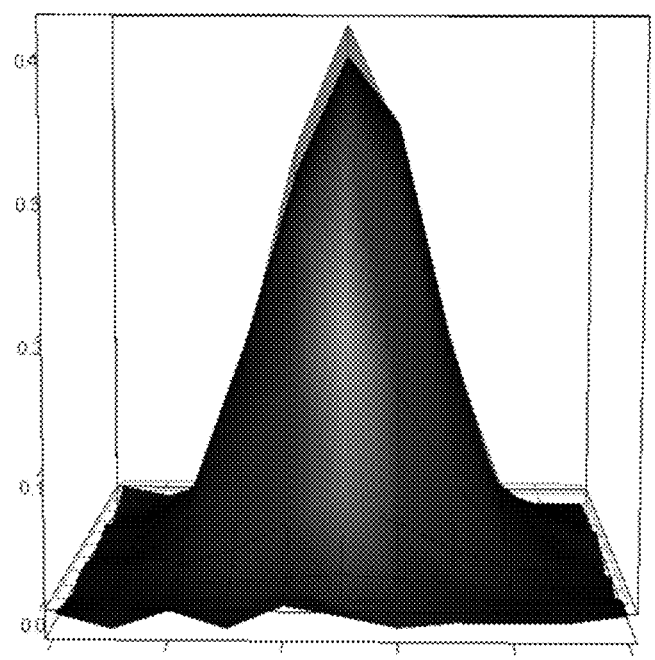
FIG. 2C shows intensity distribution of an image of a fluorescently labeled platelet showing measured intensity (light grey) and curve fit to the measured intensity (dark grey).

A sample containing platelets was obtained. The platelets were labeled with fluorescently conjugated anti-CD41 and anti-CD61 antibodies. Beads having a diameter of 3 µm were also added to the sample. The sample was imaged at 10× and 20× magnifications (FIG. 2A). The intensity of fluorescence distribution for individual platelets was measured (from both antibodies), and determined have a Gaussian shape (FIG. 2B). The measured values of fluorescence of individual platelets was plotted, and a fit for the intensity distribution was determined (FIG. 2C). In FIG. 2C, the grey line is the measured fluorescence intensity across an individual platelet, and the black line is the fit. Parameters of the fit, such as the mean of the Gaussian, the variance, the volume, the width, and the area of the base, etc., can be evaluated as predictors of platelet volume. The volume of the Gaussian and the width of the fit have been determined to correlate closely with mean platelet volume.

For the above measurements, the 3 µm beads served as references and fiducials for controlling variance in accurately determining the best plane of focus, and the effect of this variance on the measurement of volume.

Figure 3:
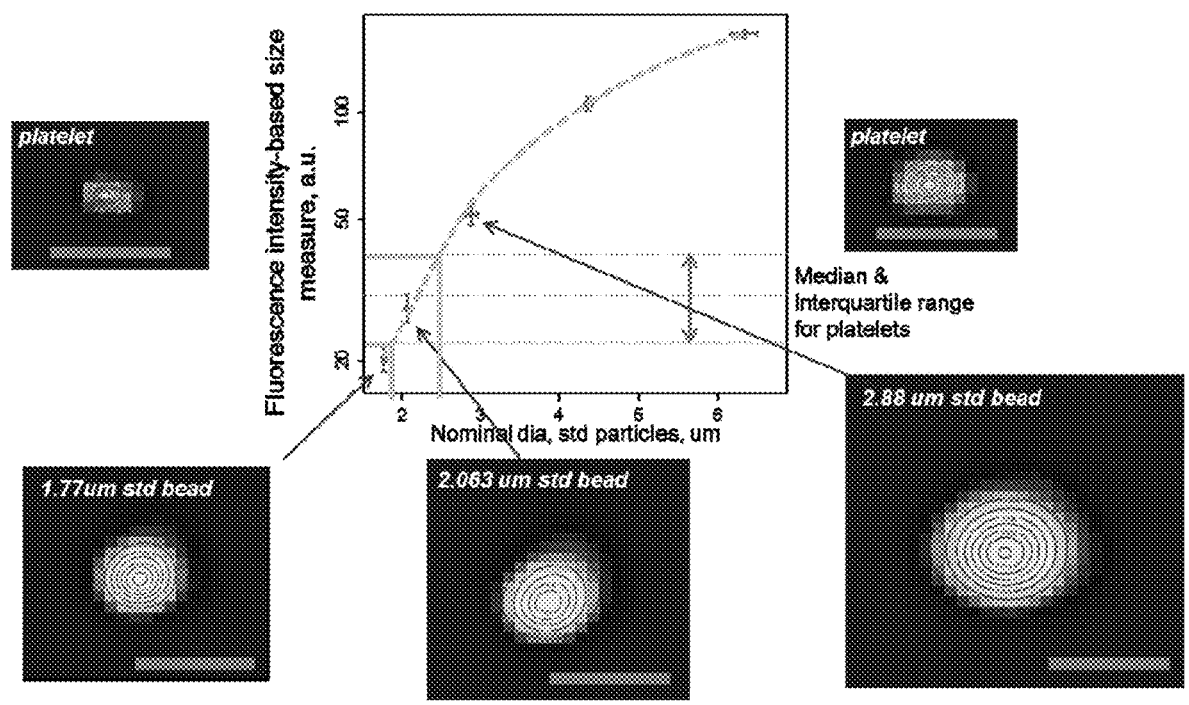
FIG. 3 shows: a plot of curve of showing the relationship between the nominal diameter of standard particles in μm (x-axis) and fluorescence intensity-based size measure in a.u. (y-axis). The figure also shows representative beads at different points along the curve.

In addition, platelet size estimated based on fitting a 2D model can be calibrated to be in the normal range (FIG. 3).

Example 3

Figure 4:
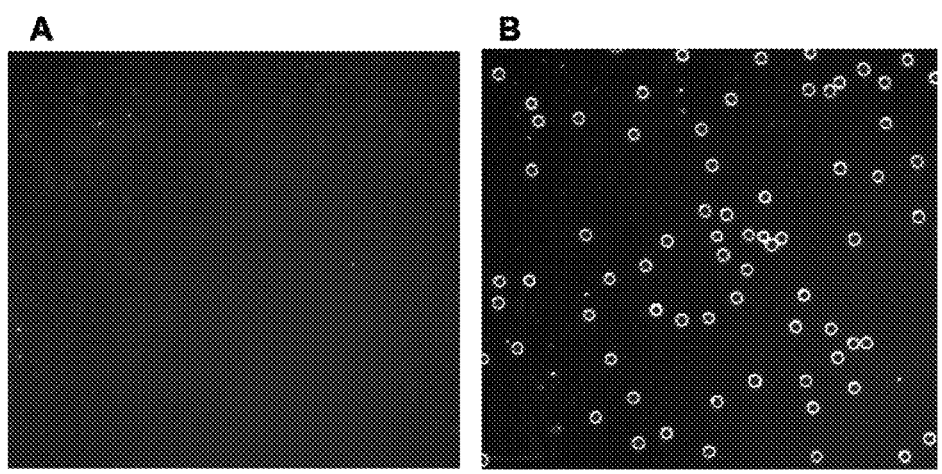
FIG. 4 shows: sphered red blood cells imaged by dark field microscopy in cuvettes that allow (A) only epi-illumination, and (B) a mixture of epi- and trans-illumination.

A sample containing red blood cells ("RBCs") was obtained. The RBCs were treated with a low concentration of a surfactant (DDAPS or SDS), causing the RBCs to assume a sphere-like shape. The RBCs were imaged by dark field microscopy in two different cuvettes: (A) a cuvette that allowed only pure epi-illumination (FIG. 4A); and (B) a cuvette that allowed a mixture of both epi and trans-illumination (FIG. 4B). The RBCs were much more visible in the cuvette that allowed a mixture of both epi and trans-illumination over the cuvette that allowed only pure epi-illumination (FIG. 4).

Example 4

A sample containing neutrophils was obtained. In neutrophils, the shape and chromatin morphology of the nucleus may indicate whether it is an immature "band" neutrophil or a mature "segmented" neutrophil. Band neutrophils are immature neutrophils that have recently emerged from the bone marrow. An increase in the proportion of band neutrophils may indicate an ongoing infection or inflammation.

The sample was mixed with a fluorescently labeled anti-CD16 antibody, which recognizes CD16, a cell surface receptor on neutrophils. The sample was also stained with a fluorescent nuclear dye. The sample was imaged by fluorescence microscopy, to obtain both nuclear staining and CD16 staining data from the cells. Band neutrophils generally have similar expression levels of CD16 as mature segmented neutrophils, and thus cannot be distinguished by virtue of fluorescence intensity from CD16 staining alone.

Figure 5A:
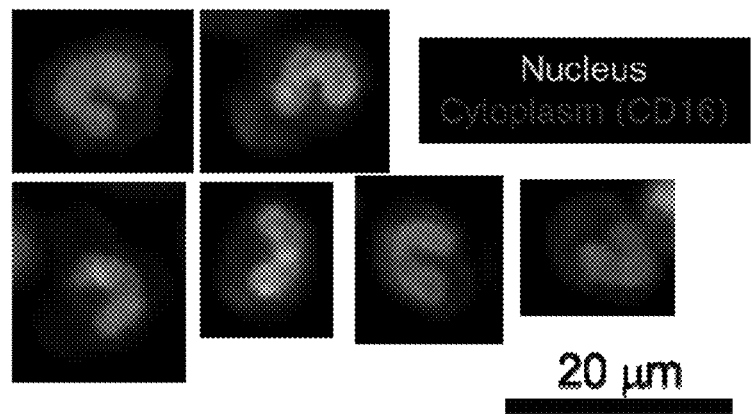
FIG. 5A shows putative band neutrophils stained with anti-CD16 antibody and a nuclear stain.
Figure 5B:
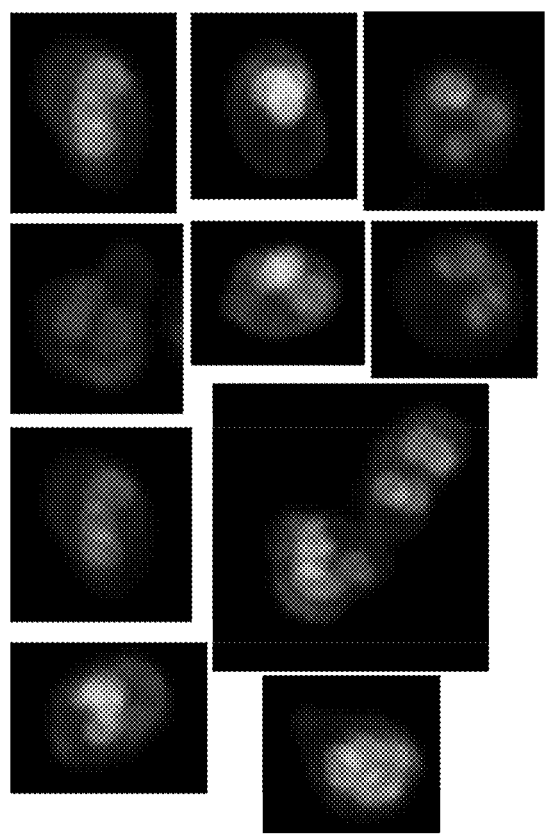
FIG. 5B shows putative segmented neutrophils stained with anti-CD16 antibody and a nuclear stain.

Image analysis including image segmentation is used to recognize nuclear staining and morphologies of band neutrophils and segmented neutrophils, thereby allowing classification of the cells. The size, shape, and fluorescence intensity of the nucleus of cells are examined. In addition, the nuclei are analyzed to determine the number of lobes (peaks in intensity within the nuclear area), distance between the lobes of the nucleus, and the changes in curvature (second derivative) of the nuclear outline. FIG. 5A shows representative images of band neutrophils. In these images, the nucleus appears as a light grey, and the cell cytoplasm appears as a darker grey. As neutrophils differentiate through the myeloid lineage, they develop a characteristic "U" shaped nucleus prior to reaching full maturity. FIG. 5B shows representative images of segmented neutrophils. In these images, the nucleus appears as a light grey, and the cell cytoplasm appears as a darker grey. The nuclei of segmented neutrophils have multiple segments/lobes (typically about 3-5). Thus, this analysis supports identification and quantification of different subpopulations of neutrophils in the blood.

Example 5

A sample of cells from a subject with chronic lymphocytic leukemia (CLL) is obtained. The objective is to quantify the extent of CD5 expression on B-cells from the subject. Anti-CD20 antibodies are selected as the binder for B-cells. Anti-CD20 antibodies labeled with a first colored fluorphore are mixed with the sample. After an appropriate incubation time, the sample is washed and the unbound anti-CD20 antibodies are removed. The sample is exposed to a light source capable of exciting the first fluorophore, and fluorescent signal is measured using a spectrophotometer. Based on the fluorescent signal, the approximate concentration of B-cells in the sample is determined. The determined approximate concentration of B-cells is, in fact, within 1.5 fold of the true concentration of B-cells in the sample.

Based on the approximate concentration of B-cells in the sample, an appropriate amount of anti-CD5 binder is added to the sample so that a proportional relationship between CD5 expression and CD5 fluorescence is maintained. The anti-CD5 binder is coupled to a second fluorophore, which has a different peak excitation wavelength than the first fluorophore (attached to the anti-CD20 binder). The anti-CD5 antibody is added to the sample, and then individual cells of the sample are exposed to a light source capable of exciting the second fluorophore, and fluorescent signal from individual cells is measured. Based on the fluorescent signal from cells, the average amount of CD5 in B-cells in the sample is determined.

Although this example is described in the context of CD5, it should be understood that this concept of obtaining an approximate count to guide an addition of a desired amount of material for use in a subsequent step, is not limited to CD5 and use of this concept with other types of cells, analytes, or objects is not excluded.

Example 6

Blood cells may be imaged, identified, and quantified according to the methods disclosed herein. For example, two-dimensional images of cells in a biological sample, where the cells are labeled (e.g., with fluorescent, chemiluminescent, enzymatic, or other labels) and plated (e.g., allowed to settle on a substrate) and imaged by a camera, may be prepared and analyzed as described in the present example. The camera may include a lens, and may be attached to or used in conjunction with a microscope. Cells may be identified in the two-dimensional images by their attached labels (e.g., from light emitted by the labels).

80 microliters of whole blood obtained from a fingerstick was loaded into a capped sample container preloaded with 2 mg/ml EDTA. In this instance an enclosed sample container was used (with a removable or pierceable cap); it will be understood that any suitable vessel for holding such a small volume sample may be used, including, but not limited to, a capped vessel or an uncapped vessel. The sample container was centrifuged at 1200×g for 5 minutes, to separate the blood cells from the blood plasma. Centrifugation of the sample container resulted in the separation of the blood sample in the sample container into two major components (from top of the sample container to the bottom): 1) blood plasma and 2) packed blood cells. This process ensures that no droplets of blood remain isolated, but coalesce with the main body of the liquid. In addition, this process separates the cells from elements of the plasma thus reducing metabolism and allowing for longer storage of the sample.

The centrifuged sample container was loaded into a cartridge containing multiple fluidically isolated reagents, tips, and a cytometry cuvette. The cartridge contained all the reagents required for the assay. The cartridge was loaded into a device equipped with at least a centrifuge, a pipette and a platform to load the cuvette. The pipette in the device has a plurality of nozzles, some nozzles being of a different size than some other nozzles.

Inside the device, a nozzle on the pipette was lowered on a cuvette carrier tool causing it to engage a corresponding hole on the carrier tool. This tool was subsequently moved to the cartridge and lowered on the cytometer cuvette. Pins on the tool were then able to engage corresponding holes on the cuvette and pick it up. The cuvette was transferred to a loading station elsewhere in the device.

Next, inside the device, a larger nozzle of the pipette was lowered into the cartridge to engage a pipette tip stored in the cartridge. The pipette and tip together were then used to mix the cells and plasma in the sample container by positioning the pipette tip within the sample in the sample container and repeatedly aspirating material into and dispensing material from the tip. Once the cells were resuspended in the plasma so that the whole blood sample was thoroughly mixed, 5 microliters of the mixed whole blood was aspirated to provide an aliquot for measurements of properties of the blood sample. This 5 microliter aliquot was used for measurements directed to the red blood cells and platelets in the sample. As discussed below, a portion of the sample remaining after removal of this 5 microliter aliquot was used for measurements directed at white blood cells in the sample.

The 5 microliters of whole blood was dispensed into a vessel containing a mixture of phosphate buffered saline and 2% by weight of bovine serum albumin, to dilute the whole blood twenty-fold (resulting in 100 microliters of diluted sample). After mixing vigorously, 5 microliters of this sample was transferred to another vessel containing a cocktail of labeling antibody reagents: anti-CD235a conjugated to Alexa Fluor® 647 (AF647), anti-CD41 and anti-CD61 conjugated to phycoerythrin (PE). The mixture was incubated for 5 minutes. Subsequently, 10 microliters of this mixture was mixed with 90 microliters of a buffer containing a zwitterionic surfactant at <0.1% by weight. The surfactant molecules modify bending properties of the red cell membrane such that all cells assume a stable spherical shape. This transformation is isovolumetric as the buffer used is isotonic with cytoplasm; thus no osmotically driven exchange of fluid can occur across the cell membrane. After incubating this for another 2 minutes, 30 microliters of this solution was mixed with a solution containing glutaraldehyde, a fixative and non-fluorescent beads of 10 um diameter. The mixture had a final concentration of 0.1% glutaraldehyde and 1000 beads per microliter. Glutaraldehyde rapidly fixes cells thus preventing cell lysis and other active biological processes.

In this non-limiting example, the pipette then engaged a tip in the cartridge, aspirated 7 microliters of the above mixture of and loaded the 7 microliters into a channel within the cuvette placed on a platform with the carrier tool. After the mixture was loaded in into cuvette, the pipette aspirated 10 microliters of mineral oil from a vessel in the cartridge, and placed a drop of mineral oil on both open ends of the loaded channel of the cuvette. Hexadecane was added to the ends of the open channel to prevent evaporation of liquid from the loaded cuvette channel (mineral oil would also work). Next, the device-level sample handling apparatus engaged the cuvette carrier/cuvette combination, and transported the cuvette carrier/cuvette combination from the module containing the cartridge to the cytometry module of the device. At the cytometry module, the device-level sample handling apparatus placed the cuvette carrier/cuvette combination on the microscopy stage of the cytometry module. The time required for these operations, in addition to a 2 minute wait time allowed the swelled cells to settle to the floor of the cuvette prior to imaging.

After the cuvette carrier/cuvette was placed on the microscopy stage, the stage was moved to pre-determined location so that the optical system of the cytometer could view one end of the channel containing the sample. At this location, the optical system relayed images of the sample acquired with darkfield illumination from a ringlight. These images coupled with actuation of the optical system on an axis perpendicular to the plane of the cuvette were used to find the plane of best focus. Once focused, the optical system was used to acquire fluorescence images of the sample at different wavelengths, commensurate with the fluorophores that were being used. For example, to visualize red blood cells that had been labeled with anti-CD235 conjugated to Alexa Fluor® 647, a red (630 nm wavelength) light source was used to excite the sample and wavelengths between 650 nm and 700 nm were used to image the sample. A combination of a polychroic mirror and a bandpass emission filter was used to filter out unwanted wavelengths from the optical signal. Since the cells had settled on the floor of the cuvette, images at a single plane of focus were sufficient to visualize all cells in the region.

Data from the images was processed by a controller associated with the sample processing device. The image processing algorithms employed here utilized fluorescence images of cells to detect them using a combination of adaptive thresholding and edge detection. Based on local intensity and intensity gradients, regions of interest (RoI) were created around each cell. Using darkfield images, beads in the sample were also identified and RoIs were created around the beads. All the RoIs in each field of view were enumerated and their intensity in each image of that field of view were calculated. The information output by the image processing algorithm consisted of shape or morphometric measurements and fluorescence and darkfield intensities for each RoI. This information was analyzed using statistical methods to classify each object as either a red blood cell (positive for CD235a, but negative for CD41/CD61), a platelet (positive for CD41/CD61 and negative CD235a) or a bead. The shape descriptors such as perimeter, diameter and circularity were used to calculate the volume of each red blood cell and platelet. Since the beads were added at a known concentration, the average ratio of beads to cells over the whole channel was used to calculate cell concentration in terms of cells/microliter. Based on the steps performed for processing the sample, this concentration was corrected for dilution to arrive at concentration of cells in the original whole blood sample. The following quantities were calculated from a sample: 1) number of red blood cells in the cuvette; 2) average volume of red blood cells in the cuvette; 3) red blood cell distribution width (RDW) of red blood cells in the cuvette; 4) number of platelets in the cuvette; and 5) average volume of platelets in the cuvette. Based on these calculations, the following was calculated for the original blood sample.

| Measured Value | Result | Exemplary Range |
| --- | --- | --- |
| Concentration of red blood cells (million cells per microliter) | 4.8 | 4-6 |
| Mean volume of red blood cells, femtoliter | 88 | 80-100 |
| red blood cell distribution width (RDW), (%) | 12 | 11-14.6 |
| Concentration of platelets (thousand cells per microliter) | 254 | 150-400 |
| Mean volume of platelets, femtoliter | 10.4 | 7.5-11.5 |

After removal of the 5 microliter aliquot used for analysis of RBC and platelet information, the remaining 75 microliters of sample was used to analyze the white blood cell population of the whole blood sample. The remaining 75 microliters of whole blood had also been mixed by repeatedly aspirating and dispensing the sample within the same the vessel by the pipette. Approximately 40 microliters of the remaining 75 microliters of mixed whole blood was aspirated into a pipette tip, and transferred by the pipette to a centrifuge tube in the cartridge. The centrifuge tube containing the blood sample was engaged by the pipette, and transferred to and deposited in a swinging bucket in a centrifuge within the module. The centrifuge was spun to provide 1200×g for 3 minutes, separating the blood into EDTA-containing plasma as the supernatant and packed cells in the pellet.

After centrifugation, the centrifuge tube was removed from the centrifuge and returned to the cartridge. The plasma supernatant was removed by the pipette and transferred to a separate reaction vessel in the cartridge. From a reagent vessel in the cartridge, 16 microliters of resuspension buffer was aspirated by the pipette, and added to the cell pellet in the centrifuge tube. The pipette then resuspended the cell pellet in the resuspension buffer by repeatedly aspirating and dispensing the mixture in the centrifuge tube. Next, the pipette aspirated 21 microliters of the resuspended whole blood and added it to another vessel containing 2 microliters of anti CD14-Pacific Blue™ and DRAQ5®, mixed, and incubated for 2 minutes. Twenty microliters of this mixture was then added to 80 microliters of a lysis buffer. The lysis buffer is a solution of a gentle surfactant such a saponin in conjunction with a fixative such as paraformaldehyde. The detergent causes a large number of holes to be formed in the membranes of cells. Red blood cells, due to their unique membrane properties, are particularly susceptible to this hole formation and lyse completely, their contents leaking out into the liquid around. Presence of the fixative prevents unintentional lysis of the white blood cells. Platelets also remain unlysed. The purpose of this step is to remove red blood cells from the mixture as they outnumber white blood cells by about 1000:1. Platelets do not interfere with imaging and hence are irrelevant to this process. The lysis buffer also contained 10 μM non-fluorescent beads at a known concentration.

After a 5 minute incubation, the vessel was spun again at 1200×g for 3 minutes. The supernatant was aspirated by a pipette tip, removing the red blood cell ghosts and other debris, and deposited into a waste area in the cartridge. Approximately 15 microliters of liquid with packed white blood cells were present in the cell pellet.

In order to determine a rough approximation of the number of white blood cells present in the cell pellet, the pipette first resuspended the white blood cells in the vessel and then aspirated the liquid for transport to and inspection by a spectrophotometer. The white blood cell suspension was illuminated with light at a wavelength of 632 nm, which is the excitation wavelength for Alexa Fluor® 647 dye and DRAQ5®. The light emitted by the cell suspension was filtered by a 650 nm long pass filter and measured in the spectrophotometer. This measurement was correlated with previously generated calibration curve to estimate a rough concentration of white blood cells in the cell suspension. Typically, cell concentrations ranged from about 1000 cells per microliter to about 100,000 cells per microliter. This estimate was used to calculate an appropriate dilution factor to ensure that the concentration of cells in the cuvette was constrained to within a two-fold range around a pre-defined target concentration. The purpose of this step was to ensure that cells are not present at too high or too low a density on the cuvette. If the cell density is too high, the accuracy of image processing algorithms is compromised, and if the cell density is too low, an insufficient number of cells are sampled.

Based on the dilution factor calculated in the above step, a diluent containing labeled antibodies against CD45 (pan-leukocyte marker), CD16 (neutrophil marker) and CD123 (basophil marker) was added to the cell suspension and mixed.

Once the cuvette in complex with cuvette carrier was placed on the cuvette carrier block, 10 microliters of the mixture of white blood cells resuspended in cytometry buffer was loaded into each of two channels in the cuvette. After the mixture was loaded into channels of the cuvette, the pipette aspirated 10 μl of hexadecane from a vessel in the cartridge, and placed a drop of mineral oil on both open ends of both channels in the cuvette loaded with white blood cells.

Next, the device-level sample handling apparatus engaged the cuvette carrier/cuvette combination, and transported the cuvette carrier/cuvette combination from the module containing the cartridge to the cytometry module of the device. At the cytometry module, the device-level sample handling apparatus placed the cuvette carrier/cuvette combination on the microscopy stage of the cytometry module. After the cuvette carrier/cuvette was placed on the microscopy stage, the two channels of the cuvette containing white blood cells were imaged as described above for the RBC/platelet mixture.

Figure 9A:
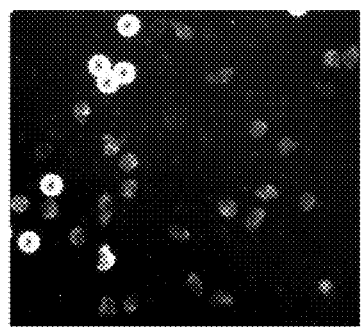
FIGS. 9A-9F are composite image which shows representative images of blood cells taken from whole blood, using different imaging techniques and dyes.
Figure 9B:
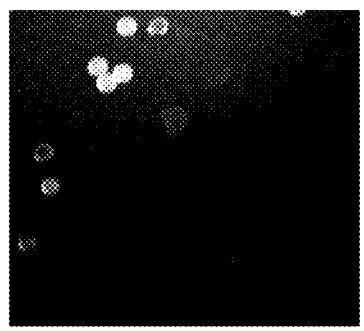
Figure 9C:
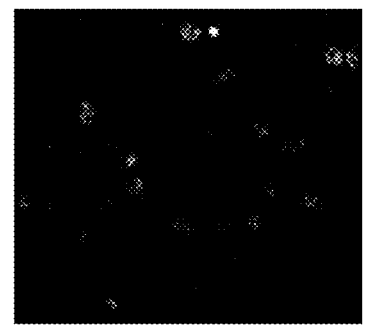
Figure 9D:
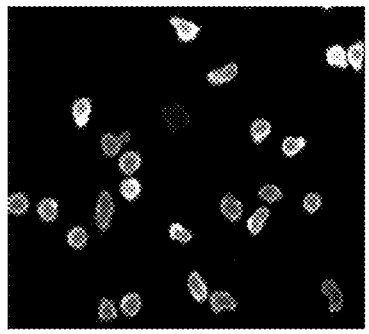
Figure 9E:
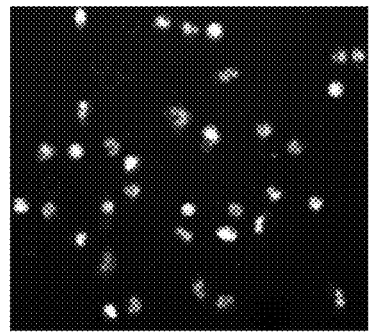
Figure 9F:
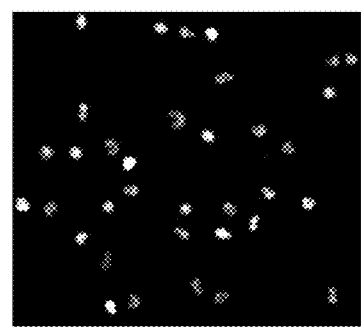

Darkfield images of the white blood cells were used to count the numbers of cells in a field (as shown in FIG. 9A). Cell surface markers were used to determine the cell type of individual white blood cells in an image; for example, CD14 marks monocytes; CD123 marks basophils; CD16 marks neutrophils; and CD45-AF647 were used to mark all leukocytes (FIGS. 9B-9E). The nuclear stain Draq5 was used to mark cell nuclei, and so to differentiate nucleated cells (such as white blood cells) from mature red blood cells, which have no nucleus (FIG. 9F).

The image processing algorithms employed here utilized fluorescence images of cells to detect them using a combination of adaptive thresholding and edge detection. Based on local intensity and intensity gradients, boundaries of regions of interest (RoI) were created around each cell. Using darkfield images, beads in the sample were also identified and RoI boundaries were created around the beads. All the RoIs in each field of view were enumerated and their intensity in each image of that field of view were calculated. The information output by the image processing algorithm consisted of shape or morphometric measurements and fluorescence and darkfield intensities for each RoI. This information was analyzed using statistical methods to classify each object as a lymphocyte, monocyte, basophil, eosinophil, neutrophil or a bead. Based on enumeration of cells of different types, the corresponding bead count and the dilution ratio implemented during sample processing, an absolute concentration of cells per microliter of original whole blood was calculated. This was calculated for all white blood cells and each subtype, and reported as both absolute concentration (cells per microliter) and proportion (%).

Figure 10:
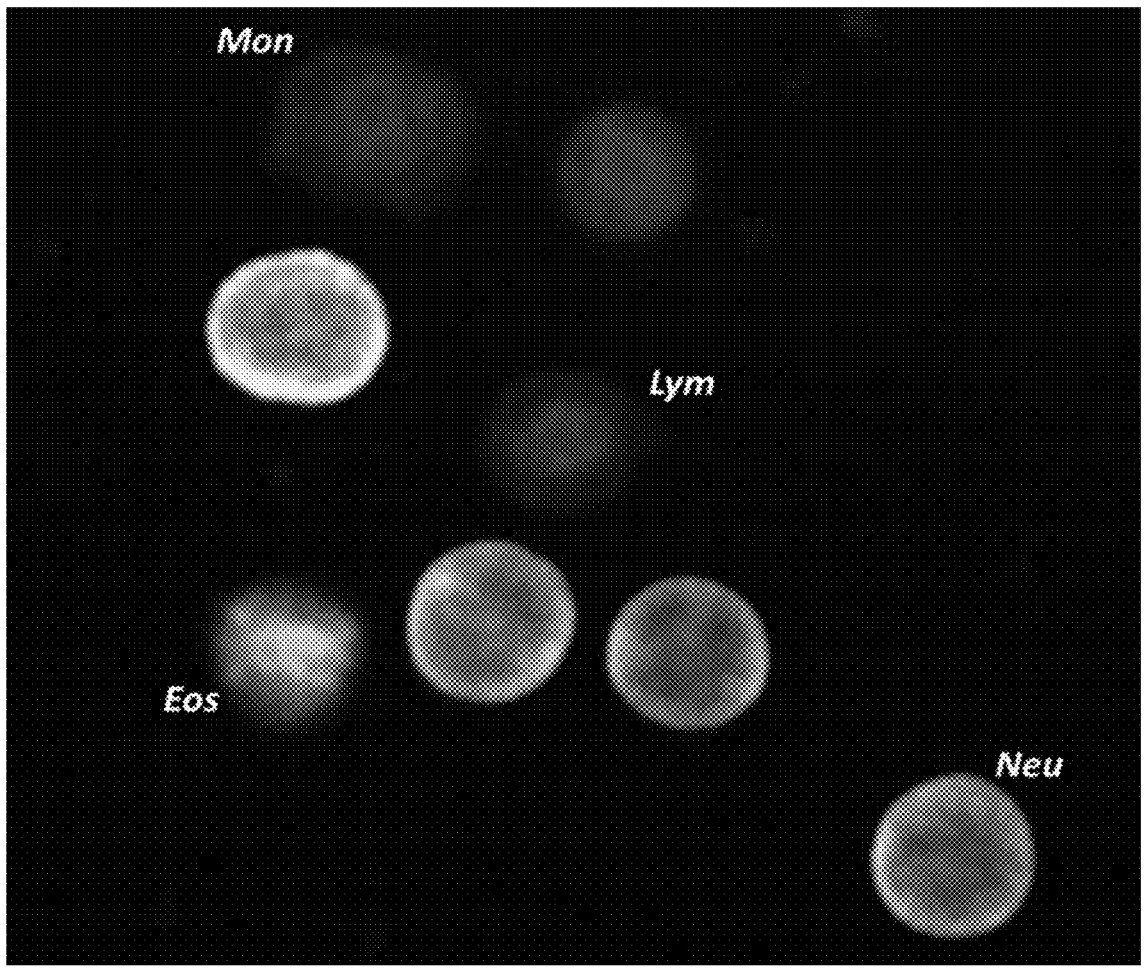
FIG. 10 is composite image which shows representative images of blood cells taken from whole blood, showing a monocyte, a lymphocyte, an eosinophil, and a neutrophil.

Examples of images and plots of results of such measurements are presented in FIGS. 9, 10, and 11.

FIG. 9 shows representative images of blood cells from a sample of whole blood; these images were taken using different imaging techniques and dyes. The image shown in FIG. 9A was taken of cells from whole blood using darkfield illumination. The image shown in FIG. 9B was taken of cells from whole blood showing fluorescence from anti-CD14 antibodies labeled with Pacific Blue dye; the fluorescent cells are monocytes. The image shown in FIG. 9C was taken of cells from whole blood showing fluorescence from anti-CD123 antibodies labeled with PECy5 dye; the fluorescent cells are basophils. The image shown in FIG. 9D was taken of cells from whole blood showing fluorescence from anti-CD16 antibodies labeled with PE dye; the fluorescent cells are neutrophils. The image shown in FIG. 9E was taken of cells from whole blood showing fluorescence from anti-CD45 antibodies labeled with AF647 dye; all leukocytes fluoresce under these conditions. The image shown in FIG. 9F was taken of cells from whole blood dyed with DRAQ5® to stain cell nuclei. Thus, leukocytes and platelets are stained and fluoresce under these conditions, but red blood cells (lacking nuclei) are not stained and do not fluoresce.

FIG. 10 shows a representative composite image of cell-types in whole blood from images acquired according to the methods disclosed herein. Images of a monocyte (labeled and seen in the upper left quadrant of the figure, with a reddish center surrounded by a blue-purple ring), a lymphocyte (labeled and seen in the center of the figure, with a bright red center surrounded by a dimmer red ring), an eosinophil (labeled and seen in the lower left quadrant of the figure, with a green center surrounded by a red border), and a neutrophil (labeled and seen in the lower right quadrant of the figure, with a green center surrounded by a yellow and green border) are shown in the figure.

It is of interest to identify and quantify various cell types found in such blood samples. There may be multiple ways to approach such a classification process, which, in some embodiments, may be considered as being a statistical problem for multi-dimensional classification. It will be understood that a wide variety of methods are available in the field to solve these types of classification problems. A particular embodiment of such an analysis is provided below.

FIG. 11 shows plots of various cell types identified and quantified by the cytometric assays described in this example. FIG. 11A shows a plot of spots (cells) by intensity of the marker FL-17 (anti-CD14 antibody labeled with pacific blue dye) versus intensity of FL-9 (darkfield scatter signal) to identify monocytes. FIG. 11B shows a plot of spots (cells) by intensity of the marker FL-19 (anti-CD123 antibody labeled with PE-CY5 dye) versus intensity of the marker FL-15 (anti-CD16 labeled with PE dye) to identify basophils. FIG. 11C shows a plot of spots (cells) by intensity of the marker FL-15 (anti-CD16 labeled with PE dye) versus intensity of the marker FL-11 (anti-CD45 antibody labeled with AF647 dye) to identify lymphocytes. FIG. 11D shows a plot of spots (cells) by intensity of the marker FL-15 (anti-CD16 labeled with PE dye) versus intensity of FL-9 (darkfield scatter signal) to identify neutrophils and eosinophils.

Figure 11A:
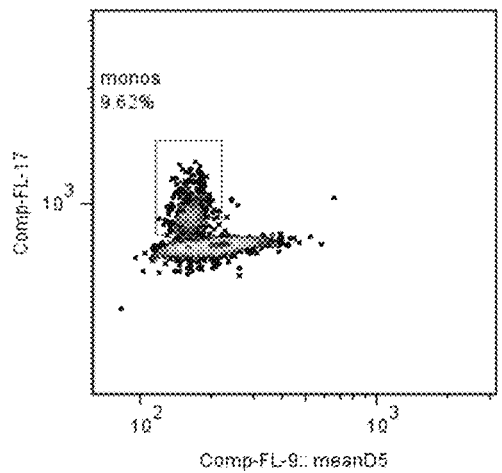
FIGS. 11A-11D show plots of fluorescence detected on cells labeled with different markers (labeled antibodies directed at different cell-surface or other markers); such multiple labeling is useful for identifying cells.
Figure 11B:
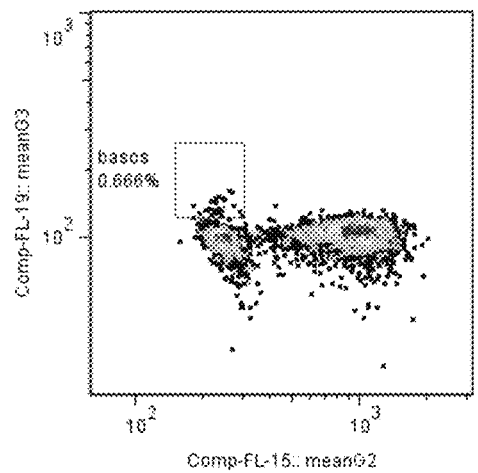
Figure 11C:
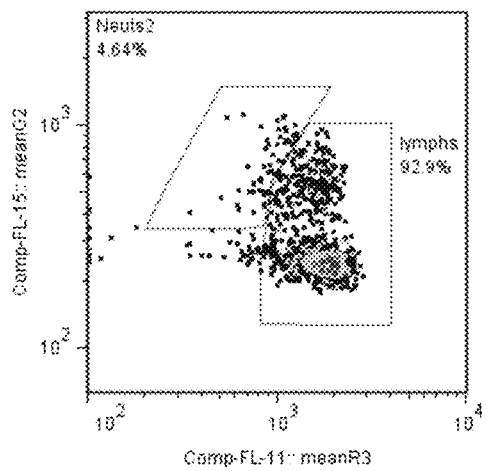
Figure 11D:
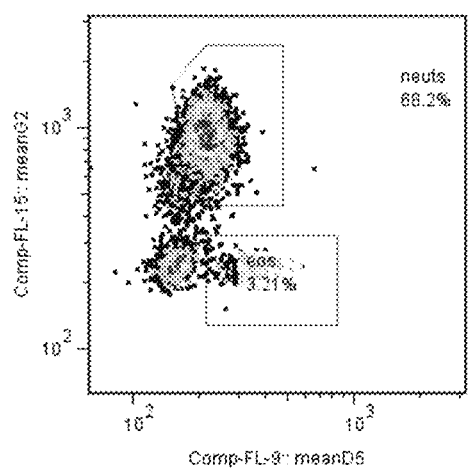

The initial identification of monocytes (9.6%, as shown in FIG. 11A) is used to guide the subsequent identification of basophils (0.68%, as shown in FIG. 11B). The identification of monocytes and basophils as shown in FIGS. 11A and 11B is used to guide the subsequent identification of neutrophils and eosinophils (68% neutrophils, 3.2% eosinophils, of the WBCs shown in FIG. 11D). Finally, lymphocytes are identified as shown in FIG. 11C (93% of the WBCs plotted in FIG. 11C, corresponding to 18% of the cells in the original sample).

The present methods correlate well with other methods. Counts of white blood cells, red blood cells, and platelets were made with samples of EDTA-anti coagulated whole blood. The white blood cells were further counted to determine the numbers of neutrophils, monocytes, and lymphocytes in the sample. In the measurements shown in FIG. 12, EDTA-anti coagulated whole blood samples were split into two, and one part of the samples were run on the system disclosed herein, using the methods disclosed herein. The other part of the samples was run on an Abbott CELL-DYN Ruby System (Abbott Diagnostics, Lake Forest, Ill., USA), a commercial multi-parameter automated hematology analyzer. A comparison of the results obtained with both methods is shown in FIG. 12.

Figure 12A:
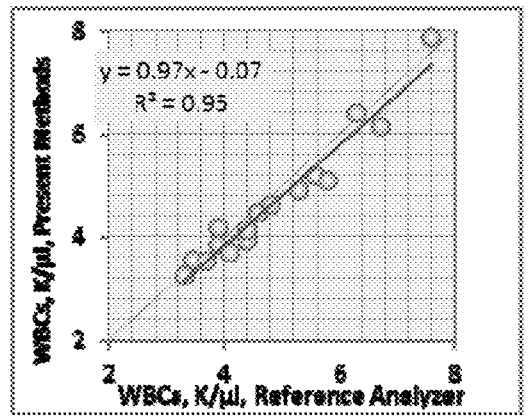
FIGS. 12A-12F show comparisons of cell counts (measured from aliquots of the same blood sample) obtained by the present methods, and those obtained by other methods (using a commercial blood analyzer).
Figure 12B:
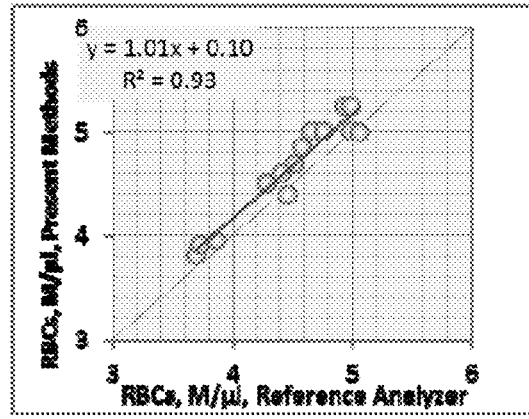
Figure 12C:
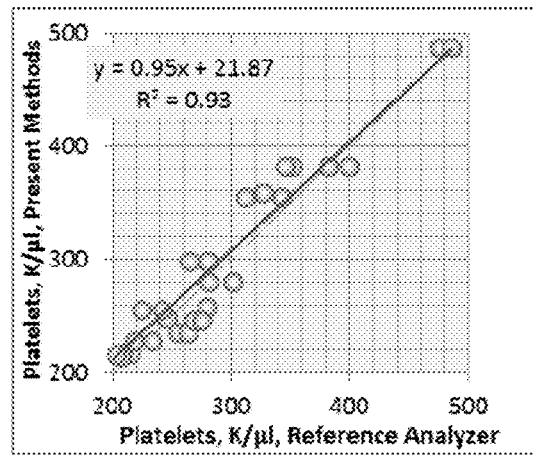
Figure 12D:
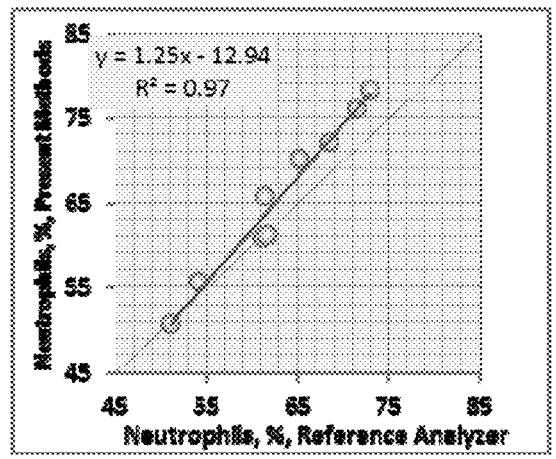
Figure 12E:
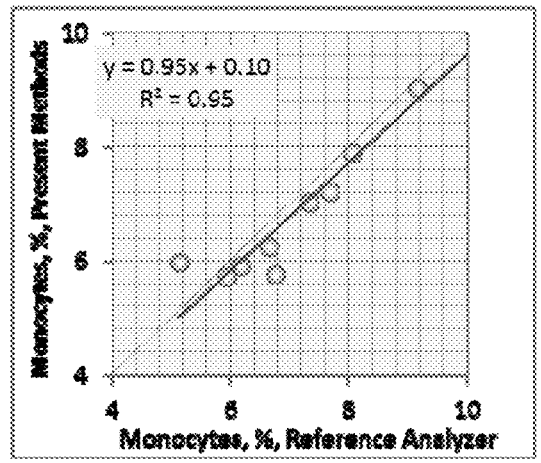
Figure 12F:
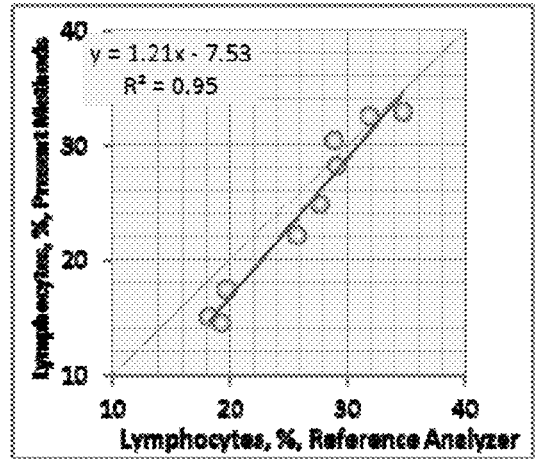

As shown in FIGS. 12A-12C, the numbers of white blood cells ("WBCs", FIG. 12A), red blood cells ("RBCs", FIG. 12B) and platelets (FIG. 12C) measured by the present methods correlate well with the numbers of WBCs, RBCs, and platelets measured by other methods in corresponding aliquots of the same samples as were analyzed by the present methods. As shown in FIGS. 12D-12F, the numbers of neutrophils, monocytes, and lymphocytes measured by either method were very similar, and correlated well with each other.

In aspects of the term as used herein, the term "cytometry" refers to observations, analysis, methods, and results regarding cells of a biological sample, where the cells are substantially at rest in a fluid or on a substrate. Cells detected and analysed by cytometry may be detected and measured by any optical, electrical or acoustic detector. Cytometry may include preparing and analyzing images of cells in or from a biological sample (e.g., two-dimensional images). The cells may be labeled (e.g., with fluorescent, chemiluminescent, enzymatic, or other labels) and plated (e.g., allowed to settle on a substrate) and, typically, imaged by a camera. A microscope may be used for cell imaging in cytometry; for example, cells may be imaged by a camera and a microscope, e.g., by a camera forming an image using a microscope. An image formed by, and used for, cytometry typically includes more than one cell.

Optical Systems

Figure 6A:
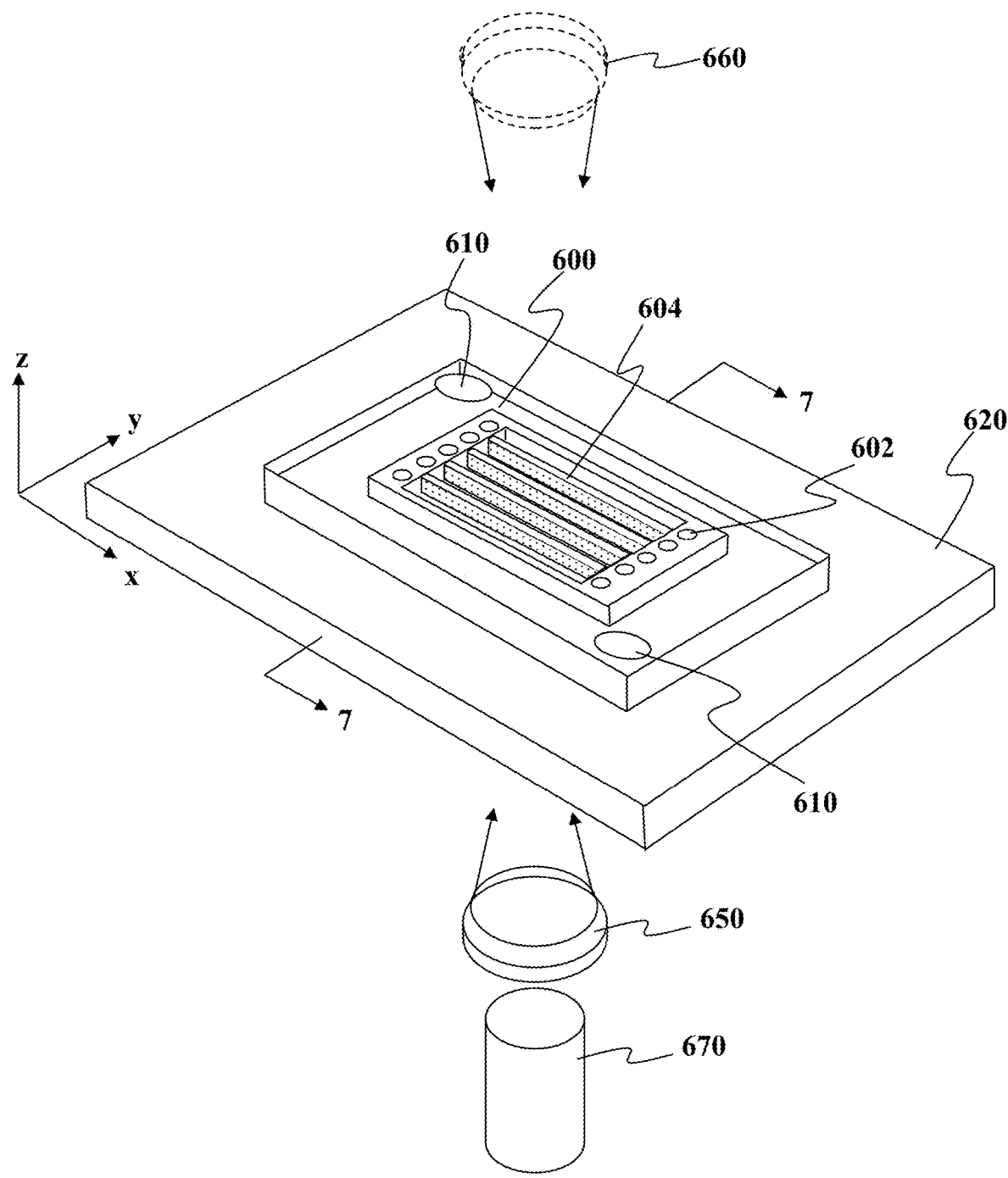
FIG. 6A shows an embodiment of an optical system suitable as part of device or system as disclosed herein, and suitable for use in methods disclosed herein, including exemplary optics (e.g., a light-source shown as a ringlight, and an objective), cuvette, and a support structure configured to hold and position a cuvette for imaging. In this embodiment, the cuvette has a rectangular horizontal cross-sectional shape.
Figure 6B:
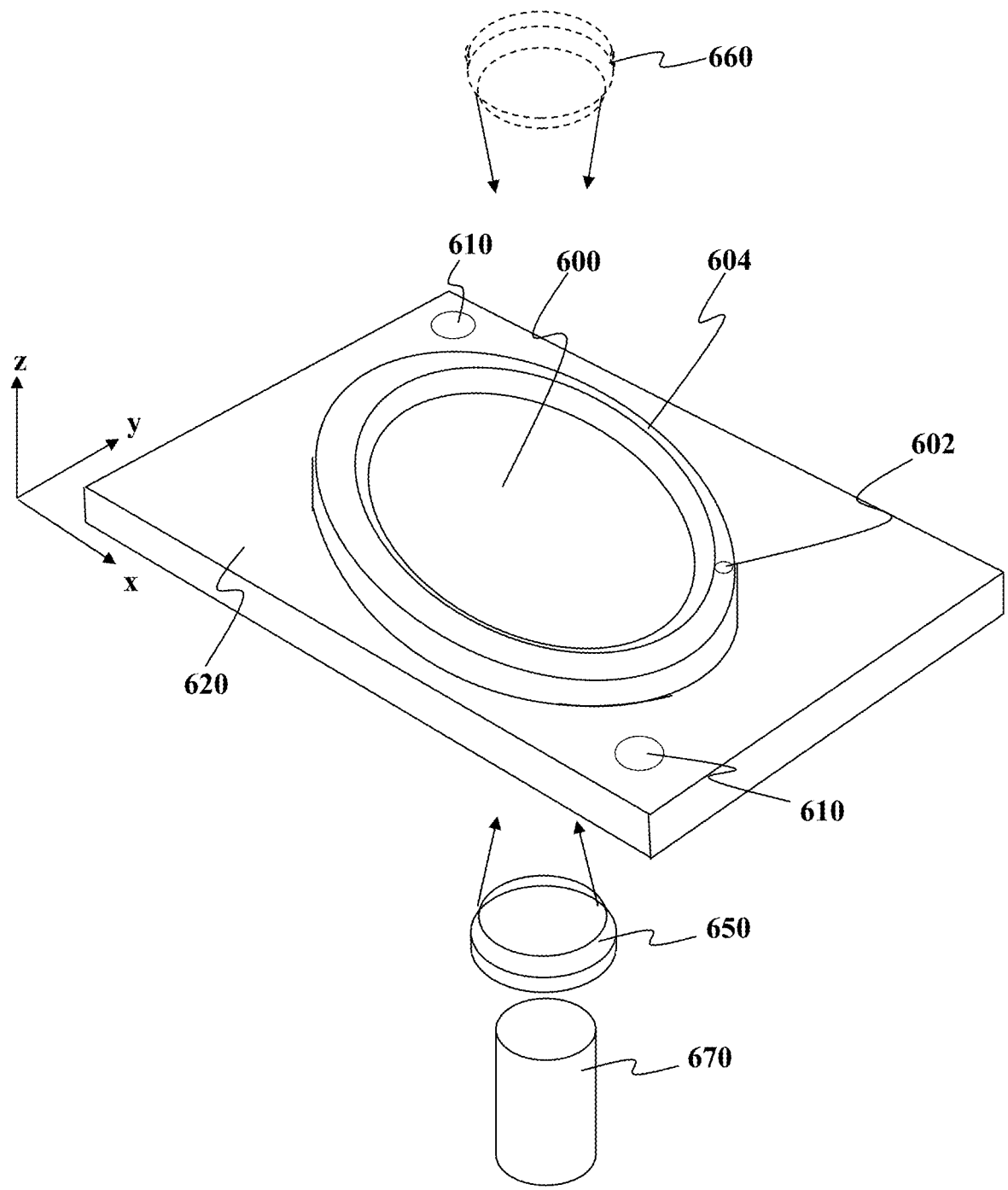
FIG. 6B shows an embodiment of an optical system suitable as part of device or system as disclosed herein, and suitable for use in methods disclosed herein, including exemplary optics (e.g., a light-source shown as a ringlight, and an objective), cuvette, and a support structure configured to hold and position a cuvette for imaging. In this embodiment, the cuvette has a circular horizontal cross-sectional shape.

Referring now to FIGS. 6A and 6B, embodiments of an optical system suitable for use herein will now be described. Although these embodiments of the system are described in the context of being able to perform cytometry, it should also be understood that embodiments of the system may also have uses and capabilities beyond cytometry. By way of example and not limitation, the imaging and image processing capabilities of the systems disclosed herein may be used for many applications, including applications outside of cytometry. Since images of the sample being analyzed are captured, and image information is typically linked or associated in the system to quantitative measurements, one can further analyze the images associated with the quantitative information to gather clinical information in the images that would otherwise be unreported.

A sample to be analyzed, e.g., by cytometry or other optical or imaging means, may be held in a sample holder for analysis. For example, a cuvette may serve as such a sample holder. The embodiment shown in FIG. 6A shows a perspective view of a cuvette 600 that has a plurality of openings 602 for receiving a sample or portion thereof for analysis. The horizontal cross-sectional shape of the embodiment of FIG. 6A is a rectangular horizontal cross-sectional shape. Although the system is described in the context of a cuvette, it should be understood that other sample holding devices may also be used in place of or in combination with the cuvette 600.

As seen in the embodiment of FIG. 6A, the openings 602 may allow for a sample handling system (not shown) or other delivery system to deposit sample into the opening 602 which may be connected with, and may lead to, an analysis area 608 in the cuvette where the sample can be analyzed. In one nonlimiting example, an analysis area 608 may be a chamber. In another nonlimiting example, an analysis area 608 may be a channel. In embodiments, an analysis area 608 that is configured as a channel may connect two entry ports 602. In a still further nonlimiting example, an analysis area 608 may be a channel wherein the sample is held in a non-flowing manner. In any of the embodiments herein, the system can hold the samples in a non-flowing manner during analysis. Optionally, some alternative embodiments may be configured to enable sample flow through the analysis area before, during, or after analysis. In some embodiments, after analysis, the sample is extracted from the cuvette 600 and then delivered to another station (in a system having multiple stations) for further processing and/or for further processing and/or analysis. Some embodiments may use gate(s) in the system to control sample flow.

FIG. 6A shows that, in some embodiments of a cuvette 600, a cuvette 600 may have a plurality of openings 602. Sample may be added to the sample holder via entry ports 602. An opening 602 may be operably connected with (e.g., in fluid continuity with) an analysis area 608. An analysis area 608 may be operably connected with (e.g., in fluid continuity with) a plurality of openings 602. It will be understood that some embodiments may have more, or may have fewer, openings 602 in the cuvette 600. Some embodiments may link certain openings 602 such that selected pairs or other sets of openings 602 can access the same channel (e.g., analysis area 608 that is configured as a channel). By way of nonlimiting example, there may an opening 602 at each end of an analysis area 608. Optionally, more than one opening 602 may be at one end of an analysis area 608.

Embodiments of a cuvette 600 may have structures 610 that allow for a sample handling system to engage and transport the cuvette 600. A cuvette 600 as illustrated in FIG. 6A and FIG. 6B may be engaged by a sample handling system via an element 610, effective that the cuvette 600 may be transported from one location to another. An element 610 may also be used to secure a cuvette 600 at a desired location, e.g., prior to, or following transport to a location (such as over a detector for optical imaging and analysis), a cuvette 600 may be held in position by an element 610 or by a tool or device which uses an element 610 to hold a cuvette 60 in position. In one nonlimiting example, the structures 610 can be openings in the cuvette 600 that allow for a pipette or other elongate member to engage the cuvette 600 and transport it to the desired location. Optionally, in place of or in combination with said opening(s), the structures 610 can be, or may include, a protrusion, a hook, a magnet, a magnetizable element, a metal element, and/or other feature that can be used to engage a cuvette transport device. In embodiments, force (e.g., compression, or other force) may be applied to a cuvette 600; for example, compression may be applied to a cuvette 600 in order to press a cuvette 600 onto a substrate or surface (e.g., a surface of a base support 620), effective to place the cuvette 600 in effective optical contact with the surface. In embodiments, such force (e.g., compression) may aid in providing desired optical properties, such as providing good contact between a cuvette 600 and a base support 620, effective to allow passage of light without significant distortion at the interface, or without significant reflection at the interface, or other desired optical property. In embodiments, such force (e.g., compression) may be applied, at least in part, via a structure 610 or via multiple structures 610.

As shown in FIG. 6B (in perspective view), a cuvette 600 may have a circular horizontal cross-sectional shape. An opening 602 (or multiple openings 602, which may be present in similar embodiments, not shown in the figure) may allow sample handling system or other delivery system to deposit sample into the opening 602 which may then lead to an analysis area 608 in the cuvette where the sample can be analyzed. Non-limiting examples of suitable analysis areas 608 include an analysis area 608 comprising a chamber, and an analysis area comprising a channel. In embodiments, such an analysis area 608 may be located within an annular structure such as the annular structure 604 shown in FIG. 6B. In embodiments, an opening 602 may be connected with an analysis area 608. In embodiments, an analysis area 608 within a structure 604 may form a continuous ring-shaped chamber, connecting with an opening 608 effective to allow flow within the chamber in either of two directions away from an opening 602. In embodiments, an analysis area 608 within a structure 604 may form a ring-shaped channel or chamber, with one end connecting with an opening 608, and another end separated or blocked off from the opening 602, effective to allow flow within the chamber in only one direction away from an opening 602. In embodiments, such a one-way ring-shaped channel or chamber may have a vent or other aperture at a location distal to an opening 602. In a still further nonlimiting example, the analysis area may be or include a channel wherein the sample is held in a non-flowing manner; a sample may be held in a non-flowing manner in an analysis area 608 that comprises a ring-shaped channel, whether the ring-shaped channel is connected to an opening 602 from two directions, or whether the ring-shaped channel is connected to an opening 602 from only a single direction. In any of the embodiments herein, the system can hold the samples in a non-flowing manner during analysis. Optionally, some alternative embodiments may be configured to enable sample flow through the analysis area before, during, or after analysis. In some embodiments, after analysis, the sample is extracted from the cuvette 600 and then delivered to another station (in a system having multiple stations) for further processing and/or analysis. Some embodiments may use gate(s) in the system to control sample flow.

FIG. 6B shows only a single annular structure 604; however, it will be understood that, in further embodiments of a cuvette 600 shaped as illustrated in FIG. 6B, a cuvette 600 may have a plurality of annular structures 604. For example, a cuvette 600 having a plurality of annular structures 604 may have concentric annular structures 604, of different sizes, with an outer annular structure 604 surrounding one or more inner annular structures 604. Such annular structures 604 may include analysis areas 608 within each annular structure 604. FIG. 6B shows only a single opening 602; however, it will be understood that, in further embodiments of a cuvette 600 shaped as illustrated in FIG. 6B, a cuvette 600 may have a plurality of openings 602. For example, a cuvette 600 having a plurality of annular structures 604 (e.g., having a plurality of concentric annular structures 604) may have a plurality of openings 602 (e.g., each annular structure 604 may have at least one opening 602). It will be understood that some embodiments may have more, or may have fewer, openings 602 in a cuvette 600. Some embodiments may link certain openings 602 such that selected pairs or other sets of openings 602 can access the same channel or chamber. By way of nonlimiting example, there may an opening 602 at each end of an analysis area. Optionally, more than one opening 602 may be at one end of an analysis area 608.

Figure 8A:
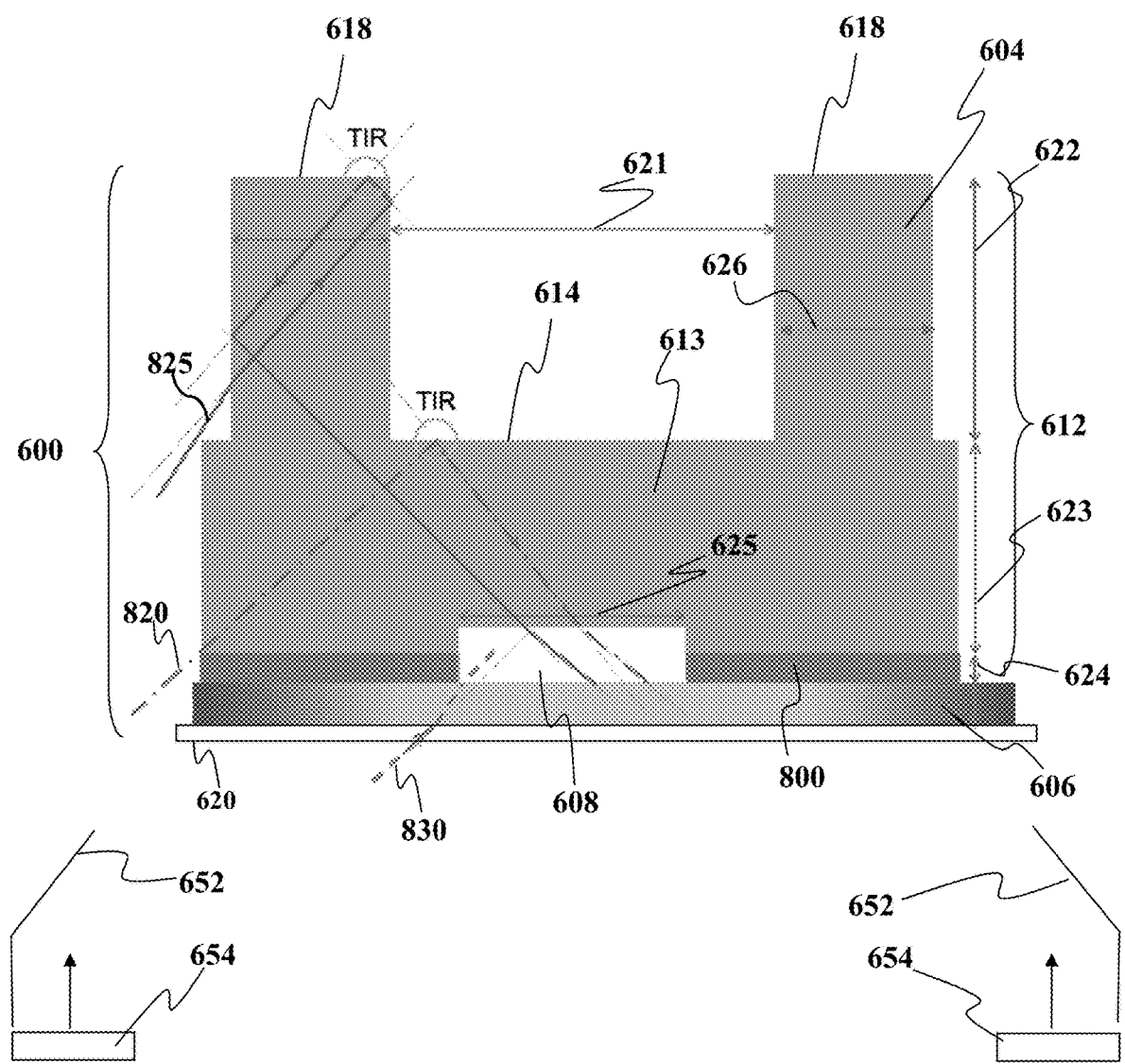
FIG. 8A provides a view of an embodiment of an optical system including a support structure for holding a cuvette for imaging of a sample, in which light from a ringlight illumination system falls directly on the sample (epi-illumination), and light is also reflected from feature of the cuvette so as to provide trans-illumination as well. In this embodiment, the cuvette has a step-shaped vertical cross-sectional shape.
Figure 8B:
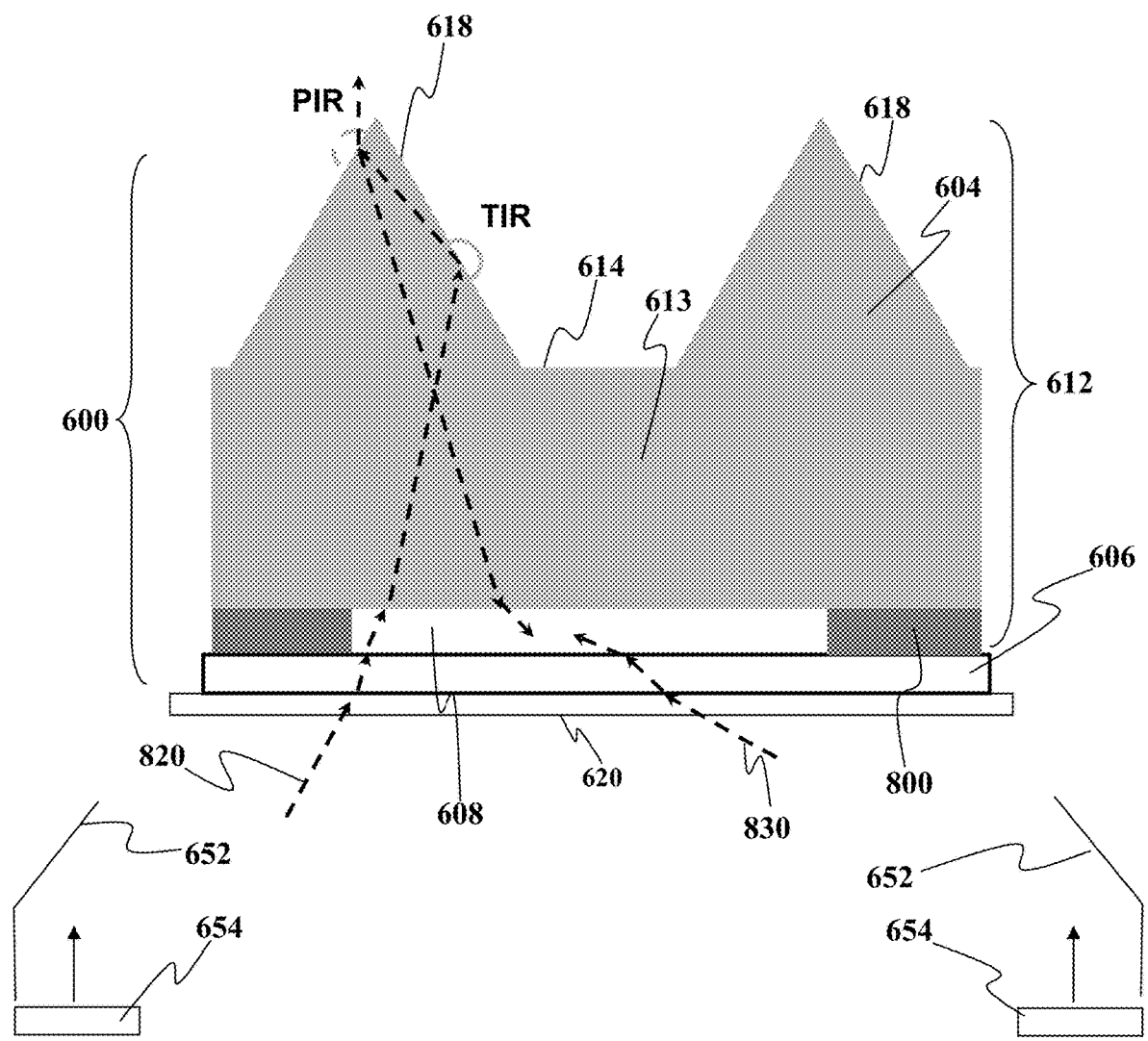
FIG. 8B provides a view of an embodiment of an optical system including a support structure for holding a cuvette for imaging of a sample, in which light from a ringlight illumination system falls directly on the sample (epi-illumination), and light is also reflected from feature of the cuvette so as to provide trans-illumination as well. As shown, incident light may be completely reflected at a surface (total internal reflection, TIR) or only a portion of incident light may be reflected at a surface (partial internal reflection, PIR). In this embodiment, the cuvette has a saw tooth vertical cross-sectional shape.

Some embodiments of cuvettes as illustrated in FIGS. 6A and 6B may provide structures 604 over select areas of a cuvette 600. In one embodiment, the structures 604 are ribs that provide structural support for areas of the cuvette that are selected to have a controlled thickness (e.g., areas 613). For example, the thickness may be selected to provide desired optical properties, including desired pathways for light to follow before and after reflection within the cuvette 600. Such reflection may be partial internal reflection (PIR) or total internal reflection (TIR). Whether such reflection occurs depends on many factors, including the light wavelength; the angle of incidence of the light reaching a surface; the composition of the material (of area 613 and of an environment or material outside the boundary of an area 613); and other factors. In the embodiments shown in FIG. 6A, the structures 604 are rectangular in shape, and have a rectangular cross-section. In the embodiments shown in FIG. 6B, the structures 604 are annular in shape, and may have a rectangular cross-section, or a trapezoidal cross-section, or other shaped cross-section. Such structures may have any suitable cross-sectional shape. As illustrated in FIG. 8B, such structures 604 may have a triangular cross-section (e.g., forming a saw-tooth shaped cross-section when multiple ribs are present). It will be understood that such structures 604 may have other shapes and cross-sections as well (e.g., semi-circular, elliptical, irregular, or other shape), and that, in embodiments, more than one shape may be present in the same system (e.g., a cuvette may include rectangular, triangular, or other shaped structures). The structures 604 may be used when the controlled thickness areas 613 are at a reduced thickness relative to certain areas of the cuvette and thus could benefit from mechanical support provided by structures 604.

In addition to providing structural support, structures 604 may be useful to provide material and pathways for internal reflection of light within a cuvette 600. As shown in FIGS. 8A-8D, light reflected within a cuvette 600 may include pathways for light reflected within a structure 604 (e.g., a rib, or a structure having a triangular cross-section, as shown in the figures, or any other shape, such as a circular or semi-circular cross-section, or other cross-sectional shape). Structures 604 may thus provide convex features extending outwardly from a surface 614 of a cuvette 600; or may provide concave features extending inwardly from a surface 614 of a cuvette 600; or may provide both concave and convex features on a surface 614 of a cuvette 600. Thus structures 604 thus may provide mechanical support to a cuvette 600, may provide desired optical properties, including optical pathways, to a cuvette 600, and may provide other desirable and useful features and capabilities to a cuvette 600 as disclosed herein.

Support structures 604 thus may be useful to provide structural support, including, e.g., stiffness, to a cuvette 600. The optical properties of a cuvette 600 may be important to their use in optical imaging and other optical measurements of samples in an analysis area 608 and of cells, particles, and other components of such samples. Maintenance of the proper flatness of a surface of a cuvette 600, including maintenance of the flatness of a base portion 606, or a surface 614 or 618; maintenance of proper orientation and configuration of a cuvette 600 (e.g., without twisting, flexing, or other distortion); and maintenance of proper positioning of a cuvette 600 (e.g., on a base support 620, or within an optical set-up) may be important to the integrity of optical measurements and images obtained using the cuvette 600. Thus, for example, the design and construction of support structures 604 and base portion 606 may be important factors in providing and maintaining the proper optical properties of a cuvette 600. Maintenance of the proper dimensions of an analysis area 608, including maintenance of the proper distances and relative angles of upper and lower surfaces (or of side walls) of an analysis area 608 may be important to providing correct and consistent illumination of a sample within an analysis area 608. Maintenance of the proper dimensions of an analysis area 608 may also be important to insuring that the volume of an analysis area 608, and so the volume of sample within the analysis area 608, is correct. As discussed herein, force (e.g., compression) may be applied to a cuvette 600 to further insure proper flatness, or to decrease twisting or distortion, or otherwise to insure proper shape, size, and orientation of a cuvette during use. It will be understood that compression may not be required to insure such proper flatness and proper shape, size, and orientation of a cuvette during use. For example, in embodiments, structures 604 alone may be sufficient to aid or insure that a cuvette 600 has the proper flatness and proper shape, size, and orientation during use. In addition, it will be understood that, in embodiments, compression alone may be sufficient to aid or insure such proper flatness and proper shape, size, and orientation of a cuvette 600 during use. It will be understood that, in embodiments, the combination of structures 604 and compression may aid or insure the maintenance of proper flatness and proper shape, size, and orientation of a cuvette during use.

A cuvette 600, including a support structure 606 and cover portion 612, may be made of any material having suitable optical properties. In embodiments, a cuvette 600, including a support structure 606 and cover portion 612, may be made of glass (e.g., quartz, or borosilicate glass, or aluminosilicate glass, or sodium silicate glass, or other glass). In embodiments, a cover portion 612 or a base support 620 may be made of an acrylic, or a clear polymer (e.g., a cyclo-olefin, a polycarbonate, a polystyrene, a polyethylene, a polyurethane, a polyvinyl choloride, or other polymer or co-polymer), or other transparent material. In addition to the optical properties of such materials, the physical properties (e.g., hardness, stiffness, melting point, ability to be machined, and other properties), compatibility with other materials, cost, and other factors may affect the choice of material used to fabricate a cuvette 600. As discussed above, the presence of structures 604, the availability of compression (e.g., as may be applied via a structure 610, or directly to at least a portion of a support structure 606 and cover portion 612), and other factors, may allow the use of materials that may be less rigid than quartz, for example, yet may still provide the requisite optical and mechanical properties for use in the systems and methods disclosed herein. In addition, the presence of structures 604, the availability of compression, and other factors, may allow the use of manufacturing techniques and tolerances that might otherwise not be possible (e.g., due to the possibility of deformation or other factors) in the absence of such structure, compression, and other factors. In addition, the presence of structures 604, the availability of compression, and other factors, may allow the use of materials, including less costly materials, than might otherwise be used in the absence of such structure, compression, and other factors.

Thus, proper design, construction, and materials for support structures 604 and base portions 606 are important for cuvettes 600 and their use.

In some embodiments, these controlled thickness areas 613 (see, e.g., FIGS. 8A, 8B, and 8D) are selected to be positioned over the analysis areas 608. In some embodiments, these controlled thickness areas 613 can impart certain optical properties over or near the analysis areas. Some embodiments may configure the structures 604 to also impart optical properties on light passing through the cuvette 600. Optionally, in some embodiments, the structures 604 may be configured to not have an impact on the optical qualities of the cuvette 600. In such an embodiment, the structures 604 may be configured to have one or more optically absorbent surfaces. For example and without limitation, certain surfaces may be black. Optionally, some embodiments may have the structures 604 formed from a material to absorb light. Optionally, the structures 604 can be positioned to provide mechanical support but do not interact with the optical properties of cuvette 600 near the analysis areas.

For example, certain surfaces, including a surface 614 of a controlled thickness area 613, and a surface 618 of a structure 604, may be coated with a black, or other color, coating. Such a coating may include one layer, and may include multiple, layers. For example, suitable coatings of a surface 614 or 618 may include 2, 3, 4, 5, 6, 7, or more layers. In embodiments, e.g., a surface of a structure 604 (e.g., a surface 618) or a surface 614 may be covered by 3 or 5 layers of coating. Such a coating may include a dye, an ink, a paint, a surface treatment, a colored tape, or other coating or surface treatment. In embodiments, a black or other color marker (e.g., a Paper Mate®, or Sharpie®, or Magic Marker®, or other marker) may be used to coat a surface 614 of a controlled thickness area 613 or a surface 618 of a structure 604. For example, an extra-large black marker may be used to apply multiple coats of black ink to a surface 614 or to the outer surface 618 of a structure 604 to provide an optically absorbent surface and so to improve the optical qualities of a cuvette 600. In embodiments, a surface 614 or 618 may be coated or treated so as to affect or reduce reflectance (whether PIR or TIR) at the surface. A reduction in reflectance at a surface may affect (e.g., reduce) background illumination from a surface.

In embodiments, certain surfaces, including a surface 614 of a controlled thickness area 613, and a surface 618 of a structure 604, may be coated or covered with a material which enhances reflectance at the surface. Reflectance at a surface may be increased, for example, by coating a surface, or attaching a material to a surface; suitable materials for increasing reflectance include aluminum, silver, gold, and dielectric materials (e.g., magnesium fluoride, calcium fluoride, or other salt or metal oxide; or other reflective or dielectric material). Such a coating or covering may include one layer, and may include multiple, layers. For example, suitable coatings and coverings of a surface 614 or 618 may include 2, 3, 4, 5, 6, 7, or more layers. An increase in reflectance at a surface may affect (e.g., increase) trans-illumination from a surface. An increase in reflectance at a surface may aid or enhance imaging of a sample within an analysis area 608, or may aid or enhance optical analysis of a sample within an analysis area 608.

It should be understood that the cuvette 600 is typically formed from an optically transparent or optically transmissive material. Optionally, only select portions of the cuvette 600 (such as, e.g., the analysis areas or areas associated with the analysis areas) are optically transparent or optically transmissive. Optionally, select layers or areas in the cuvette 600 can also be configured to be non-light transmissive. A portion or area of a cuvette may be covered or coated so as to be light absorbing; for example, a surface (or portion thereof) may be coated with a dark, or a light-absorbing, dye or ink. In a further example, a surface (or portion thereof) may be covered with a dark, or a light-absorbing, coating, such as a dark or light-absorbing material, e.g., tape, or cloth, or paper, or rubber, or plastic.

FIGS. 6A, 6B, and 8A-8D illustrate embodiments in which the cuvette 600 rests on a base support 620 wherein some or all of the base support 620 is formed from an optically transparent or transmissive material. In some embodiments, the optically transparent or transmissive portions are configured to be aligned with the analysis areas of the cuvette 600 to allow for optical interrogation of the sample in the analysis area. In one nonlimiting example, the base support 620 can be movable in the X, Y, and/or Z axis to move the cuvette 600 to a desired position for imaging. In some embodiments, the base support 620 comprises a platform or stage that moves only in two of the axes. Optionally, some support structures may move only in a single axis. The cuvette 600 can be configured to be operably coupled to the support structure 600 through friction, mechanical coupling, or by retaining members mounted to one or both of the components. In embodiments, compression, or other force may be applied to a cuvette 600 or a base support 620, or both, in order to ensure adequate contact and proper fit between a cuvette 600 and a base support 620. In embodiments, such compression may aid in ensuring that an optically transmissive surface of a cuvette 600, or of a base support 620, or such surfaces of both, is optically flat and substantially free of distortion. For example in embodiments, a cuvette 600 may be pressed against a base support 620 in order to reduce or obviate any possible optical distortion which might be caused by imperfections or abnormalities in an optical surface of a cuvette 600. In embodiments, such force (e.g., compression) may aid in providing desired optical properties, effective to allow passage of light with distortion at the interface than might otherwise be produced. In embodiments, such force (e.g., compression) may be applied, at least in part, via a structure 610 or via multiple structures 610.

FIGS. 6A, 6B, 8A, 8B, 8C, and 8D further show embodiments in which illumination for darkfield and/or brightfield observation may be provided by an illumination source 650 (such as but not limited to a ringlight as shown) placed below the base support 620 to locate illumination equipment below the level of the cuvette 600. This configuration leaves the upper areas of the cuvette 600 available for pipettes, sample handling equipment, or other equipment to have un-hindered access to openings or other features on a top surface of the cuvette 600. Optionally, some embodiments may locate an illumination source 660 (shown in phantom) above the cuvette 600 to be used in place of, in single, or in multiple combination with underside illumination (e.g., an underside illumination source 650 as shown). An objective 670 can be positioned as shown, or in other configurations, to observe the sample being illuminated. It should be understood that relative motion between the cuvette 600 and the optical portions 650 and 670 can be used to allow the system to visualize different analysis areas in the cuvette 600. Optionally, only one of such components is placed in motion in order to interrogate different areas of the cuvette 600.

Figure 7A:
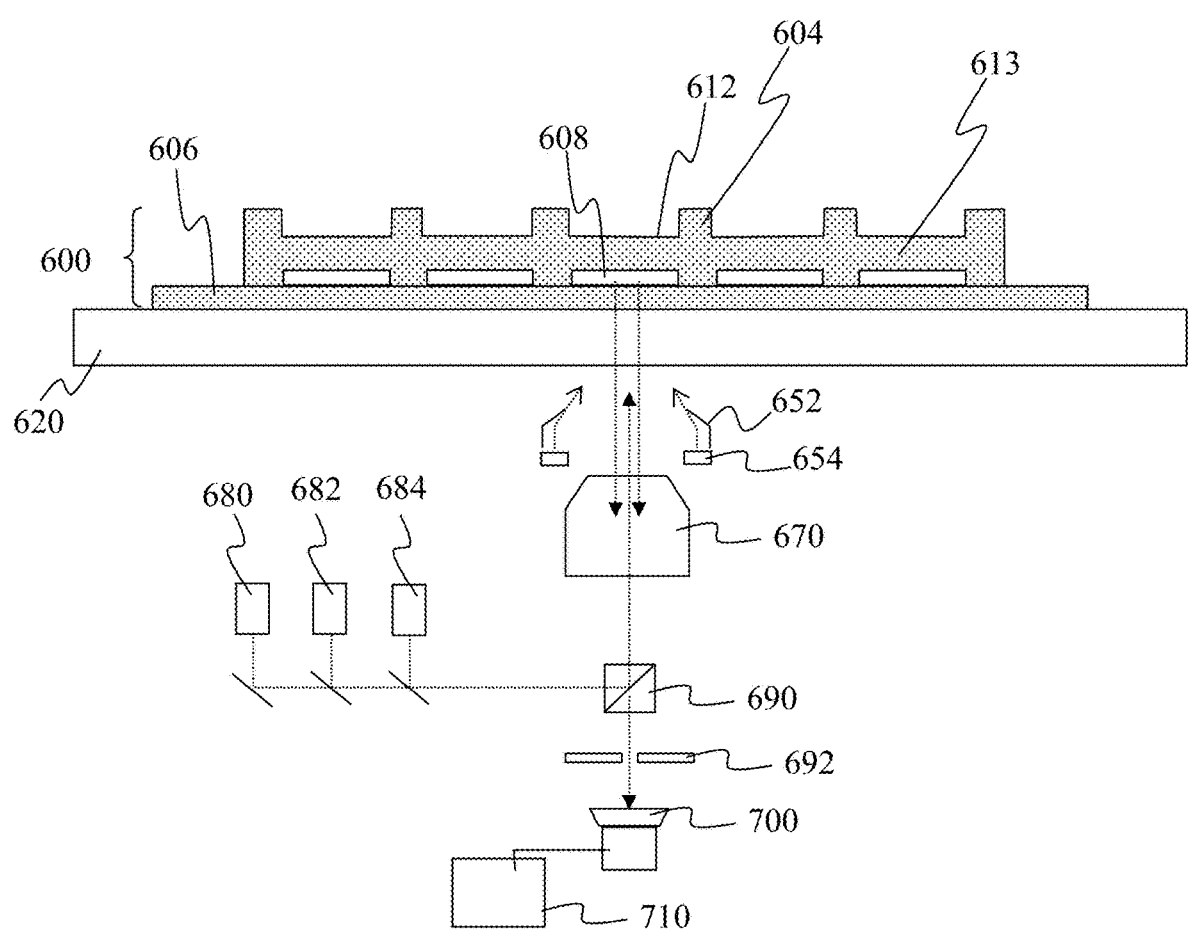
FIG. 7A shows embodiments of elements of an optical system suitable for use in a device or system as disclosed herein, and suitable for use in methods disclosed herein.

Referring now to FIG. 7A, one embodiment of a suitable imaging system will now be described in more detail. FIG. 7A shows a schematic cross-sectional view of various components positioned below the base support 620. The cross-section is along the area indicated by bent arrows 7 in FIG. 6A.

FIG. 7A shows an embodiment in which the cuvette 600 comprises a base portion 606 and analysis areas 608 defined by a cover portion 612. Optionally, the analysis areas 608 may be defined within a single piece. Optionally, the analysis areas 608 may be defined by using more than two pieces, such as but not limited a discrete cover piece for each of the analysis areas 608. In one embodiment, the layer 606 comprises optically clear plastic such as but not limited to cyclo-olefin polymer thermoplastic which deliver superior optical components and applications. Some may form one or more layers or components from glass, acrylic, clear polymer, or other transparent material. The cuvette 600 illustrated in FIG. 7A includes five separate analysis areas 608; these areas are shown in cross-section in the figure; analysis areas 608 having such a cross-section may be rectangular, or square, or other shape. For example, analysis areas 608 may comprise elongated channels providing shallow chambers with relatively large amounts of surface area though which samples may be observed. It will be understood that a cuvette 600 may include a single analysis area 608; or may include two analysis areas 608; or may include three analysis areas 608; or may include four analysis areas 608; or may include five (as shown in FIG. 7A) or more analysis areas 608.

In this nonlimiting example, the sample to be interrogated can be housed in whole or in part in the area 608. By way of non-limiting example, the optics below the base support 620 may include a ringlight 650 that comprises a toroidal reflector 652 and a light source 654. Other illumination components suitable for darkfield illumination may be used; thus the optics may include other sources of illumination, alone or in combination with such a ringlight. Some embodiments may use a mirror. Some embodiments may use a coated reflective surface. Some embodiments may use a different reflector than the ones shown in the figure (e.g., may not use toroidal reflection in illuminating a sample). Some embodiments may use a parabolic reflector. Some embodiments may use a parabolic reflector in the shape of an elliptic paraboloid. Some embodiments may use a plurality of individual reflector pieces. Some embodiments may not use any reflector. Some embodiments obtain oblique illumination through the use of angled light sources positioned to direct light with or without further assistance from one or more external reflectors.

The embodiment illustrated in FIG. 7A shows excitation energy sources 680, 682, and 684 such as but not limited laser diodes at specific wavelengths that are mounted to direct light into the sample in analysis area 608. In one nonlimiting example to facilitate compact packaging, the energy sources 680, 682, and 684 may direct light to a dichroic element 690 (e.g., a dichroic mirror or beamsplitter) that then directs the excitation wavelengths into the analysis area 608. The excitation wavelength(s) cause fluorescence wavelengths to be emitted by fluorophores in marker(s), dye(s), and/or other materials in the sample. The emitted fluorescence wavelengths are funneled through the objective 670, through the dichroic element 690, through an optional filter wheel 692, and into a detector 700 such as but not limited to a camera system. By way of nonlimiting example, the dichroic element 690 is configured to reflect excitation wavelengths but pass fluorescence wavelengths and any wavelengths desired for optical observation.

In one embodiment, all fluorescence excitation wavelengths illuminate the sample in analysis area 608 simultaneously. For example, a detector 700 may be coupled to a programmable processor 710 that can take the captured signal and/or image and deconstruct which wavelengths are associated with which fluorophores that are fluorescing. In some embodiments, excitation sources may illuminate the sample sequentially or in subsets of the entire number of excitation sources. Of course, it should be understood that the system is not limited to fluorescence-based excitation of fluorophores in a sample, and that other detection techniques and excitation techniques may be used in place of, or in single or multiple combination with fluorescence. For example, some embodiments may also collect darkfield illumination scatter information simultaneously or sequentially in combination with fluorescence detection.

Light scattered by an object in a sample within a sample holder (e.g., a cell, or a bead, or a crystal) will be scattered at a plurality of scatter angles, where a scatter angle may be measured with respect to a ray of incident light passing from a light source to the object. Such a plurality of scatter angles comprises a range of scatter angles. Such a sample holder may have features as disclosed herein, and may be configured to provide pathways for internal light reflections. An objective lens configured to image the object will gather and focus the scattered light, where the light may be passed to a detector. Such light focused by an objective lens and focused on a detector may form a spot of light on the detector. In embodiments, the light passing from the objective lens to the detector may be focused by a further lens; such focusing may reduce the size of the spot of light formed on the detector. The light focused on a detector, whether or not it passes through a further lens, will comprise light scattered at a plurality of scatter angles from the object within the sample holder.

Applicants disclose herein methods, systems, and devices (e.g., sample holders) which allow detection of a smaller range of scatter angles than otherwise possible, thereby providing greater resolution and better imaging of samples and of objects within a sample. Applicants disclose herein design features for cuvettes which may be used to control the angles and intensities of light rays incident on the sample, e.g., via PIR and TIR, effective to control the angles at which scattered light is measured.

Due to constraints imposed by non-imaging optics of many systems (e.g. etendue, or the extent of the spread of light passing through the system) the scatter angles of light arriving at a detector can be wider than desired. For example, in some ringlight-cuvette combinations using LEDs as light sources, light rays striking the sample may be spread out to at least 20 degrees around the principal angle. In other words, if the principal ray strikes the sample at 60 degrees, the other rays of the bundle of light rays may strike the sample at scatter angles of about 50 degrees to about 70 degrees. It will be understood that the spread of the cone of scatter angles of light collected by an objective depends upon the numerical aperture of the lens. In such a case, the light collected by the objective lens (e.g., having a numerical aperture of 40 degrees) would be in a cone of about 30-70 degrees. Consequently, light scattered over a wide range of scatter angles will arrive at the detector; for example, such a system will measure all the light scattered by the sample in a large cone centered around 60 degrees+/−40 degrees. However, as disclosed herein, some applications require detection of light within a narrower range of scatter angles, e.g., within a very narrow range of angles (say 60+/−5 degrees). Applicants disclose herein that, in order to provide light measurements from within this narrower range, an aperture can be placed in the Fourier (or back focal plane) of the objective lens (or any plane conjugate with this plane). In the Fourier plane, the angle information is spatially coded. Therefore, depending upon the shape and size of this aperture, light coming from the sample at specific angles can be prevented from reaching the detector (e.g., blocked or filtered out). An annular aperture will block or filter out the inner angles (say 60+/−30 degrees). The resultant measurement can therefore be tailored to the desired angles.

In embodiments, an aperture may be provided through which light from an objective lens passes prior to contacting a detector. In embodiments, an aperture may be provided through which light from a further lens (after passing through an objective lens) passes prior to contacting a detector. Where such an aperture is configured to limit the light which passes through to the detector, the light which passes through will be will be reduced to light from fewer scatter angles, and to light from a smaller range of scatter angles, than the light which passes through in the absence of such an aperture. In embodiments, such an aperture may comprise a single hole, such as a circular hole. In embodiments, such an aperture may comprise a single annulus, such as a circular ring through which light may pass, and having a central area (e.g., a circular area) through which light does not pass. In embodiments, such an aperture may comprise two, or three, or more, concentric annuli through which light may pass, and may include a central area (e.g., a circular area) through which light does not pass. In embodiments, such an aperture may comprise a shape other than a circular or annular shape.

Such an aperture disposed between an objective and a detector, e.g. disposed between a further lens and a detector (where light passes through an objective lens prior to passing through the further lens), provides the advantage of sharper discrimination of the light scattered from the sample, improving the resolution of light-scatter images (e.g., darkfield images) obtained from the sample. In embodiments where light intensity may be a factor, the intensity of light applied (e.g., from a light source, or from multiple light sources) may be increased in configurations having an aperture as disclosed herein, as compared to configurations lacking an aperture as disclosed herein.

Figure 7B:
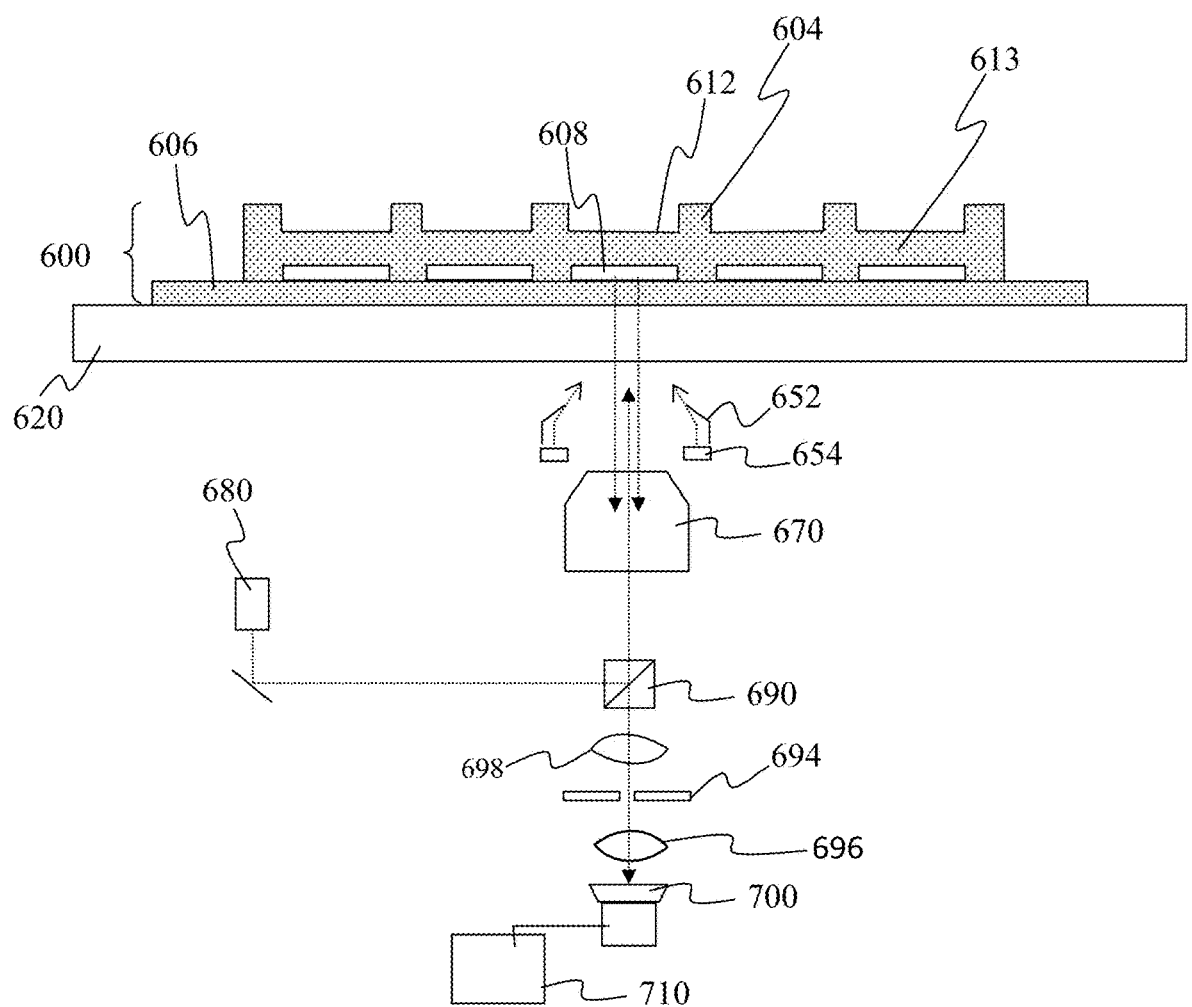
FIG. 7B shows embodiments of elements of an optical system suitable for use in a device or system as disclosed herein, and suitable for use in methods disclosed herein, comprising a further lens and an aperture suitable for limiting the range of angles of scattered light which reach a detector.

A system may include a sample holder having features as discussed and described herein, and light sources, dichroic mirrors, and other elements as shown in FIG. 7A. As illustrated in FIG. 7B, systems having similar features (e.g., similar to those shown in FIG. 7A and other figures herein) may include a sample holder 600, a light source 650 (e.g., light sources 654, or an excitation source 680, or both), an objective lens 670, an aperture 694, a further lens 696, and a Fourier lens 698. An aperture 694 may have a single passage for allowing light to pass thorough to a detector 700. A detector 700 may be operably linked to a processor (e.g., a programmable processor) 710. In embodiments, an aperture 694 may comprise two passages for allowing light to pass thorough to a detector 700. In embodiments, an aperture 694 may comprise three passages for allowing light to pass thorough to a detector 700. In embodiments, an aperture 694 may comprise four, or more, passages for allowing light to pass thorough to a detector 700. In embodiments, a passage in an aperture 694 may comprise a circular hole allowing light to pass thorough to a detector 700. In embodiments, a passage in an aperture 694 may comprise two, or three, or four or more circular holes allowing light to pass thorough to a detector 700. In embodiments, a passage in an aperture 694 may comprise an annulus configured to allow light to pass thorough to a detector 700, and may include a central portion which does not allow light to pass through to a detector 700. In embodiments, a passage in an aperture 694 may comprise two or more annuli (e.g., in embodiments, concentric annuli) each of which is configured to allow light to pass thorough to a detector 700; and such an aperture 694 may include a central portion which does not allow light to pass through to a detector 700. Such an annulus, and such annuli, may have a circular, or elliptical, or other annular shape.

Accordingly, Applicants disclose systems for imaging a sample, comprising: a sample holder, a light source for illuminating an object held within said sample holder, an objective lens configured to collect and focus light scattered from an object held within said sample holder, wherein said scattered light comprises light scattered at a plurality of scatter angles, an optical aperture for passing light from said objective lens, and a further lens configured to focus light from said objective lens onto said optical aperture, wherein said optical aperture is configured to allow only a portion of light focused by said objective lens to pass through the aperture, whereby said portion of light allowed to pass through said aperture consists of light scattered at only a portion of said plurality of scatter angles.

As used herein, the terms "epi" and "epi-illumination" refer to illumination of a sample by light traveling in a direction that is generally away from an objective or other optical element used to observe or image the sample. Thus, in the absence of fluorescence, an image of a sample illuminated by epi-illumination is formed with light reflected or scattered from the sample (light travels from the light source to the sample, and is reflected or scattered by the sample back to the optical elements for observation, imaging, or measurement). As used herein, the terms "trans" and "trans-illumination" refer to illumination of a sample by light traveling in a direction that is generally towards an objective or other optical element used to observe or image the object (light travels from the light source to and through the sample, and continues on to the optical elements for observation, imaging, or measurement). Thus, in the absence of fluorescence, an image of a sample illuminated by trans-illumination is formed with light passing through, or scattered by, the sample.

Where a light source is disposed on the same side of a sample as the objective or other optical elements used to observe or image a sample, light from the light source travels directly to the sample, and the sample is thus typically observed or imaged by epi-illumination. However, even where a sole light source is placed on the same side of a sample as the objective or optical elements, a sample holder as disclosed herein is able to provide trans-illumination of a sample in addition to epi-illumination. Thus, both directions of illumination are enabled without requiring placement of light sources on both sides of a sample. Such a configuration is compact, sparing of resources, and, since the light source and other optical elements are disposed on only one side of the sample holder, the configuration allows unimpeded access to the side of the sample holder without interference by the optical elements. Thus, such a configuration provides the advantage of enabling loading, mixing, and removal of a sample and reagents in the sample holder without interference with optical imaging or measurements, or the apparatus and elements used for optical imaging or measurements.

As illustrated by the images shown in FIGS. 4A and 4B, adding trans-illumination to darkfield images greatly enhances the image and greatly enhances the information available from the image. The methods and systems disclosed herein provide such greatly enhanced images by combining both epi-illumination and trans-illumination, using illumination from a single direction, and, in embodiments, from only a single light source.

As disclosed herein, a sample holder such as a cuvette 600 (e.g., as illustrated in FIGS. 8A-8D) is configured to allow internal reflection of light from a light source (whether PIR or TIR), so that a sample held in an analysis area 608 of a cuvette 600 is illuminated by direct light (epi-illumination; e.g., light travelling along path 830) and is also illuminated by indirect, reflected light (trans-illumination; e.g., light travelling along a path 820 or 825). As disclosed herein, light from a light source disposed on the same side of a cuvette 600 as optical elements 670, 690, 700, etc., may provide both epi- and trans-illumination of a sample.

Referring now to FIGS. 8A-8D, a still further embodiment will now be described. FIGS. 8A-8D show a schematic of a cross-section of a portion of a cuvette 600 and the dark field scatter illumination source such as but not limited to the ringlight 650 shown in FIGS. 6A and 6B. Base support 620 is also shown in FIGS. 8A-8D. FIGS. 8A-8D include brackets and arrows to indicate structures or portions of structures; for example, the bracket labeled 600 indicates the entire cuvette 600 shown in the figure; the bracket labeled 612 indicates the cover portion 612 of the cuvette 600. The arrows 621 to 626 in FIG. 8A indicate dimensions for the indicated portions of the cover portion 612. It will be understood that these dimensions may vary in different embodiments of a cuvette 600, and that such variations may depend upon the size, application, materials, optical wavelengths, samples, and other elements and factors related to the construction and use of a cuvette 600. For example, in embodiments, the distance 621 between support structures 604 may be between about 0.1 millimeter (mm) to about 1 centimeter (cm), and in embodiments may be between about 1 mm to about 100 mm, or between about 1.5 mm to about 50 mm, or between about 2 mm to about 20 mm. In further embodiments, the distance 621 between support structures 604 may be between about 0.5 mm to about 10 mm, or between about 1 mm to about 5 mm. In embodiments, the height 622 of a support structure 604 may be between about 0.1 mm to about 100 mm, or between about 0.5 mm to about 50 mm, or between about 1 mm to about 25 mm. In further embodiments, the height 622 of a support structure 604 may be between about 0.1 mm to about 10 mm, or between about 1 mm to about 5 mm. Similarly, in embodiments, the height 623 of a controlled thickness area 613 may be between about 0.1 mm to about 100 mm, or between about 0.5 mm to about 50 mm, or between about 1 mm to about 25 mm. In further embodiments, the height 623 of a controlled thickness area 613 may be between about 0.1 mm to about 10 mm, or between about 1 mm to about 5 mm. In embodiments, the thickness 624 of a layer 800 may be between about 0.01 mm to about 10 mm, or between about 0.05 mm to about 1 mm, or between about 0.1 mm to about 0.5 mm. In embodiments, the width 625 of an analysis area 608 may be between about 0.05 mm to about 100 mm, or between about 0.5 mm to about 50 mm, or between about 1 mm to about 25 mm. In further embodiments, the width 625 of an analysis area 608 may be between about 0.1 mm to about 10 mm, or between about 1 mm to about 5 mm. In embodiments, the width 626 of a support structure 604 may be between about 0.1 mm to about 100 mm, or between about 0.5 mm to about 50 mm, or between about 1 mm to about 25 mm. In further embodiments, the width 626 of a support structure 604 may be between about 0.05 mm to about 10 mm, or between about 0.5 mm to about 5 mm.

It will be understood that optical components and arrangements for illumination, for excitation, for observation of emission, and the like, as illustrated in any one figure herein, may suggest components and arrangements that may be applied in embodiments of other figures, even if such particular components or arrangements are not explicitly shown in each figure. For example, although a ringlight 650 or other source of illumination 650 is not included in FIG. 8D, in any of the embodiments shown, and in other embodiments, a ringlight 650 or other source of illumination 650 (see, e.g., FIGS. 8A, 8B, and 8C) may be used to illuminate the analysis area 608 (analysis area 608 is shown in FIGS. 8A and 8B). As examples of optical components which are suitable for use with a cuvette 600, ringlight components 652 and 654 are shown in FIGS. 8A, 8B, and 8D; in embodiments, other, or other numbers of, illumination components may be used. For example, light source 654 may be white light or light sources such as but not limited to light emitting diodes (LEDs) or laser diodes with specific wavelength output or output ranges. Optionally, the ring of light source 654 could be fiber optic cable configured to provide a ring of light (e.g., with many splices). Optionally, the light source 654 may be an LED which has a specific narrow divergence angle controlled by the reflector. It may be desirable to control the divergence angle from a ringlight through the selection of the light source and/or through the design of the reflector.

By way of nonlimiting example, a light source 654 may use laser illumination to provide a narrow light pattern, resulting in lower trans-illumination background in the present epi-style lighting configuration (where illumination components are all on one side of the sample) because the light source: provides a narrow spot of light (directed within the sample analysis area 608); provides light of narrow spectral width (e.g., light of wavelengths within a narrow range centered around a particular main wavelength); and is a coherent source. Optionally, use of a LED as the illumination source 654 may also provide a small spot size (e.g., a small spot size within an analysis area 608) and so provide some of the beneficial properties achieved by a laser light source. For these, and other reasons, a laser light source (or an LED providing a small spot size) is effective to lower background signal levels as compared with other illumination configurations. Laser illumination may reduce scattered light as compared to that which typically occurs with more diffuse light sources, and so may reduce the background in one channel (e.g., within a first analysis area 608) by reducing light scattered into that channel from an adjacent channel (e.g., from an adjacent, second analysis area 608). Thus, laser illumination can result in less trans-illumination background than would be expected from illumination by more diffuse light sources. Of course, it is desirable that the decrease in trans-illumination is less than the decrease in background, where the more significant drop in background results in a more distinguishable signal. Optionally, use of a LED as the illumination source 654 provides a diffuse light pattern, with increased background and increased trans-illumination. Of course, it is desirable that the increase in trans-illumination is greater than the increase in background.

Some cuvette embodiments may include cuvettes formed from a plurality of individual layers adhered together, having the cuvette molded from one or more materials, and/or having reflective layers added to the cuvette at different surfaces to enhance single or multiple internal reflections (e.g., to enhance TIR or PIR).

In embodiments, systems, cuvettes, and optical elements disclosed herein may be operating in combination with fluorescence, it may be desirable that darkfield illumination used with such systems and cuvettes not be white light illumination. However, some embodiments may use just white light, e.g., if fluorescence detection is not used in combination with darkfield and/or brightfield microscopy.

FIGS. 8A and 8B shows that in some embodiments, the device may have layers in the cuvette 600 that are optically non-transmissive such as layer 800. This may be useful in embodiments where the light source 654 is diffuse and light is not directed to specific locations. The layer 800 can block light that is not entering the cuvette 600 at desired angles and/or locations. The layer 800 can be configured to be positioned to prevent illumination except through the area below the analysis areas 608. Some may only have specific areas that are blacked out nearest the analysis areas 608. Some embodiments may have blacked out or non-tranmissive material in more than one layer. Some may have blacked out or non-transmissive material in different orientations, such as but not limited to one being horizontal and one being vertical or non-horizontal.

It will be understood that, in embodiments, a layer 800 may be optically transmissive. For example, FIG. 8D presents an embodiment in which a layer 800 is optically transmissive. In some embodiments, a layer 800 may comprise an optically transmissive material having an index of refraction that is different than the index of refraction of a controlled thickness area 613, or of a base support 620, or of both. In some embodiments, a layer 800 may comprise an optically transmissive material having an index of refraction that is the same as the index of refraction of a controlled thickness area 613, or of a base support 620, or of both.

Figure 8C:
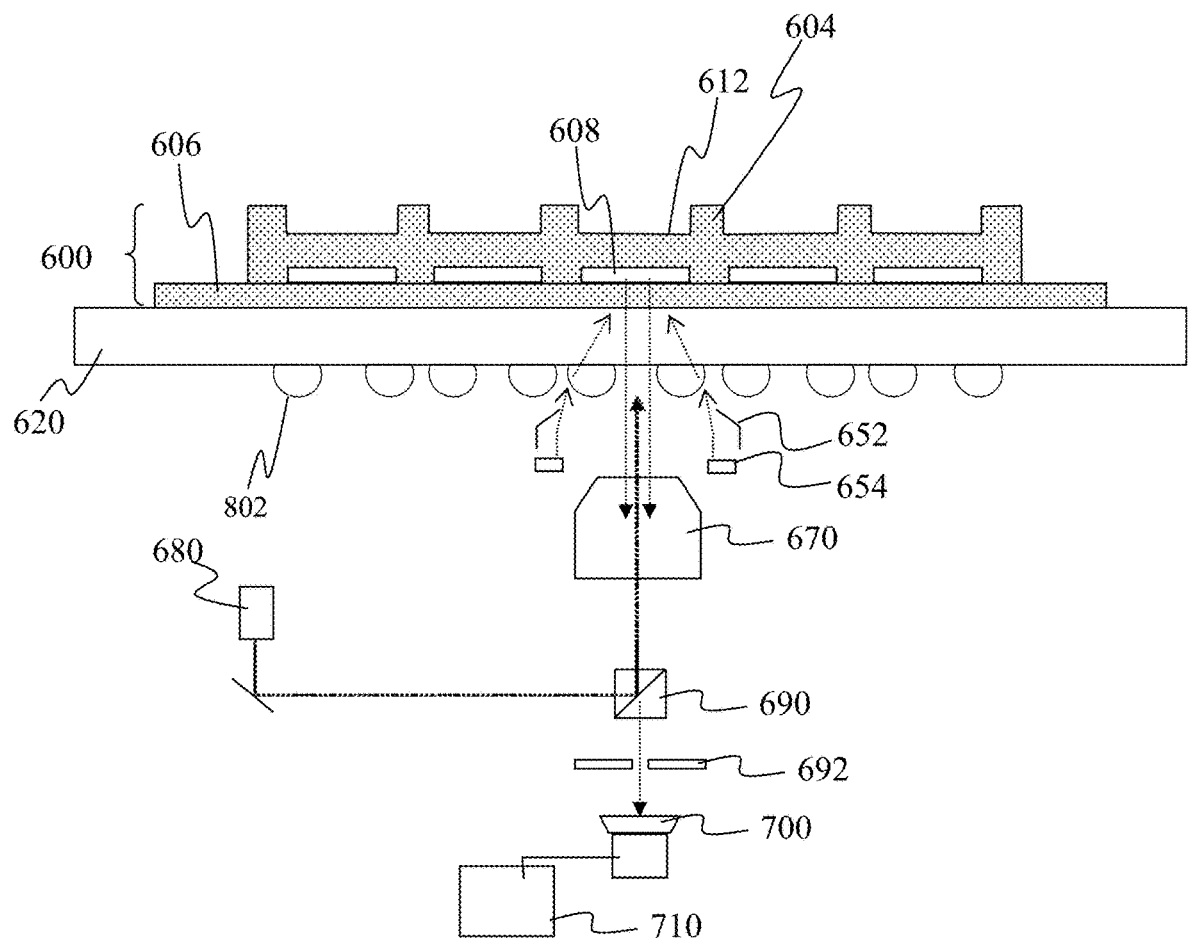
FIG. 8C shows an embodiment of an optical system suitable as part of device or system as disclosed herein, and suitable for use in methods disclosed herein, including exemplary optics (e.g., a light-source shown as a ringlight, and an objective), cuvette, and a support structure configured to hold and position a cuvette for imaging. In this embodiment, the cuvette includes features which affect the path of light illuminating the cuvette and the sample within the cuvette.
Figure 8D:
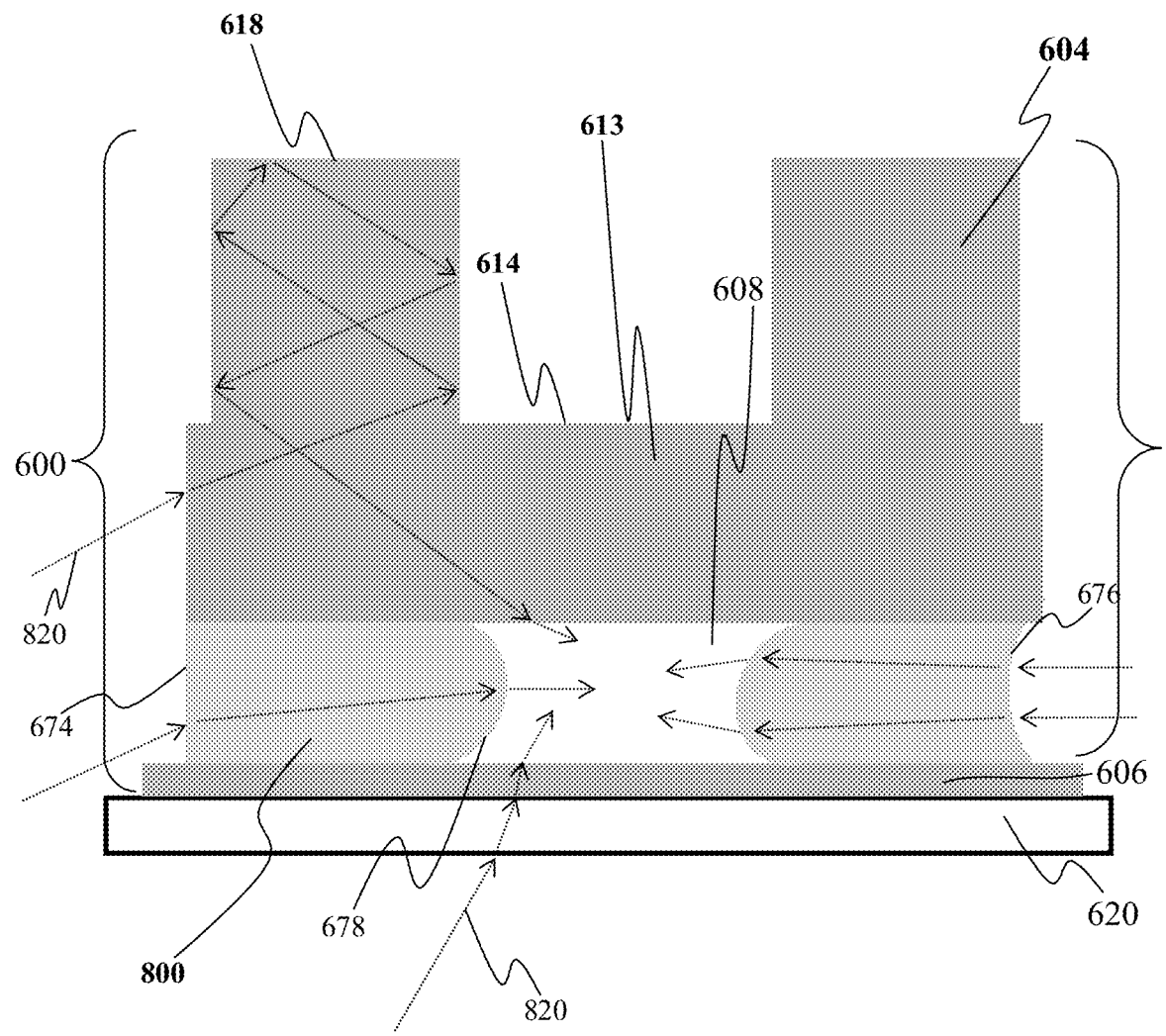
FIG. 8D shows an embodiment of an optical system suitable as part of device or system as disclosed herein, and suitable for use in methods disclosed herein, including exemplary optics (e.g., a light-source directing light from a transverse direction), cuvette, and a support structure configured to hold and position a cuvette for imaging. In this embodiment, the cuvette includes features which affect the path of light illuminating the cuvette and the sample within the cuvette.

In FIGS. 8A, 8B, and 8C, a light source is shown located below a cuvette 600 (near to optics 652 and 654) and provides light directed from below base portion 606. Such a light source may be understood to be in place in the example illustrated in FIG. 8D as well. As shown in these figures, a light source 650 may include a ringlight 654 and a toroidal reflector 652. Other elements, including without limitation lenses, filters, gratings, mirrors and other reflective surfaces, optical fibers, prisms, and other elements may be included. In embodiments, a light source may comprise a laser, or a LED, or other light source; and may comprise a fiber optic which carries light from such a source to another location, and/or which directs light towards an optical element. One design criterion for optical systems is the divergence, or divergence angle, of light from the light source; a light beam of width D with low divergence provides a smaller spot at a given distance from the source than does a light beam of width D with high divergence. In general, a light source 650 which provides light with low divergence is preferred. Such optical elements and configurations may be designed so as to provide light which is substantially collimated, e.g., most or all light is directed along substantially parallel paths towards the sample (e.g., towards an analysis area 608). However, in embodiments where diffuse or scattered light is preferred, a light source 650 with high divergence may be used.

As shown in FIG. 8C, an embodiment of an optical system suitable as part of device or system as disclosed herein may include optics (e.g., a light-source 650, e.g., as shown in FIG. 8C as a ringlight 654, and an objective 670), a cuvette 600, and a base support 620 configured to hold and position a cuvette for imaging. In embodiments as shown in FIG. 8C, a base support 620 may include optical features 802 configured to refract (or diffract, or otherwise alter the path of) light from a light-source 650. As illustrated in FIG. 8C, optical features 802 may comprise an array of lenslets. It will be understood that optical features 802 may comprise any suitable optical feature. In embodiments, optical features 802 may comprise lenslets, or diffraction gratings, or Fresnel lenses, or convexities, or concavities, or other shapes and features which may refract, diffract, or otherwise alter light, or combinations thereof. In embodiments, such optical features 802 may comprise different material than base support 620, and may have a different index of refraction than base support 620. For example, light affected by optical features 802 may be directed towards an analysis area 608, either directly, or indirectly via reflection (e.g., internal reflection) suitable for use in methods disclosed herein, e.g., so as to provide both epi-illumination and trans-illumination of a sample in an analysis area 608. As illustrated in the embodiment shown in FIG. 8C, such embodiments may also include a light path which bypasses optical features 802. Such a light path may be better suited for imaging of a sample within an analysis area 608 than paths which would require imaging through an optical feature 802. In embodiments, both types of light paths (i.e., bypassing optical features 802 and passing through optical features 802) may be provided at the same time, thus providing suitable optics for image analysis of a sample illuminated by both epi-illumination and trans-illumination from a light source situated on the same side of a cuvette 600 as a light source 650.

The cuvette 600 includes features which affect the path of light illuminating the cuvette and the sample within the cuvette. Such trans-illumination may be effected by light reflected within a cuvette 600 (e.g., by internal reflection, including or primarily by partial internal reflection (PIR) or total internal reflection (TIR) from, for example, a surface 612, a surface 604, or other surfaces or combinations of surfaces. Other examples of pathways of light undergoing TIR are shown, for example, in FIGS. 8A, 8B, and 8D.

As illustrated in FIG. 8D, in embodiments, a cuvette 600 of an optical system of a device or system as disclosed herein, and suitable for use in methods disclosed herein, may include features which affect the path of light illuminating internal portions of the cuvette 600, such as light illuminating an analysis area 608, and the sample within an analysis area 608 of a cuvette 600. As shown in FIG. 8D, a layer 800 may include features which refract, diffract, or otherwise affect or alter the path of light entering an analysis area 608. Such alteration of light paths may affect, and may improve, the illumination of sample within an analysis area 608. In the example shown in FIG. 8D, light enters layer 800 from a transverse direction; the light paths are altered by the shape (and material properties) of the layer 800, and are directed as desired into analysis area 608. For example, an external surface of a layer 800 may be flat (e.g., external surface 674) or may be curved (e.g., external surface 676). For example, an internal surface of a layer 800 may be flat (not shown in FIG. 8D; see, however, such surfaces in FIGS. 8A and 8B (although layers 800 in FIGS. 8A and 8B are not optically transmissive, these surfaces are shown as being flat) or may be curved (e.g., internal surface 678 shown in FIG. 8D). In embodiments, such alteration of light paths is effective to provide both epi-illumination and trans-illumination of samples in an analysis area 608.

FIGS. 8A, 8B, 8C, and 8D illustrate light paths within a sample holder providing examples of TIR and PIR within a cover portion 612 at an upper surface 614 and/or at surface 618 in a support structure 604. A sample holder, such as a cuvette 600, may have an optically transmissive surface through which light may pass; in embodiments, such an optically transmissive surface may allow light to pass without significant distortion or diminution in light intensity. A sample holder, such as a cuvette 600, may be made of optically transmissive material, effective that light may pass within the sample holder. In embodiments where a sample holder is at least partially made of optically transmissive material, light may pass through an optically transmissive surface of a sample holder, and may travel within the sample holder. In embodiments, light traveling within a sample holder may be reflected at one or more surfaces, and travel along a reflection path within a sample holder. Where light from a light source disposed outside a sample holder enters a sample holder through an optically transmissive surface of a sample holder, such light may travel within the sample holder away from the light source, and may be reflected at a surface of the sample holder, so that the reflected light may travel in a direction towards the light source after being reflected. Such reflections may be by PIR or TIR.

That is, light passing within a cuvette 600 may reflect off a surface (e.g., a surface 614 or surface 618). Such internal reflections may be effective to illuminate a sample within an analysis area 608 with indirect light; in combination with direct illumination (where the light is not reflected prior to impinging on a sample), the sample may in this way receive epi-illumination (illumination from the same side as the optical detection elements) and trans-illumination (illumination from the side opposite the optical detection elements).

It will be understood that light wavelengths, material, surfaces, and configurations that promote or enhance PIR may not be suitable or effective to promote or enhance TIR. It will be understood that light wavelengths, material, surfaces, and configurations that promote or enhance TIR may not be suitable or effective to promote or enhance PIR. Thus, there are designs and constructions where one or the other of PIR and TIR may be promoted, in the absence of the other. In embodiments, there are designs and constructions where both of PIR and TIR may be promoted. In embodiments, there are designs and constructions in which neither PIR nor TIR are promoted.

As illustrated in FIG. 8A, support structures 604 may have rectangular or square cross-sections. It will be understood that a support structure 604 may have a cross-sectional shape other than square or rectangular; for example, as shown in FIG. 8B, a support structure 604 may have a triangular cross-sectional shape; other cross-sectional shapes (e.g., rounded or semi-circular, or jagged, or irregular) may also be suitable for use with systems and cuvettes disclosed herein. PIR and TIR are tunable features that can selected based on the material used for the cuvette 600, any coatings, cladding, or coverings applied, and the geometry and/or thickness of the controlled thickness area 613 of the cuvette 600. In embodiments, PIR may be preferred, and light, materials, and configurations may be selected to enhance PIR.

In embodiments, TIR may be preferred. In embodiments, the wavelength or wavelengths of light from a light source 650 may be selected to enhance TIR. In embodiments, the material, thickness, surface configuration, and other features of a cuvette 600 may be selected to enhance TIR. For example, the height (as measured from the base of cover portion 612 in contact with layer 800) of the controlled thickness area 613 will affect the angle and intensity of light reflected by TIR that arrives at analysis area 608. Configuration of a cuvette 600 so as to enable TIR of light within the cuvette which allows for oblique angle illumination of a sample (illumination coming from above the sample) is desirable, particularly for darkfield microscopy. In some embodiments, it is desirable to maximize TIR from above the sample. Optionally, in some embodiments a cuvette 600 may be configured to provide TIR only from surfaces over the analysis areas 608. Optionally, some embodiments may be configured to provide TIR only from surfaces over the controlled thickness area 613 (e.g., in the embodiments shown in FIGS. 8A and 8B, generally above analysis area 608). Optionally, in some embodiments, a cuvette 600 may be configured so as to provide TIR of light from other surfaces in the cuvette 600; for example, TIR of light from other surfaces in the cuvette 600 may be provided so as to scatter light at oblique angles, effective that the light is directed back to the analysis area 608.

The design and materials used to construct a cuvette 600 may be selected and configured so as to provide TIR of light. For example, in some embodiments, configurations which provide TIR, or which provide increased or enhanced amounts of TIR, include, without limitation: configurations in which the dimensions of controlled thickness area 613 are compatible with, or which promote, TIR; configurations in which the angle or angles of a surface 614 or a surface 618 (e.g., with respect to incident light) are compatible with, or which promote, TIR; configurations in which the shape, texture, or coating of a surface 614 or a surface 618 is compatible with, or which promotes, TIR; configurations in which the difference between the index of refraction of the material making up a controlled thickness area 613 and that of the material or space in contact with a surface 614 that forms a boundary of a controlled thickness area 613 is compatible with, or which promotes, TIR; configurations in which the difference between the index of refraction of the material making up a support structure 604 and that of the material or space in contact with a surface 618 that forms a boundary of a support structure 604 is compatible with, or which promotes, TIR; and other configurations and designs. In order to enhance the TIR, the first material, within which the light is to be (internally) reflected should have a higher index than that of the second material into which the light would pass if it were not internally reflected; since this second material is usually air, with an index of refraction near 1, this is not usually difficult to ensure. The angle of incidence must be greater than the critical angle in order to provide TIR. For example, referring to embodiments shown in FIG. 8, the materials making up controlled thickness area 613 and structures 604 (e.g., the regions outside surfaces 614 and 618) should have an index of refraction that is greater than that of air. In embodiments where TIR is desired within a layer 800, the material of the layer 800 should have a lower index of refraction than that of controlled thickness area 613 to ensure TIR occurs at the walls illustrated in FIGS. 8A, 8B, and 8D. In alternative embodiments, the material of a layer 800 may have an index of refraction that is higher than the index of refraction of the material of controlled thickness area 613, which will create TIR at that boundary (between a layer 800 and a controlled thickness area 613 effective that the angles and materials may be adjusted so as to optimize the trans-illumination component of light directed at a sample in an analysis area 608.

In embodiments, a surface 614 or 618 may be coated or treated so as to affect or reduce reflectance (whether PIR or TIR) at the surface. In embodiments, a surface 614 or 618 may be coated or treated so as to reduce light leakage out of the surface. For example, even where a surface 614 or 618 is compatible with, or enhances the amount of, TIR, some light may also be transmitted or refracted out of the surface 614 or 618. A light-absorbing coating or material may be placed or applied to such a surface 614 or 618, or to a portion or portions thereof, in order to reduce the amount of stray light leaking from a cuvette 600. Such a light-absorbing coating may be, for example, a dye, an ink, a paint, a surface treatment, a black or colored tape, or other coating or surface treatment. In embodiments, a black or other light-absorbing solid material may be placed against or adjacent to a surface 614 or 618 to provide an optically absorbent surface.

Optionally, in some embodiments, a cuvette 600 may be configured so as not to provide TIR of light (or to provide only insignificant amounts of TIR), or so as not to provide PIR (or only insignificant amounts of PIR), from a portion, or portions, of the cuvette. For example, in some embodiments, a cuvette 600 may be configured so as not to provide TIR or PIR of light (or to provide only insignificant amounts of TIR or PIR) from the support structures 604. Optionally, in some embodiments, a cuvette 600 may be configured so as not to provide TIR or PIR of light (or to provide only insignificant amounts of TIR or PIR) from a surface 618. Configurations which do not provide TIR or PIR, or which provide only insignificant amounts of TIR or PIR, include, without limitation: configurations in which the dimensions of controlled thickness area 613 are incompatible with, or do not promote, TIR or PIR; configurations in which the angle or angles of a surface 614 or a surface 618 (e.g., with respect to incident light) are incompatible with, or do not promote, TIR or PIR; configurations in which the shape, texture, or coating of a surface 614 or a surface 618 is incompatible with, or does not promote, TIR or PIR; configurations in which the difference between the index of refraction of the material making up a controlled thickness area 613 and that of the material or space in contact with a surface 614 that forms a boundary of a controlled thickness area 613 is incompatible with, or does not promote, TIR or PIR; configurations in which the difference between the index of refraction of the material making up a support structure 604 and that of the material or space in contact with a surface 618 that forms a boundary of a support structure 604 is incompatible with, or does not promote, TIR or PIR; and other configurations and designs.

Optionally, in some embodiments a reflective material may be placed at, or attached to, a surface 614 and/or a surface 618. Such a reflective material may be, for example, a metal such as silver, or gold, or aluminum; may be a dielectric, such as magnesium or calcium fluoride, or other salt or metal oxide; or other reflective material. Typically, such a reflective coating may be very thin (e.g., may be less than about 0.1 micron, or may be up to about 100 microns thick). Optionally, a reflective material (e.g., a reflective coating) may be placed at, or attached to, only surface 614. Optionally, a reflective material may be placed at, or attached to, only surface 618. Optionally, surface 618 may be treated to be black so as to be light absorbing. In other embodiments, a surface 614 may be treated to be black so as to be light absorbing. Some embodiments may select the width of the controlled thickness area 613 to be wider than the analysis area 608. For some embodiments using laser illumination, the layer 800 may be removed or be light transmitting as the laser illumination is sufficiently focused so as not to require blackout between analysis areas 608.

By way of example and not limitation, the use of PIR, TIR, or both, can also enable light traveling along path 820 from adjacent areas to be directed into the analysis area 608. As shown in FIGS. 8A, 8B, and 8D, light traveling along path 820 is reflected towards analysis area 608, and light traveling along path 825 undergoes multiple reflections as it travels within cuvette 600 and ultimately to analysis area 608. As shown, light traveling along path 820 in FIG. 8B undergoes multiple reflections as it travels within cuvette 600 and ultimately to analysis area 608. As illustrated in FIG. 8B, such reflections may be PIR or may be TIR. Under traditional terminology, the illumination shown in FIG. 8A by light traveling along paths 820 and 825, and the illumination shown in FIG. 8B by light traveling along path 820, is trans-illumination. The illumination shown in FIGS. 8A and 8B by light traveling along paths 830 shows light coming directly from the ringlight and not by way of TIR: this is epi-illumination. The combination of both types of light components from a light source located below the sample (or only one side of the sample) allows for improved performance as compared to sources that can only provide one of those lighting components. This is particularly useful for darkfield microscopy.

One nonlimiting example of the use of the embodiments shown in FIGS. 8A-8D is darkfield illumination to measure scatter properties of cells in the sample. Darkfield microscopy is an established method that has been used mainly as a contrast-enhancing technique. In darkfield microscopy, the image background is fully dark since only the light scattered or reflected by the sample is imaged. Quantitative darkfield microscopy has not been used to measure scatter properties of cells in a manner comparable to the use of traditional "side scatter" parameter in flow cytometers.

From the hardware perspective, illumination for darkfield microscopy is desired to be oblique, i.e. no rays of light from the illumination light source should be able to enter the objective without contacting the sample first. By way of example and not limitation, illumination should be at a wavelength that does not excite any other fluorophores already present in the sample. Optionally, this illumination allows for the use of high numerical aperture (NA) lenses for imaging. By way of example and not limitation, for traditional lens sizes associated with optical microscopes, the NA may be at least about 0.3. Optionally, the NA is at least 0.4. Optionally, the NA is at least 0.5. Optionally, some embodiments may use oil immersion objective lenses to obtain a desired NA, particularly when lens size is limited below a certain level.

Traditional methods for darkfield illumination have used trans-illumination, where the sample is between the imaging lens and darkfield light source. Thus, in this traditional arrangement, the detection and illumination components are not on the same side of the sample. The traditional epi-illumination methods (where the imaging lens/objective and the light source are on the same side of the sample) require the use of specially manufactured objectives and typically do not allow the use of high NA objectives, thus limiting the capabilities of the whole system.

By contrast, at least some embodiments of darkfield illumination systems described herein have the following attributes. In terms of hardware, the scheme of the embodiments of FIGS. 8A-8D is "epi" in that the ringlight used for darkfield illumination is on the same side of the sample as the objective. This can be desirable from the system-perspective, although alternative embodiments with light sources on the other side may be used alone or in combination with the embodiments described herein. In one non-limiting example, the ringlight is designed such that the LEDs and/or lasers of the light source 654 are all in the same plane and have the same orientation (light sources in the same horizontal plane and directing light upwards). Some embodiments may have light in the sample plane but directing light in a non-parallel manner, such as but not limited to a cone-like manner. Some embodiments may have light in different planes but directing light in the same orientation. Some embodiments may have light in different planes but directing light in a non-parallel manner, such as but not limited to a cone-like manner. In some embodiments, the light is reflected by a toroidal mirror 652 to achieve oblique illumination of the sample.

In addition to the optical properties of the ringlight and the toroidal reflector, the optical properties of the cuvette 600 shown in the embodiments of FIGS. 8A-8D also significantly affects darkfield illumination. In this embodiment, the cytometry cuvette 600 is designed such that light coming from the ringlight 650 falls directly on the sample; but in addition to this, light is also "reflected" on the sample from features of the cuvette so as to emulate "trans" illumination. This reflection can be by way of TIR and/or true reflection.

Note that any trans-illumination scheme allows one to measure forward scattered light from a sample whereas an epi-scheme allows one to measure only the back-scattered light from the sample. Forward scattered light is generally two orders of magnitude greater in intensity than the back-scattered light. Thus, use of trans-illumination allows the use of much lower illumination intensities and reduces harmful side-effects on the sample.

As seen in the embodiment of FIG. 8A, the ringlight 650 (or other source of illumination) and cuvette 600 provide a system that can be tuned such that the intensities of trans and epi-illumination are adjusted for improved performance over traditional epi-illumination. Similarly, the ringlight 650 (or other illumination source) and cuvette 600 provide a system in the embodiment of FIG. 8B that can be tuned such that the intensities of trans and epi-illumination are adjusted for improved performance over traditional epi-illumination. This tuning can be achieved by virtue of the materials chosen (e.g., for their optical properties) and design of cuvette geometry to control angles and extent of total internal reflection.

As shown in FIG. 8C, features 802 may alter the path of incident light, and so be used to enhance both trans-illumination and epi-illumination. As shown in FIG. 8D, the shape and configuration of surfaces 674, 676, and 678 may alter the path of incident light (e.g. transverse illumination), and so be used to provide or enhance trans-illumination, epi-illumination, or both.

Figure 8E:
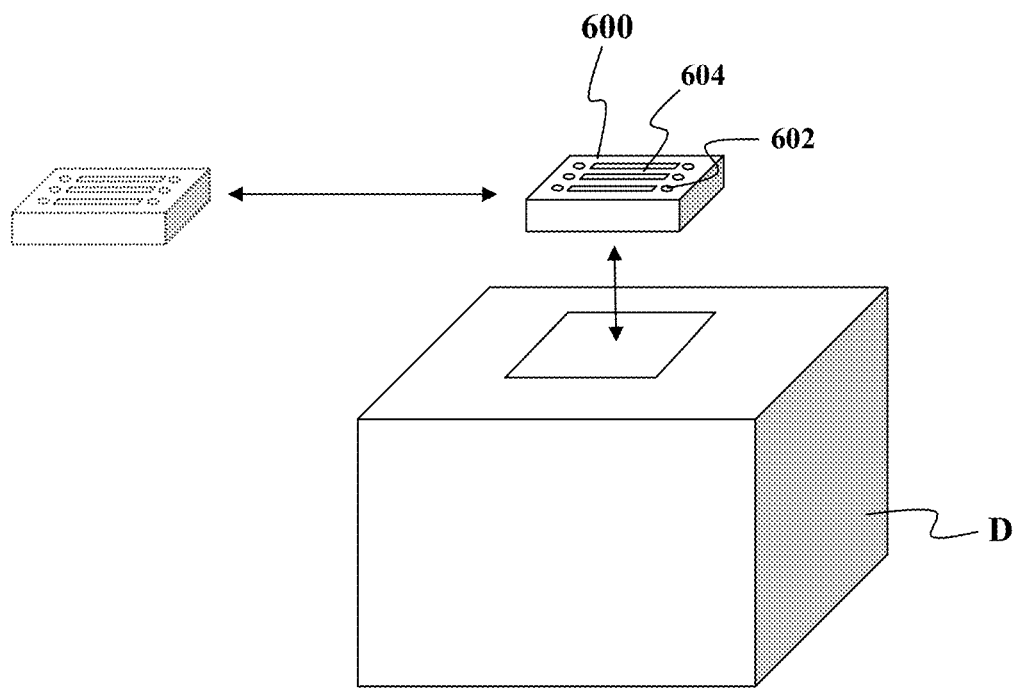
FIG. 8E provides a schematic representation of transport of a cuvette from a sample preparation location to a sample observation location near an optical detector (labeled "D").

FIG. 8E provides a schematic representation of transport of a cuvette 600 from a sample preparation location to a sample observation location near an optical detector D. As indicated in the figure, a sample holder 600 may be moved from one location to a location adjacent to, or on, a detector D. A detector D may include a stage configured to receive, hold, and position a cuvette 600. Sample may be added to the sample holder via entry ports 602 (e.g., six entry ports 602 are shown in the example shown in FIG. 8E), and may then be in a position for optical observation and measurement within an analysis area 608 (not shown, as interior to the surfaces (e.g., of a support structure 604) of cuvette 600 shown in FIG. 8E. Sample that is held within an analysis area 608 may be illuminated, and may be detected by a detector D. In embodiments, a detector D may be configured to make qualitative observations or images, and in embodiments a detector D may be configured to make quantitative observations or images.

A detector D as shown in FIG. 8E may comprise, or be part of, a cytometry unit or cytometry module. Such a cytometry unit or cytometry module may comprise an independent unit or module for sample analysis. In embodiments, other analysis capabilities and devices may be included in a detector D, or may be housed together with, or may be configured for use in conjunction with, a detector D. In embodiments, systems for sample analysis as disclosed herein may comprise such a cytometry unit or cytometry module, e.g., comprising a detector D used to analyze a sample in a cuvette 600. In embodiments, systems for sample analysis as disclosed herein may comprise such a cytometry unit or cytometry module and other units or modules which provide other analysis capabilities and devices in addition to that of a detector D used to analyze a sample in a cuvette 600. In such systems, such other units or modules may be housed together with, or may be configured for use in conjunction with, a detector D. Such other analysis capabilities and devices may be applied to a sample; for example, such analysis capabilities and devices may be used to analyze the sample or portion of a sample that is present in a cuvette 600. In embodiments, such analysis capabilities and devices may be used to analyze a different portion of the sample present in a cuvette 600 (e.g., a sample may be divided into two or more aliquots, where one aliquot is placed in a cuvette 600 for cytometric analysis, and one or more other aliquots are analyzed by other devices housed in, or near, or operated in conjunction with a cytometry unit or cytometry module. Thus, for example, independent of the analysis performed by such a cytometry module, a sample (or portion thereof) may be measured and/or analyzed in a chemical analysis unit, or in a nucleic acid analysis unit, or in a protein analysis unit (e.g., a unit using antibodies or other specifically binding molecules to analyze a sample), or other such unit or combination of units and capabilities. Such analysis may include analysis for small molecules and elements present in a sample (e.g., by a general chemistry unit); analysis for nucleic acid molecules present in a sample (e.g., by a nucleic acid unit); analysis for proteins and/or antibody-reactive antigens present in a sample (e.g., by an enzyme-linked immunosorptive assay (ELISA) unit); or combinations of these. In addition, systems as illustrated in FIG. 8E and as discussed herein may include a controller to control and schedule operations in one or more of the units or modules.

Figure 8F:
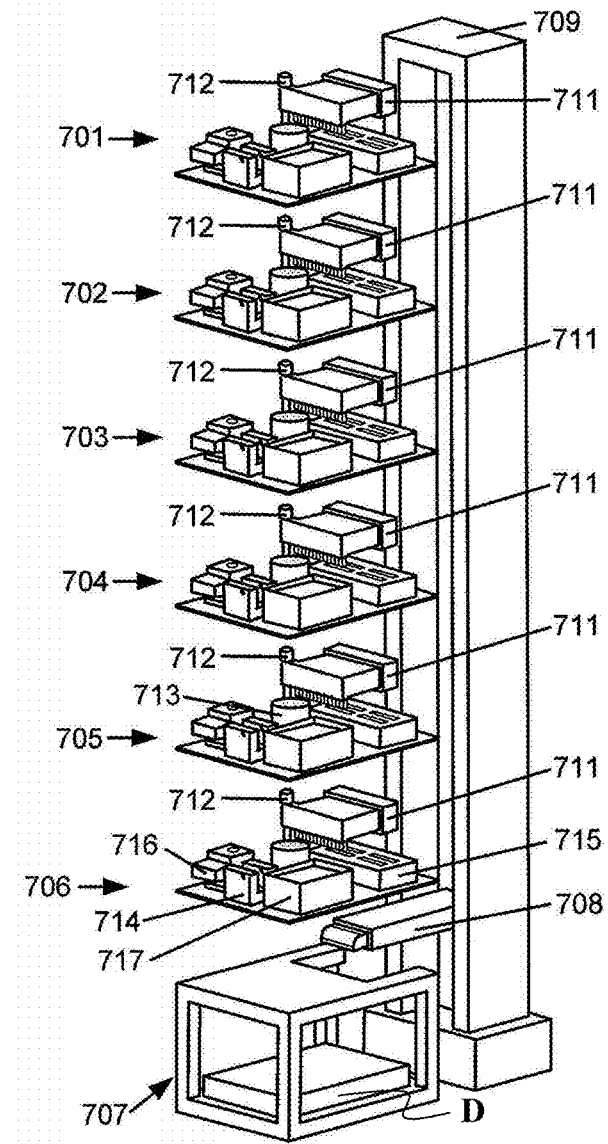
FIG. 8F provides a further, detailed schematic representation of system including a transport mechanism for transporting a cuvette from a sample preparation location to a sample observation location near an optical detector.

FIG. 8F provides a further, detailed schematic representation of system including a transport mechanism for transporting a cuvette from a sample preparation location to a sample observation location near an optical detector D. A system such as a system of the embodiment shown in FIG. 8F may include multiple sample analysis modules, which may be configured to work independently, or, in embodiments, may be configured to work together. The system shown in FIG. 8F includes a single cytometry unit 707, with a detector D; in embodiments, samples (or portions thereof) analyzed in any or all of the analysis modules 701, 702,703, 704, 705, and 706 may be transported to cytometry module 707, for observation and measurement by detector D. Independent of the analysis performed by cytometry module 707, a sample (or portion thereof) may be measured and/or analyzed in a chemical analysis unit 715. Such analysis in a chemical analysis unit 715 may include analysis for small molecules and elements present in a sample (e.g., by a general chemistry unit); analysis for nucleic acid molecules present in a sample (e.g., by a nucleic acid unit); analysis for proteins and/or antibody-reactive antigens present in a sample (e.g., by an enzyme-linked immunosorptive assay (ELISA) unit); or combinations of these.

Systems as illustrated in FIG. 8F may include a controller to control and schedule operations in one or more of the modules 700-707. Samples may be loaded onto sample holders or other elements for analysis in systems as illustrated in the example shown in FIG. 8E. Such systems, and modules of such systems, include, e.g., sample handling systems 708; pipettes for obtaining, moving, and aliquotting samples, including suction-type pipettes 711 and positive displacement pipettes 712; centrifuges 13; spectrophotometers 714; chemical analysis units 715; photomultiplier tubes (PMTS) 716; cartridges 717 for holding disposable supplies and tools, such as, e.g., pipette tips and other tips; and other elements. Modules and other elements may be supported by a rack 709 or other support structure. Samples, disposables, tools, and other elements may be transported within a module, and may be transported between modules (e.g., between a module 701-706 and a cytometry module 707).

FIGS. 8E and 8F show that the sample holder such as cuvette 600 may be transported from one location (such as where sample preparation may occur) and then to another location (such as to the detector D as seen in FIGS. 8E and 8F). The cuvette 600 does not release fluids into or onto the detector D, but instead is self-contained unit that keeps all of the sample therein. There may be one or more, two or more, or three or more locations on or near to the detector D on which there is transparent surface on which the cuvette 600 or other sample holder can engage to provide a transparent interface for sample signal detection to occur. Elements of FIG. 8F and further disclosure regarding such elements and their uses can be found in U.S. patent application Ser. No. 13/769,779, which is hereby fully incorporated by reference herein.

Darkfield

At least some embodiments herein include a dark field illumination source and cuvette. The relevant features of the cuvette 600 relate to designing the cuvette dimensions and optical materials and the geometry of the cuvette. The cuvette increases the extent of darkfield illumination through reflection (e.g., through TIR, or PIR, or both). In one embodiment, the system may simultaneously use trans darkfield and epi darkfield illumination of a sample.

In some embodiments disclosed herein, the cuvette 600 combined with the light source 650 enables trans and epi-illumination using a physical system in the epi configuration (i.e., with the light source and the objective on the same side of sample). The basic cuvette is designed to contain the biological sample and present it for visualization. In embodiments, the cover portion 612 may have a specific design. It is known that different materials may have different indices of refraction; material having a desired index of refraction may be selected for use in fabricating a cover portion 612, or a base support 620, or other elements and components of a cuvette 600 and associated elements and components. For example, in some embodiments, a cover portion 612 or a base support 620 may be made of glass. For example, in some embodiments, a cover portion 612 or a base support 620 may be made of quartz. For example, in some embodiments, a cover portion 612 or a base support 620 may be made of an acrylic, or a clear polymer (e.g., a cyclo-olefin, a polycarbonate, a polystyrene, a polyethylene, a polyurethane, a polyvinyl chloride, or other polymer or co-polymer), or other transparent material.

One can design the material of the top cover portion 612 to facilitate illumination and image collection. In embodiments, to illuminate a sample, the light source 650 may be a ringlight 650 (i.e., may be circular), may have light sources 654 position in a discrete or continuous pattern, and may use a curved reflector 652 to direct light to the sample.

In darkfield microscopy, the sample is illuminated by oblique rays. In darkfield microscopy, the light going into the microscope optics is light scattered by the sample, allowing the measurement of the scatter properties of cells, particles, and other objects and structures in the sample. If no cells, particles, structures, or other objects are present in the sample, then the darkfield image is black.

In the present non-limiting example, the reflector 652 and LED 654 of the ringlight 650 are designed to reflect light so that a minimum fraction of light goes directly back into the objective as non-specific background. The system is designed to direct light by TIR at cuvette surfaces back into the analysis area 608. Light reflected from a surface, whether by TIR or other reflection, is thus directed to illuminate a sample in the analysis area 608. The cells, particles, and structures in the sample in analysis area 608 receive light directly from the ringlight from underneath the cell (i.e., via epi-illumination). In addition, as disclosed herein, light coming from the top surfaces (reflected) is also directed to the analysis area 608 (i.e., via trans-illumination).

Thus, according to the systems and methods disclosed herein, with the ringlight 650 in the same position, light may be directed to illuminate analysis area 608 from two directions (both epi-illumination and trans-illumination) from a single ringlight source. In embodiments, this illumination is all oblique illumination. One can control the relative strengths of the two light components by design of the cuvette and material used for the cuvette.

This darkfield illumination is different from conventional darkfield. For example, in embodiments disclosed herein, darkfield illumination is provided by light reflected at a cuvette surface by TIR. By way of nonlimiting example, in embodiments, a system as disclosed herein may use a reflective layer on the backside of certain surfaces of the cover portion 612 to reflect all of the light. By way of nonlimiting example, in embodiments, a system as disclosed herein may use a reflective layer on the backside of certain surfaces of a cuvette 600 to reflect all of the light. Some embodiments may use a full or selectively reflective background.

For example, in embodiments, it is desirable to direct the light at an oblique angle, which keeps illumination darkfield. In some embodiments light sources 654 may direct light at an angle, and thus may not require or may not use the reflector 652. The reflector 652 may improve manufacturability of the light source 654 since all lights are in the same plane, directed in the same direction. Optionally, the angled light sources 654 may also be used in place of or in combination with a reflector.

It should be understood that even though the light intensity of a trans-illumination component of illumination may be, e.g., 10 times weaker than a corresponding epi-illumination component, the intensity of light scattered from the cells or other objects in the sample due to trans-illumination may be 200 times stronger. That is, where scatter from an amount of epi-illumination is compared to scatter from the same amount of trans-illumination, the intensity of light scattered due to trans-illumination may be 200 times stronger than the light scattered by epi-illumination of cells or other objects in the sample. Thus, a small amount of trans-illumination can significantly enhance the light scatter from cells.

With epi-illumination alone, light collected by an objective is only that light reflected from a sample. However, diffraction is a substantial component of scatter and the use of trans-illumination provides for some amount diffraction (e.g., light diffracted by the sample). However, the light collected from epi-illumination does not include light diffracted by the sample (without reflection of the light back towards the light source following diffraction). Thus, when using trans and epi-illumination there are reflective, refractive, and diffractive components to the light collected by an objective. Traditional methods use all trans darkfield illumination which takes a significant amount of space to configure, due to the placement of optical components on both sides of the sample. In contrast, systems and methods as disclosed herein provide both epi-illumination and trans-illumination using optical elements configured for epi-illumination alone. The embodiments disclosed herein may obtain the space savings of an epi-illumination configuration while providing the benefits of both epi- and trans-illumination of the sample.

Designing the sample holder and the light source together can enable an epi-illumination configuration to increase the amount of trans-illumination of the sample, and in particular may provide uniform trans-illumination. Some embodiments may use mirrored surfaces. Some embodiments use TIR, which can be tuned to create the desired trans-illumination, including trans-illumination that is uniform and at oblique angles into the analysis area 608 for darkfield illumination of the sample. A cuvette 600 may be configured so as to provide trans-illumination of an analysis area 608 solely from a light source in an epi-illumination configuration using reflection, e.g., using TIR or PIR, or both. In one nonlimiting example, a thicker cover portion 612 allows the light undergoing TIR (or PIR, or both) to reflect back into the target area 608. Additionally, the systems and methods disclosed herein not only provide light that, due to TIR (or PIR, or both), comes back into an analysis area 608. but light that comes back into an analysis area 608 uniformly. The embodiments of FIGS. 8A, 8B, and 8D have certain surfaces at certain angles, have certain black surface(s), and certain reflective surface(s) so that the light comes back uniformly to an analysis area 608 effective to provide uniform trans-illumination of a sample in an analysis area 608. Optionally, one could put a fully reflective surface on a top (such as but not limited to a flat cover portion 612 as shown in FIGS. 7A and 7B, and optionally over select areas of a top of an area 613 of FIGS. 8A, 8B, and 8C). In contrast, light traveling within traditional hardware may undergo some reflection, including possibly some TIR (or PIR, or both), but the light may not come back into the area 608.

By way of nonlimiting example, embodiments disclosed herein take an imaging based platform and instead of using a high complication, high cost system which may for example have 16 laser light sources, the present embodiment leverages a more integrated detection system to be able to image and identify the differentials of cells and types in a sample.

In one nonlimiting example, the combination of all these different types of information is useful and effective to achieve the desired goals of the analysis. This may include quantitative measurements and/or qualitative measurements linked to quantitative measurements, or images linked to quantitative measurements. The methods and systems disclosed herein provide different channels of fluorescence where each channel may have one or more specific molecular markers targeted (i.e., quantitative information). The methods and systems disclosed herein may include, and may be used with, microscopy, embodiments herein may provide the ability to observe and measure the background that staining forms inside the cell (e.g., whether it is in the cytoplasm, is it concentrated on the surface, in the nucleus, or elsewhere) that can link image and/or qualitative information that is generated to quantitative measurements that are generated. In this manner, the linkage of the original images that created the quantitative results are available for further analysis if it turns out that the quantitative measurements trigger alarms or meet thresholds the suggest further analysis is desired. Embodiments herein can interrogate background images and information that staining creates in a cell in a sample within an analysis area 608. Such images and information allow the determination of whether or not the staining is in the cell, e.g., in the cytoplasm, in the nucleus, in the membrane, or other organelle or cellular location.

In some embodiments of the methods and systems disclosed herein, combinations of the quantitative scatter properties of the cell, the shape of the cell, and/or the size of the cell may be observed and measured, and used to identify and/or characterize a sample. In some embodiments of the methods and systems disclosed herein, the physical properties, optical properties, and bio/biochemical properties of a sample or portion thereof may be observed and may be measured all in the same device at the same time. All such measurements and observations can be combined in a programmable processor or other processing system to link the various types of information to achieve the goals of the assays (e.g., to achieve a clinical goal of the assays).

Although traditional devices may be suitable for one or the other kind of observation or measurement, they are not suitable for both epi-illumination and trans-illumination from a single light source; there is also no linkage between such different types of information. For example, in some embodiments disclosed herein, where image information that generated the quantitative measurements is retrievable, the systems and method may be used for tissue morphology measurements. Optionally, the system can be applied to pap smear, which is more similar to traditional cytology. It can be extended to anything done using traditional microscopy. In urine, at least some of the present embodiments can look at and analyze crystals and not just cells. One can look at crystals of inorganic salts and chemicals from urine samples that had created certain quantitative readings on one portion of a graph. In addition, one can look at and analyze cells and particles present in blood, including analysis of different types and populations of blood cells, such as but not limited what may be seen in FIG. 1A where different regions of data are circled. Image information for certain data regions can be retrieved to further analyze the underlying cell images that created the measurements plotted on the graph or chart.

Some embodiments herein combine the imaging features with the pathology features. For example, tissue preparation may occur inside a device or system configured to include the optical elements disclosed herein (a system may be, or include, for example, a module or multiple modules configures for optical and other analysis of a sample), and such prepared material can be imaged in this platform. Then the image or analysis may be sent to servers to do image analysis, to do diagnosis, or to perform digital pathology effective to aid or enable a pathologist to analyze a sample.

Embodiments of methods, systems and devices as disclosed herein, including, e.g., systems and devices illustrated in FIGS. 8C and 8D, provide a wide range of cytometry capabilities which may be applied together to analyze a sample. Such cytometry capabilities include cytometric imaging such as is typically confined to microscopy; such microscopic imaging and image analysis of biological samples is provided by the devices, systems, and methods disclosed herein. In addition, the systems and devices as disclosed herein are configured to provide spectrophotometric analysis of biological samples. Such image analysis includes darkfield, brightfield, and other image analysis. Novel and improved methods for applying both epi-illumination and trans-illumination from a single light source are disclosed, which allow more sensitive and accurate images and analysis of blood samples. In conjunction with the methods disclosed herein, separate measurements regarding RBCs, WBCs, and sub-categories of these may be obtained. Image and spectrophotometric analysis as disclosed herein may be used to identify and quantify different populations of WBCs useful for the characterization of a blood sample and for the diagnosis of many clinical conditions. Devices and systems as disclosed herein may be used to provide clinical reports which include general chemical analysis information, nucleic acid-based analysis information, antibody- (or protein or epitope)-based analysis information, spectrophotometric analysis information, and in addition provide images of the cells and samples analyzed. The ability to produce such information and to provide such reports, including images as well as other clinical information, is believed to provide novel and unexpected capabilities and results.

In addition, this information, and these reports, may be produced in a short amount of time (e.g., in less than an hour, or less than 50 minutes, or less than 40 minutes, or less than 30 minutes, or other short amount of time). In addition, this information, and these reports, may be produced from small samples, e.g., small samples of blood or urine. Such small samples may have sizes of no more than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments where a sample is a blood sample, such small sample may be collected from a finger-stick. Typically, only a small amount of blood is collected from a finger-stick (e.g., the amount of blood may be about 250 µL or less, or about 200 µL or less, or about 150 µL or less, or about 100 µL or less, or about 50 µL or less, or about 25 µL or less, or other small amount).

Clinical reports which include cytometric information and images, as disclosed herein (including images, scatter plots, and other optical and imaging information), and which also include general chemical analysis information, nucleic acid-based analysis information, antibody- (or protein or epitope)-based analysis information, and spectrophotometric analysis information, are believed to provide broad and clinically rich information useful for the diagnosis and characterization of many clinical conditions, and to provide advantages over the art. Such reports may be prepared rapidly at a point of service (or point of care) location, and may be rapidly communicated (e.g, electronically by wireless, land-line, optical fiber, or other communication link) to a pathologist or other clinical expert for analysis and interpretation. Such expert analysis and interpretation may then in turn be rapidly communicated (e.g. electronically by wireless, land-line, optical fiber, or other communication link) to a clinician caring for the subject, or back to the point of service (or point of care) location, or both, for rapid feedback. Such rapid feedback enables timely treatment, if necessary, or prevents unnecessary treatment, by providing information and analysis based on samples which may be acquired, may be analyzed, or both, at a point of service or point of care location. Such rapid analysis, reporting, and feedback provides advantages over time-consuming methods, and, by allowing timely treatment and by avoiding unnecessary treatment, may provide more effective, more efficient, and less costly clinical services and treatment. Such more time-consuming methods which may be obviated by the devices, systems and methods disclosed herein include, but are not limited to: delay and inconvenience due to a subject being required to travel to a laboratory or clinic remote from the subject's home, and remote from the clinician entrusted with the care of the subject; delays and possible sample degradation due to transport of a sample from a collection location to a location where the sample may be analyzed; delays due to transmission of the results of such analysis to a pathologist or other expert; delays due to transmission of an expert opinion to the subject's clinician; delays in transmission of clinician diagnosis and treatment of the subject following transmission of an expert opinion to the clinician. These delays, inconveniences, and possible sample degradation may be reduced or eliminated by use of the methods, devices, and systems disclosed herein.

Embodiments of systems and devices as illustrated in FIGS. 6A, 6B, 7, 8A, 8B, 8C, and 8D, and other figures and as disclosed herein, provide cytometry capabilities in a compact format, including in compact formats for use with one or more other sample analysis capabilities. Applicants disclose herein novel devices and systems which include the novel cytometry capabilities as disclosed herein in devices and systems along with other sample analysis capabilities. For example, Applicants disclose herein devices and systems which provide novel cytometry capabilities as disclosed herein in conjunction with devices and systems for sample analysis by a general chemistry unit; in conjunction with devices and systems for sample analysis by a nucleic acid analysis unit; in conjunction with devices and systems for sample analysis using antibody assays (e.g., ELISA) unit); and combinations of these. Thus, a sample processing device as disclosed herein may be configured to perform a plurality of assays on a sample. Such a sample may be a small sample.

In embodiments, all sample assay actions or steps are performed on a single sample. In embodiments, all sample assay actions or steps are performed by a single device or system and may be performed within a housing of a single device. Such systems and devices including cytometry, particularly cytometry which provides image analysis as well as spectrophotometric or other optical analysis in a single unit, are believed to be novel and unexpected. Providing systems and devices including cytometry, particularly cytometry which provides image analysis as well as spectrophotometric or other optical analysis in a single unit, is believed to provide advantages previously unavailable in the art.

Embodiments of systems and devices as illustrated in FIGS. 6A, 6B, 7, 8A, 8B, 8C, and 8D, and other figures and as disclosed herein, provide cytometry capabilities in a portable format, where such devices and systems may be housed in enclosures small enough for easy transport from one location to another. For example, such devices and systems may be readily transported for use at a point of care location (e.g., a doctor's office, a clinic, a hospital, a clinical laboratory, or other location). For example, such devices and systems may be readily transported for use at a point of service location (in addition to such points of care locations discussed above, e.g., a pharmacy, a supermarket, or other retail or service location). A point of service location may include, for example, any location where a subject may receive a service (e.g. testing, monitoring, treatment, diagnosis, guidance, sample collection, ID verification, medical services, non-medical services, etc.). Point of service locations include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

Esoteric Cytometry and Specialty Cytometry Markers

Many traditional advanced or esoteric cytometric assays require a traditional system to measure a large number of markers on cells; typically, these markers are measured simultaneously. The general approach in the field has been tied to high capability instruments including, for example, six or more lasers and 18 different PMT tubes to measure all of these markers simultaneously. However, in many clinical settings, simultaneous measurements of multiple markers are not required. In many clinical requirements, for example, one is interested in seeing how many cells are positive for one marker, or how many are positive for a combination of two or three markers, or other such combination of a few markers. Some embodiments herein provide for multiple combinations of staining schemes where one may have a set of, for example, 10 markers, where one can combine them in sets of 3-4 or 5-6 markers where one can combine them such that even if combining two markers in the same color, some embodiments of the present system can de-convolute the images and information in order to determine which signal came from which marker. This allows some embodiments of the present system to reduce the hardware requirements in terms of the number of light sources, the number of channels used for sample analysis, and other simplifications and efficiencies. Thus, using subsets of a number of markers, or using or measuring markers in non-simultaneous manner in a pre-determined pairing can be useful to enable esoteric cytometry. For example, some markers may be considered to be "gating" markers; such markers are measured first, and if the results of such initial measurements are negative (e.g., the markers are not present, or are present only in low amounts, in a sample), then measurements using other, follow-on markers may not be needed. In embodiments such non-simultaneous methods and systems may reduce the sample volume required for analysis, and may reduce the amounts of markers needed for analysis (e.g., if a follow-on marker is typically used in only a small fraction of samples analyzed).

It should be understood that the use of imaging for cytometric analyses of samples, such as blood or urine samples, enables one to obtain an actual cell count, and so may be more accurate than traditional cytometry methods which do not include such measurements. Imaging of samples, including imaging of cells (and particles or structures) in a sample can actually be more accurate than other methods, such as traditional flow cytometry. For example, traditional flow cytometry gating does not allow for actual counts. The gating in flow cytometry is subjective and thus this can vary from system to system. In addition, traditional flow cytometry does not provide images of cells in a sample.

Some embodiments herein may also gate, but the gating is based algorithmically based on various factors including but not limited to patient health. Classification means is trained on a population of patients knowing if they are healthy or diseased. Some embodiments here can flag a patient that is abnormal and flagging it for review. Self-learning gating can determine if different gating is desired based on information conveyed regarding the patient health. Thus, the gating for the sample for some embodiments disclosed herein is done algorithmically, possibly with a programmable processor, and the gating changes based on patient health.

In embodiments of methods and systems for imaging, one may want to minimize the amount and complexity of hardware required, and one may wish to re-use some or all of the sample if possible, in order to minimize the sample volume required. Thus, the more capability one can extract from the imaging of a sample, the better in terms maximizing the information obtained from a sample, and where possible, from smaller amounts of sample. Thus, the more information one can get to differentiate different cell types from a minimum number of pictures, the more one may minimize the sample volume required.

Optionally, in one non-limiting example, the cuvette for use in the microscopy stage can be configured as follows (with reference to the embodiments and elements shown in FIGS. 7, 8A, and 8B). A middle channel layer comprises a core of thin plastic membrane 800 with pressure-sensitive-adhesive (psa) on both sides. One side adheres to the window-layer 606 and the other side to the molded-top-layer cover portion 612. The core is an extruded film that is black in color, primarily due to optical reasons of preventing light scatter and optical cross-talk between the different liquid channels. The thickness of the core membrane preferably is uniform along its length and width, and may be formed, for example, from an extruded film of black PET or black HDPE (polyethylene). The psa sub-layers on both sides are preferably as thin as possible for preserving the tight and uniform dimensions of the overall liquid channel (e.g., analysis area 608), yet are preferably thick enough to provide a good fluidic seal around the liquid channel. In embodiments, the psa adhesives useful for such sample holders are acrylic in nature and have high adhesion strength for low-surface-energy plastics. The liquid channels, ports and other alignment features on the middle layer may be fabricated using laser-cutting or die-cutting processes.

This embodiment also shows that magnetic elements such as but not limited to magnetic pucks or discs, or metal pucks or discs that may be held by a magnet, may be incorporated into the cuvette. For example, such magnetic elements may be included in, or may comprise, the molded top layer of a sample holder or cuvette. Magnetic elements can be used to simplify hardware used to transport the cuvette. For example, the handling system can engage the magnetic features in the cuvette to transport it without having to add an additional sample handling device.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, different materials may be used to create different reflective surfaces in the cuvette or other surfaces along a light pathway in the optical system. Optionally, the reflective surface is selected so that the reflection is only diffusive. Optionally, the reflective surface is selected so that the reflection is only specular. Some embodiment may use a flat top illumination scheme as set forth in Coumans, F. A. W., van der Pol, E., & Terstappen, L. W. M. M. (2012), Flat-top illumination profile in an epifluorescence microscope by dual microlens arrays. Cytometry, 81A: 324-331. doi: 10.1002/cyto.a.22029, fully incorporated herein by reference for all purposes.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, and other ranges.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are also incorporated herein by reference for all purposes: U.S. Pat. Nos. 7,888,125; 8,007,999; 8,088,593; 8,088,593; 8,380,541; U.S. Patent Publication No. US20120309636; PCT Application No. PCT/US2012/057155; PCT Application No. PCT/US2011/53188; PCT Application No. PCT/US11/53189; U.S. patent application Ser. No. 13/769,779; U.S. patent application Ser. No. 13/244,946; U.S. patent application Ser. No. 13/244,947; U.S. patent application Ser. No. 13/244,949; U.S. patent application Ser. No. 13/244,950; U.S. patent application Ser. No. 13/244,951; U.S. patent application Ser. No. 13/244,952; U.S. patent application Ser. No. 13/244,953; U.S. patent application Ser. No. 13/244,954; U.S. patent application Ser. No. 13/244,956; U.S. patent application Ser. No. 13/769,798; U.S. patent application Ser. No. 13/769,820; U.S. Patent Application 61/766,113; U.S. Application Ser. No. 61/673,245; U.S. Patent Application 61/786,351; U.S. Patent Application 61/697,797; and U.S. Patent application 61/733,886, the disclosures of which patents and patent applications are all hereby incorporated by reference in their entireties for all purposes.

This application claims priority to U.S. Patent Application Ser. No. 61/675,811, filed Jul. 25, 2012; U.S. Patent Application Ser. No. 61/676,178, filed Jul. 26, 2012; U.S. Patent Application 61/766,116, filed Feb. 18, 2013; and U.S. Patent Application 61/802,194, filed Mar. 15, 2013, the disclosures of all of which patent applications are hereby fully incorporated herein by reference in their entireties for all purposes.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2012-2013 Theranos, Inc.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

What is claimed is:

1. A method of identifying a cell in a sample containing a plurality of cells, comprising:
   preparing said cells for analysis by using a first stain which binds to nucleic acids and from this approximate amount of nucleic acid in the sample, determining an approximate number of cells in the sample;
   preparing said cells by using a second stain, wherein an amount of said second stain added to the sample is calculated using the approximate number of cells determined by use of the first stain, in order that a desired ratio of second stain per cell be obtained;
   (a) assaying the plurality of cells for at least one of: (i) the presence of a cell surface antigen; (ii) the amount of a cell surface antigen; or (iii) cell size;
   (b) assaying the plurality of cells of (a) for at least one of: (i) nuclear size; or (ii) nuclear shape; and
   (c) assaying the plurality of cells of (a) and (b) for quantitative cell light scatter, wherein the combination of optical information from steps (a), (b), and (c) is used to identify the cell in the sample containing a plurality of cells, wherein said plurality of cells is held within a sample holder, wherein said sample is held in a non-flowing manner in said sample holder during said assaying of steps (a) and (b), wherein
   said sample holder comprises a cuvette comprising a sample chamber configured to hold a sample, at least a portion of said cuvette comprising an optically transmissive material, said optically transmissive material comprising an optically transmissive surface and a reflective surface, wherein said optically transmissive surface and said reflective surface are configured effective that light passing through the optically transmissive surface simultaneously provides both epi-illumination and trans-illumination to said sample in the sample chamber, where epi-illumination comprises light traveling from said illumination source to the sample without reflection at a surface of the optically transmissive material, and where trans-illumination comprises light traveling within the optically transmissive material and to the sample following at least one reflection from at least one surface of said optically transmissive material
   wherein at least one side of the cuvette is coated with an optically absorbent material and wherein light enters the cuvette from a side opposite the side that is coated.

2. The method of claim 1, wherein said first sample holder comprises an elongated channel.

3. The method of claim 1, wherein said sample holder further comprises one or more optically non-transmissive surfaces.

4. The method of claim 1, wherein said trans-illumination in said sample holder is provided at least in part by partial internal reflection of light at a surface.

5. The method of claim 1, wherein said trans-illumination in said sample holder is provided at least in part by total internal reflection of light at a surface.

6. The method of claim 1, wherein the sample holder comprises two or more sample chambers for holding a sample.

7. The method of claim 1, wherein said cuvette of said sample holder comprises a cross-sectional shape selected from a rectangular horizontal cross-sectional shape and a circular horizontal cross-sectional shape.

8. The method of claim 1, wherein said cuvette of said sample holder comprises a cross-sectional shape selected from a saw tooth vertical cross-sectional shape and a step-shaped vertical cross-sectional shape.

9. The method of claim 1, wherein said at least one concave or convex structure of second sample holder has a cross-sectional shape selected from rectangular, triangular, circular, and semi-circular.

10. The method of claim 1, wherein said sample holder comprises at least one concave or convex structure to provide a pathway for internally reflected light within the sample holder.

11. The method of claim 1, wherein said sample holder comprises at least one concave or convex structure that comprises a surface, and wherein said surface is configured to reflect light within the cuvette.

12. The method of claim 1, wherein said cuvette of said sample holder comprises a cross-sectional shape selected from a rectangular horizontal cross-sectional shape, a circular horizontal cross-sectional shape, a saw tooth vertical cross-sectional shape and a step-shaped vertical cross-sectional shape.

13. The method of claim 1, wherein said sample holder comprises at least one concave or convex structure that comprises a cross-sectional shape selected from rectangular, triangular, circular, and semi-circular.

\* \* \* \* \*